(12) United States Patent
Kopperger et al.

(10) Patent No.: US 11,352,254 B2
(45) Date of Patent: Jun. 7, 2022

(54) MOLECULAR MACHINE

(71) Applicant: Technische Universität München, Munich (DE)

(72) Inventors: Enzo Kopperger, Munich (DE); Jonathan List, Munich (DE); Friedrich C. Simmel, Munich (DE)

(73) Assignee: Technische Universität München, Munich (DE)

( * ) Notice: Subject to any disclaimer, the term of this patent is extended or adjusted under 35 U.S.C. 154(b) by 504 days.

(21) Appl. No.: 16/500,602

(22) PCT Filed: Apr. 6, 2018

(86) PCT No.: PCT/EP2018/058876
§ 371 (c)(1),
(2) Date: Oct. 3, 2019

(87) PCT Pub. No.: WO2018/185295
PCT Pub. Date: Oct. 11, 2018

(65) Prior Publication Data
US 2020/0031663 A1    Jan. 30, 2020

(30) Foreign Application Priority Data

Apr. 6, 2017  (EP) .................................. 17165250
Jan. 18, 2018  (EP) .................................. 18152321

(51) Int. Cl.
*B82B 1/00*    (2006.01)

(52) U.S. Cl.
CPC .............. *B82B 1/002* (2013.01); *B82B 1/003* (2013.01); *B81B 2201/034* (2013.01)

(58) Field of Classification Search
CPC ... B82B 1/002; B82B 1/003; B81B 2201/034; B81B 5/00
See application file for complete search history.

(56) References Cited

U.S. PATENT DOCUMENTS 9,044,808 B2 *   6/2015 Chien ................. B81C 1/00007
2016/0266088 A1 *  9/2016 Sauder ............... G01N 33/5438
(Continued)

OTHER PUBLICATIONS

Chan et al. ("Utilization and control of bio-actuators across multiple length scales," Lap on Chip, Critical Review, 14, pp. 653-670, 2014) (Year: 2014).*

(Continued)

*Primary Examiner* — Yasser A Abdelaziez
(74) *Attorney, Agent, or Firm* — Dascenzo Gates Intellectual Property Law, P.C.

(57) ABSTRACT

A molecular machine comprising a movement part (2) including a first molecular element (4), a second molecular element (5), and a linking element (6) for constraining a relative movement of the first molecular element (4) and the second molecular element (5), and a control part configured to generate an electrical field around the movement part (2), wherein the first molecular element (4) is fixed relative to the control part, wherein the second molecular element (5) is movable relative to the first molecular element (4) in at least one degree of freedom, and wherein the second molecular element (5) is electrically charged such that the second molecular element (5) aligns to said electrical field.

19 Claims, 17 Drawing Sheets

Specification includes a Sequence Listing.

(56) References Cited

U.S. PATENT DOCUMENTS

2017/0250625 A1* 8/2017 Fan .................... B81B 5/00
2018/0037456 A1* 2/2018 Drexler ............... H02N 11/006

OTHER PUBLICATIONS

Hess et al., "Powering Nanodevices with Biomolecular Motors," *Chemistry* (2004), vol. 10, pp. 2110-2116.
Van den Heuvel et al., "Motor Proteins at Work for Nanotechnology," *Science* (July 2007), vol. 317, pp. 333-336.
Fischer et al., "A smart dust biosensor powered by kinesin motors," *Nature Nanotechnology* (Mar. 2009), vol. 4, pp. 162-166.
Van den Heuvel et al., "Molecular Sorting by Electrical Steering of Microtubules in Kinesin-Coated Channels," *Science* (May 2006), vol. 312, pp. 910-914.
Krishnan et al., "Nucleic Acid Based Molecular Devices.,"*Angewandte Chemie Int'l. Edition*, (2011), vol. 50, pp. 3124-3156.
Kopperger et al., "Diffusive Transport of Molecular Cargo Tethered to a DNA Origami Platform," *Nano Letters* (Mar. 2015), vol. 15, pp. 2693-2699.
Marras et al., "Programmable motion of DNA origami mechanisms," *PNAS*, (Jan. 2015), vol. 112, pp. 713-718.
Ketterer et al., "Nanoscale rotary apparatus formed from tight-fitting 3D DNA components," *Science Advances* (Feb. 2016), 2:e1501209, pp. 1-8.
List et al., "Long-range movement of large mechanically interlocked DNA nanostructures," *Nature Communications* (Aug. 2016), vol. 7:12414, pp. 1-7.
Omabegho et al., "A Bipedal DNA Brownian Motor with Coordinated Legs," *Science* (Apr. 2009), vol. 324. pp. 67-71.
Green et al., "Coordinated Chemomechanical Cycles: A Mechanism for Autonomous Molecular Motion," *Physical Review Letters* (Dec. 2008), vol. 101, art. No. 238101, pp. 1-4.
Liber et al., "A Bipedal DNA Motor That Travels Back and Forth between Two DNA Origami Tiles," *Small* (2015), vol. 11, No. 5, pp. 568-575.
Wickham et al., Direct observation of stepwise movement of a synthetic molecular transporter. *Natury Nanotechnology* (Mar. 2011), vol. 6, pp. 166-169.
Asanuma et al., "Photocontrol of DNA Duplex Formation by Using Azobenzene-Bearing Oligonucleotides," *Chembiochem* (2001), vol. 2, pp. 39-44.
Kang et al., "Single-DNA Molecule Nanomotor Regulated by Photons," *Nano Letters* (2009), vol. 9, No. 7, pp. 2690-2696.
Suzuki et al., "Dynamic Assembly/Disassembly Processes of Photoresponsive DNA Origami Nanostructures Directly Visualized on a Lipid Membrane Surface," *Journal of the American Chemical Society* (2014), vol. 136, pp. 1714-1717.
Rothemund, Paul W. K., "Folding DNA to create nanoscale shapes and patterns," *Nature* (Mar. 2006), vol. 440, pp. 297-302.
Douglas et al., "Self-assembly of DNA into nanoscale three-dimensional shapes," *Nature* (May 2009), vol. 459, pp. 414-418.
Lin et al., "Submicrometre geometrically encoded fluorescent barcodes self-assembled from DNA," *Nature Chemistry* (Oct. 2012), vol. 4, pp. 832-839.
Li et al., "DNA-Templated Organic Synthesis: Nature's Strategy for Controlling Chemical Reactivity Applied to Synthetic Molecules," *Angwandte Chemie* (2004), vol. 43, pp. 4848-4870.
He et al., "Autonomous multistep organic synthesis in a single isothermal solution mediated by a DNA walker," *Nature Nanotechnology* (Nov. 2010), vol. 5, pp. 778-782.
Rant et al., "Detection and Size Analysis of Proteins with Switchable DNA Layers," *Nano Letters* (2009), vol. 9, No. 4, pp. 1290-1295.
Yang et al., "A Photoregulated DNA-Based Rotary System and Direct Observation of its Rotational Movement," *Chemistry* (2007), vol. 23, pp. 3979-3985.
Campos el al., "Electronically addressable nanomechanical switching of i-motif DNA origami assembled on basal plane HOPG," *ChemComm* (2015), vol. 51, pp. 14111-14114.

\* cited by examiner

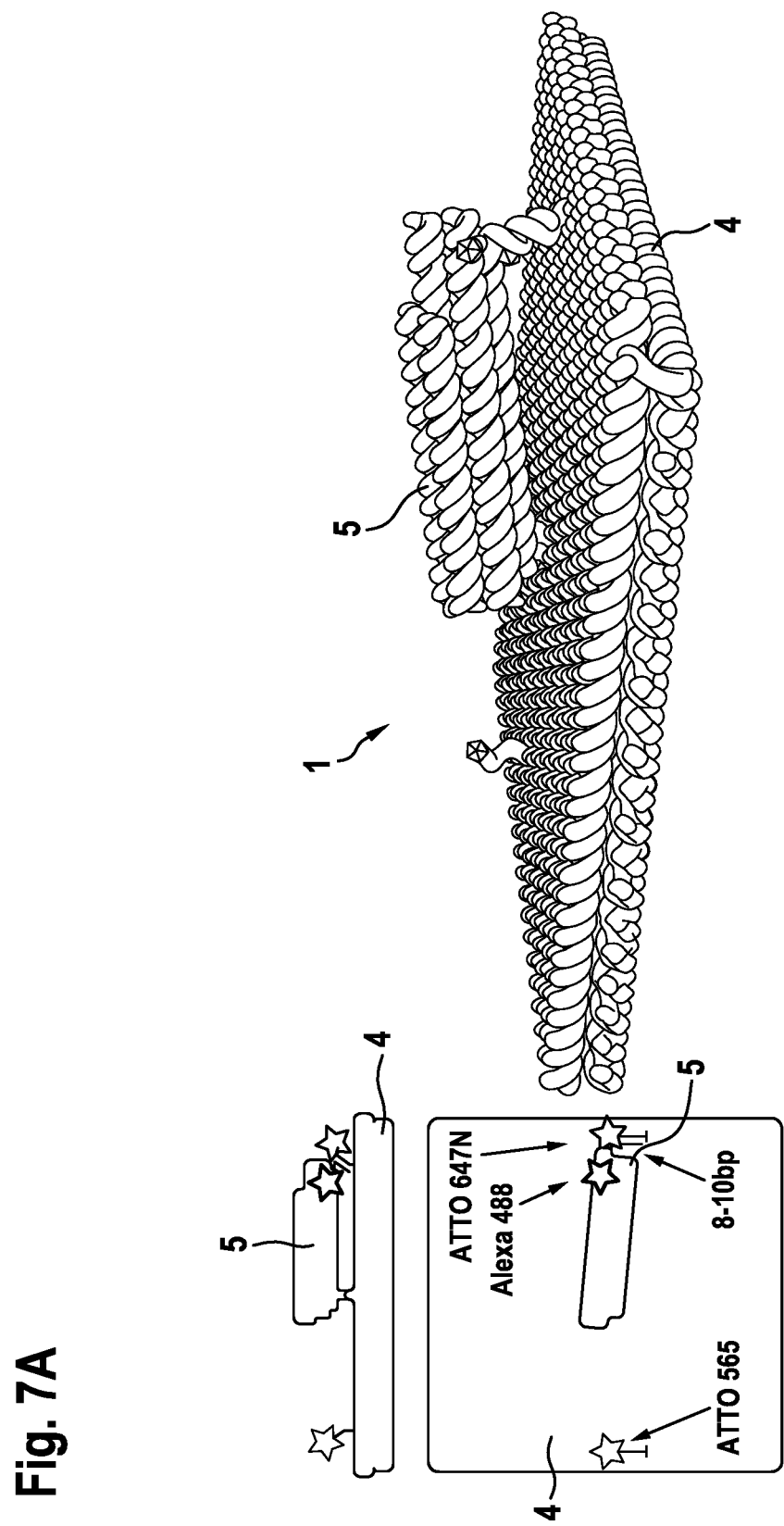

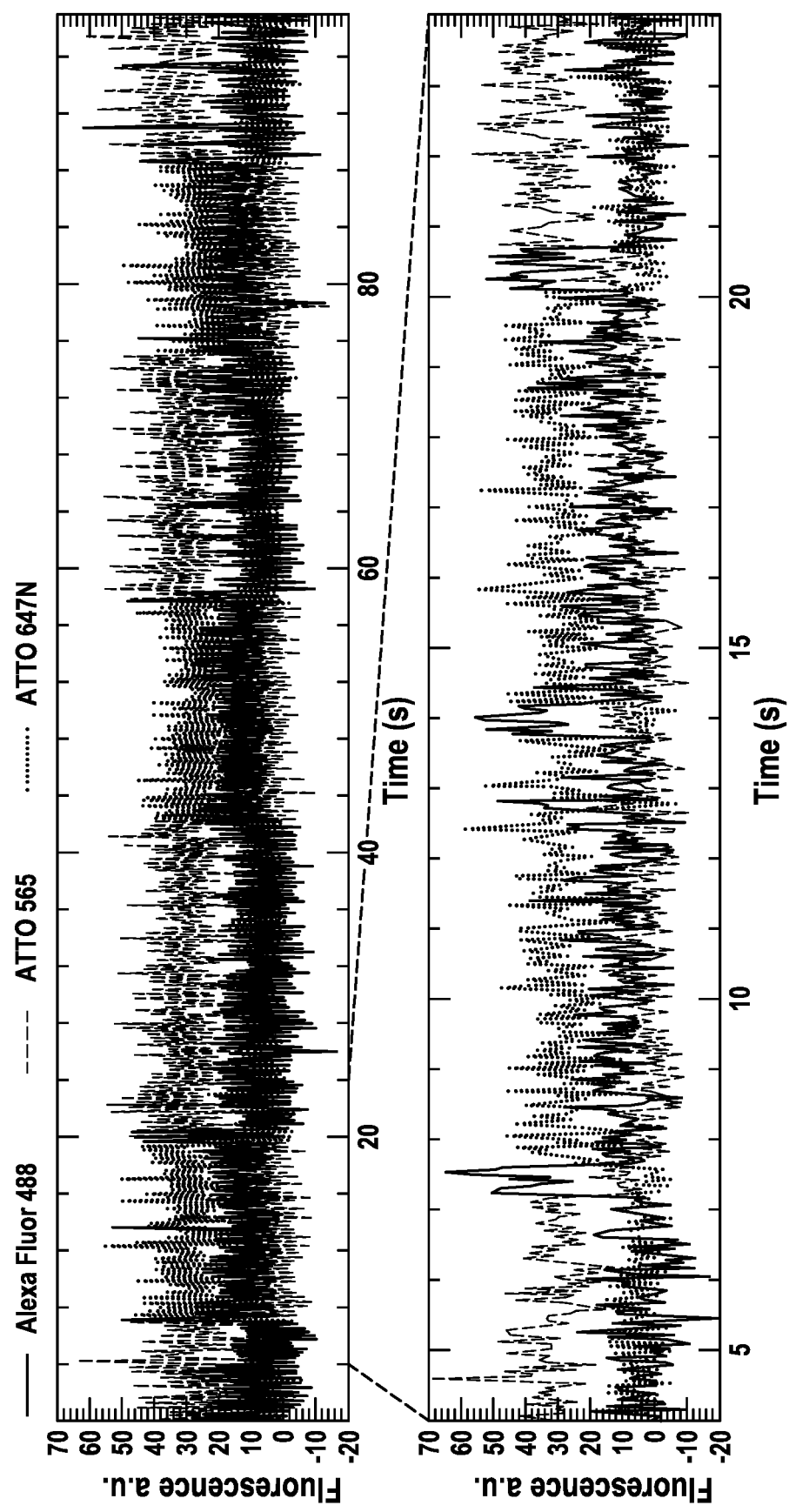

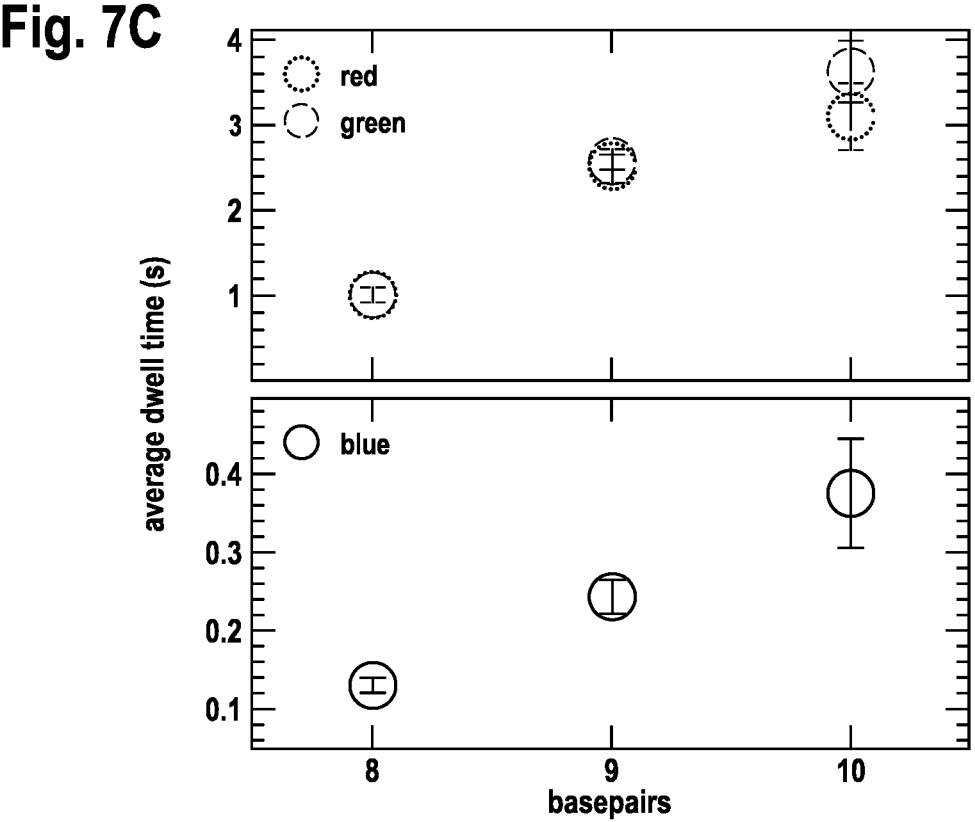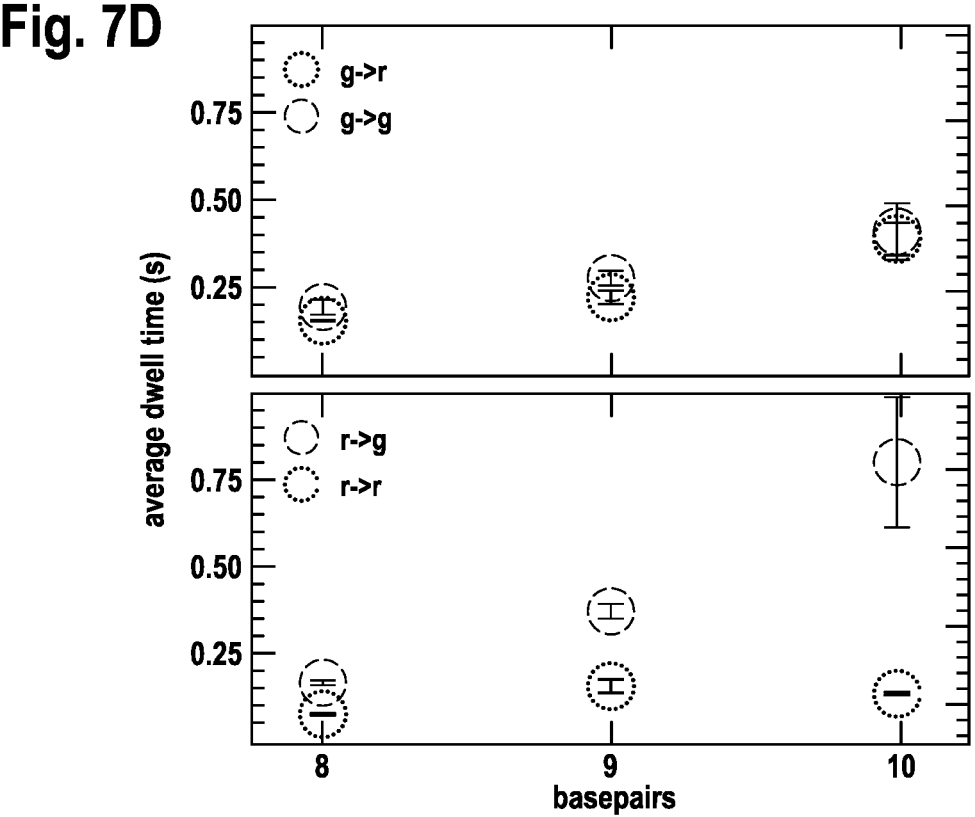

Fig. 8C
top view
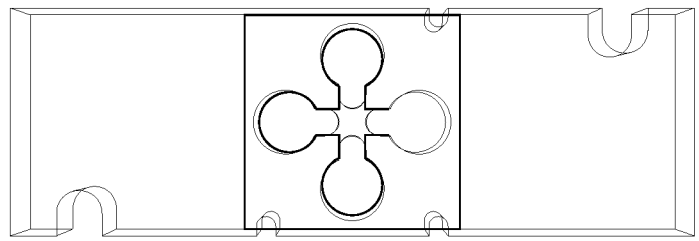
isometric view
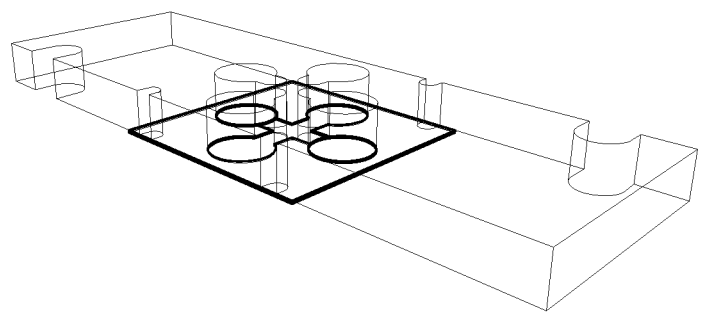
Fig. 8D
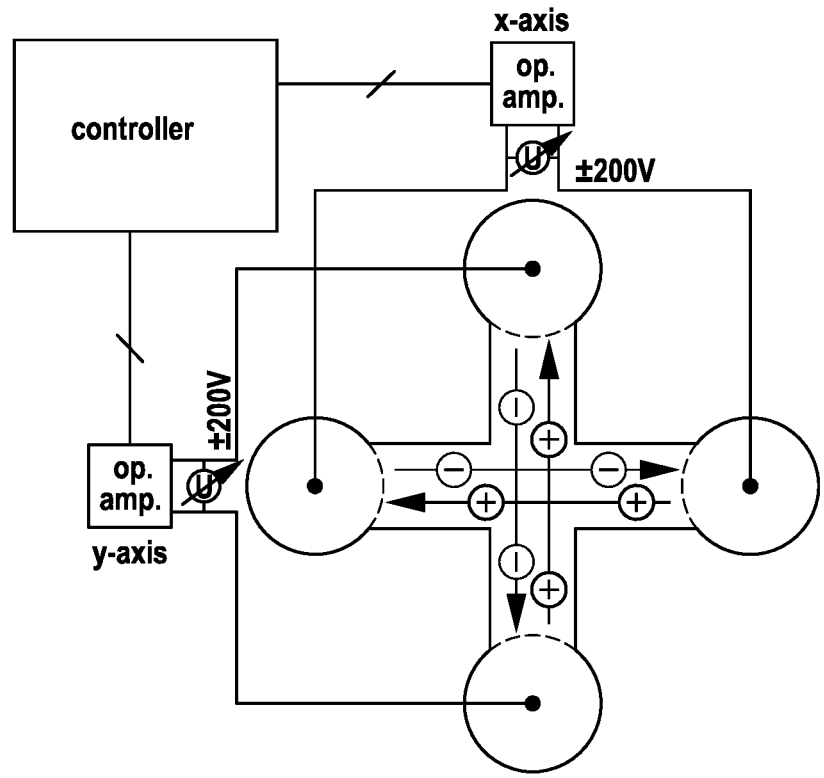

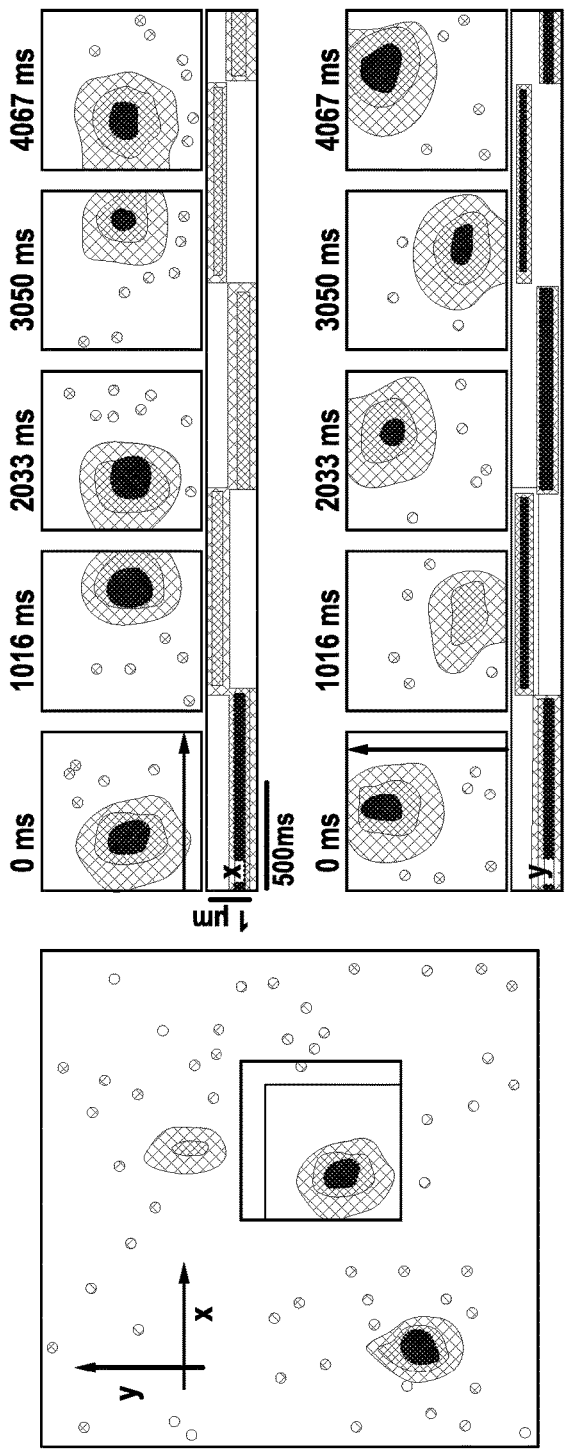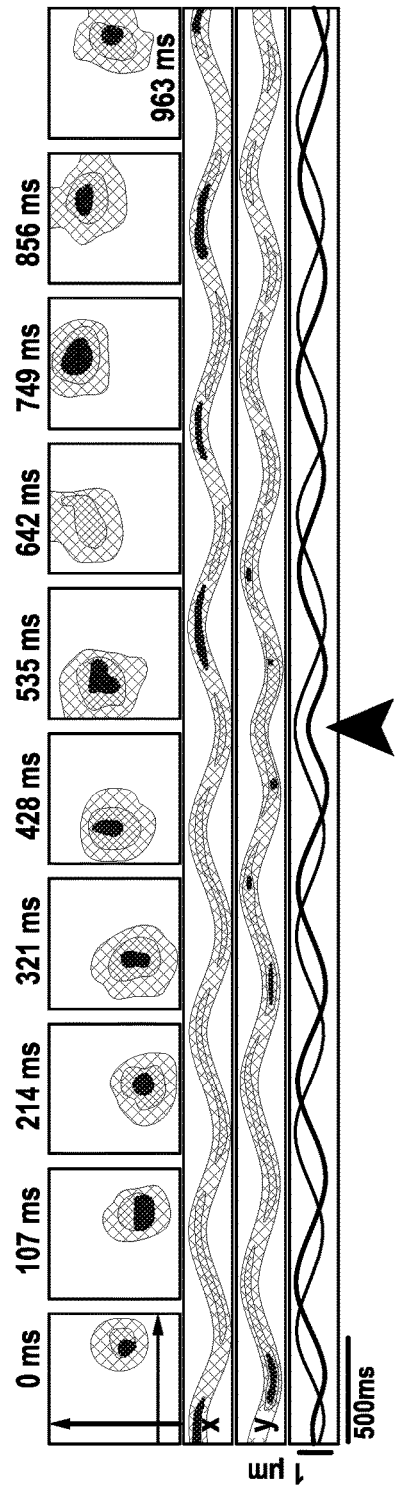

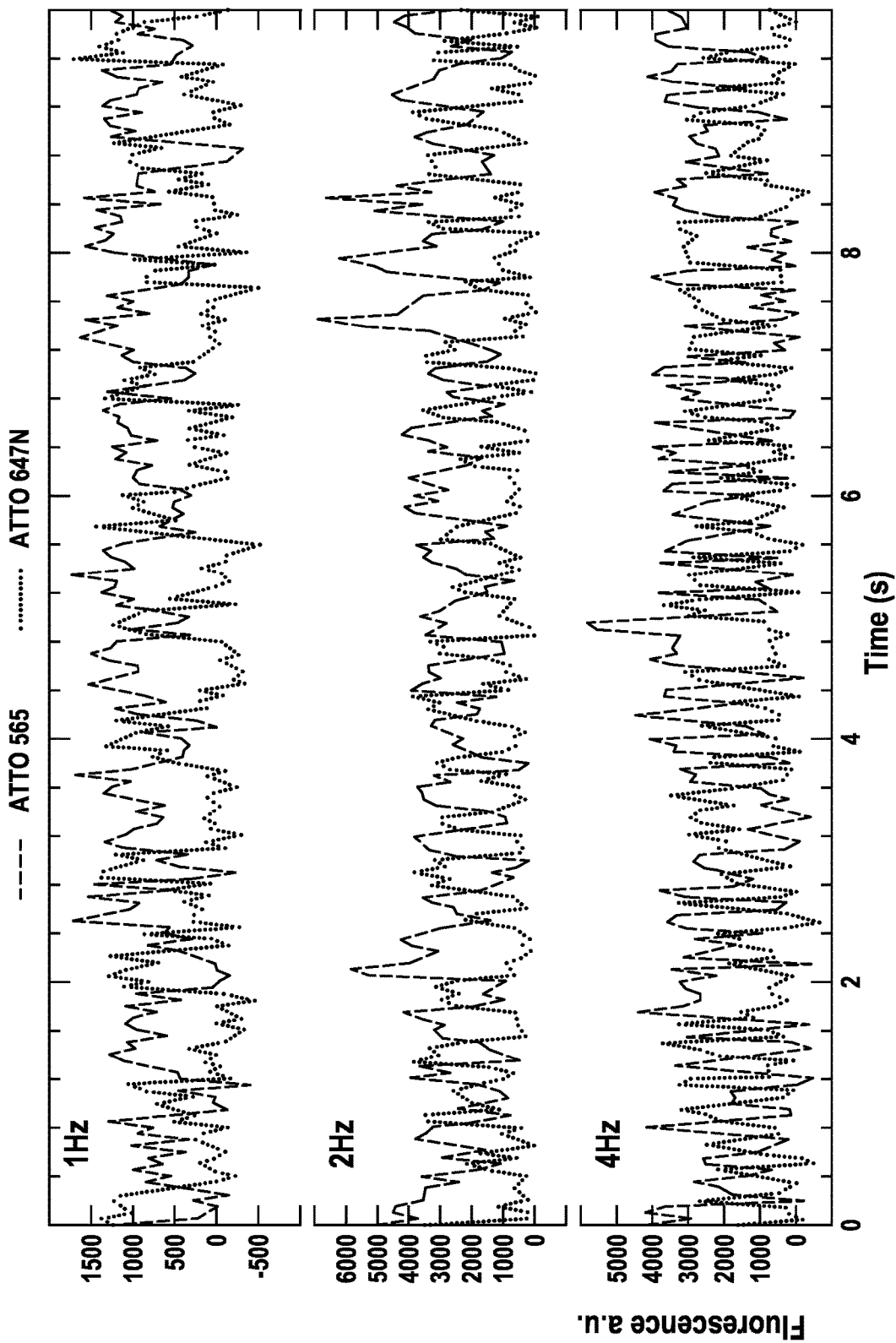

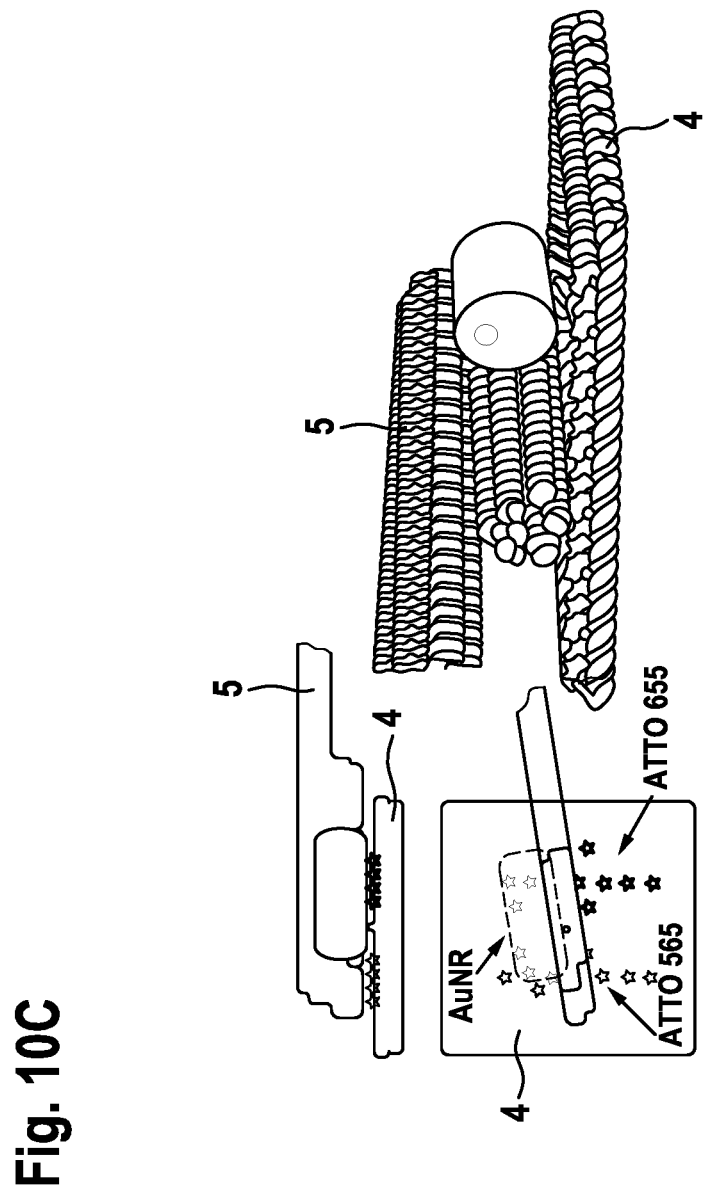

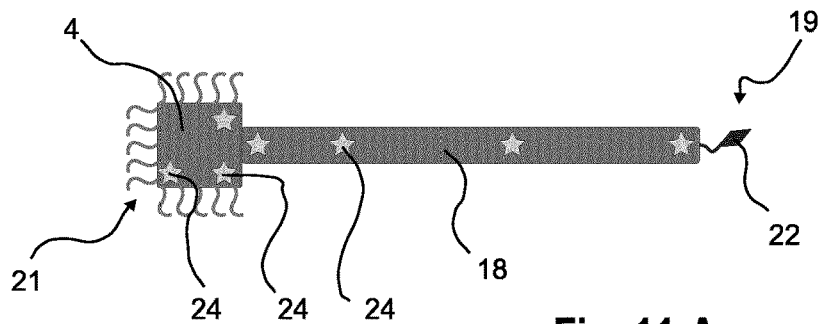
Fig. 11-A
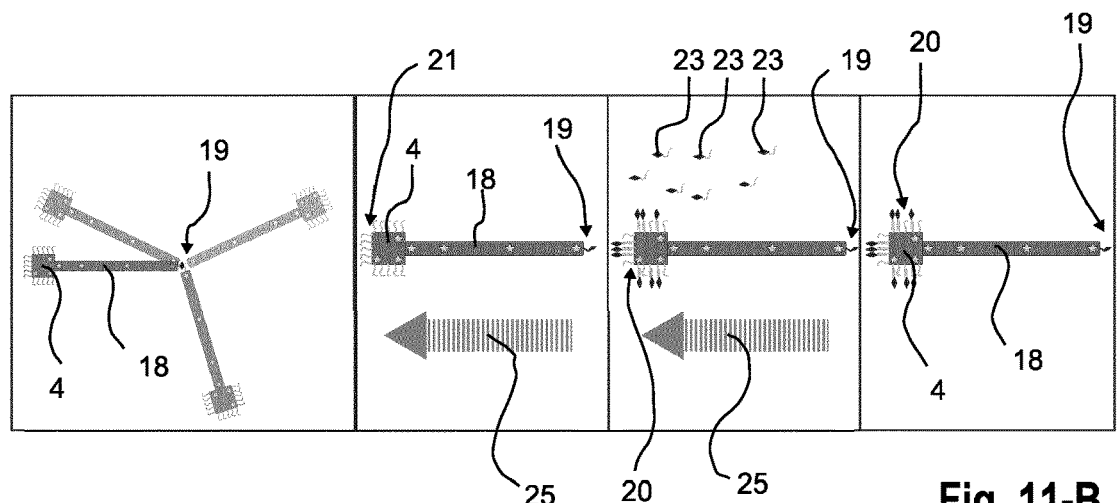
Fig. 11-B
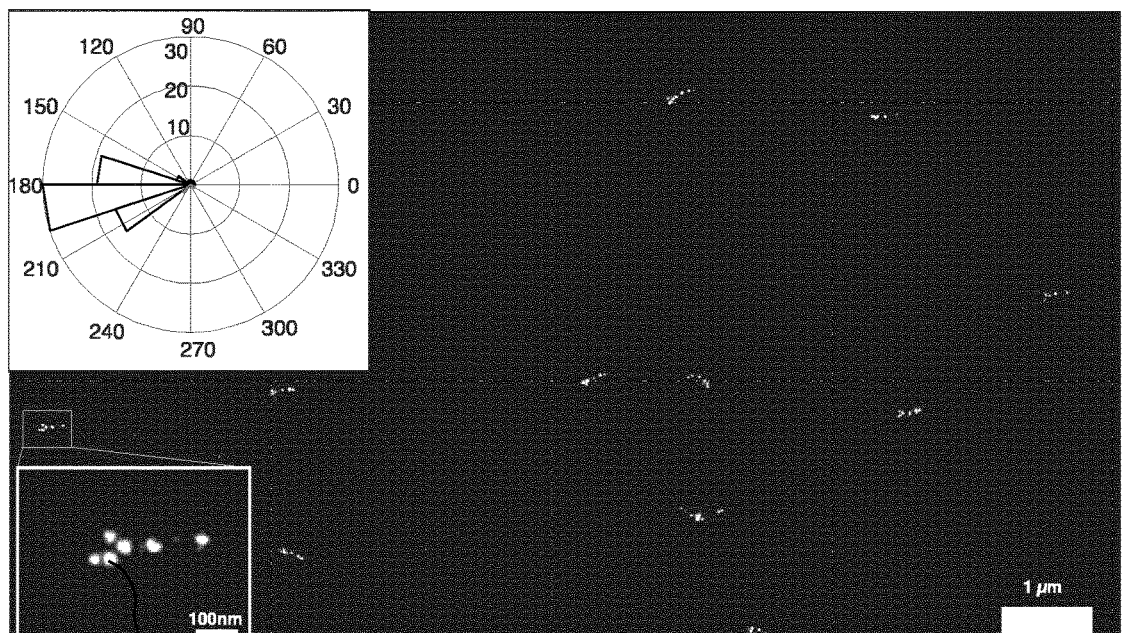
Fig. 11-C

SEQUENCE LISTING

<160> NUMBER OF SEQ ID NOS: 2

<210> SEQ ID NO 1
<211> LENGTH: 7704
<212> TYPE: DNA

<213> ORGANISM: Artificial Sequence
<220> FEATURE:
<223> OTHER INFORMATION: p7704 scaffold permutation

<400> SEQUENCE: 1

```
aagcttggca ctggccgtcg ttttacaacg tcgtgactgg gaaaaccctg gcgttaccca      60
acttaatcgc cttgcagcac atcccccttt cgccagctgg cgtaatagcg aagaggcccg     120
caccgatcgc ccttcccaac agttgcgcag cctgaatggc gaatggcgct ttgcctggtt     180
tccggcacca gaagcggtgc cggaaagctg gctggagtgc gatcttcctg aggccgatac     240
tgtcgtcgtc ccctcaaact ggcagatgca cggttacgat gcgcccatct acaccaacgt     300
gacctatccc attacggtca atccgccgtt tgttcccacg gagaatccga cgggttgtta     360
ctcgctcaca tttaatgttg atgaaagctg gctacaggaa ggccagacgc gaattatttt     420
tgatggcgtt cctattggtt aaaaaatgag ctgatttaac aaaaatttaa tgcgaatttt     480
aacaaaatat taacgtttac aatttaaata tttgcttata caatcttcct gtttttgggg     540
cttttctgat tatcaaccgg ggtacatatg attgacatgc tagttttacg attaccgttc     600
atcgattctc ttgtttgctc cagactctca ggcaatgacc tgatagcctt tgtagatctc     660
tcaaaaatag ctaccctctc cggcattaat ttatcagcta gaacggttga atatcatatt     720
gatggtgatt tgactgtctc cggcctttct cacccttttg aatctttacc tacacattac     780
tcaggcattg catttaaaat atatgagggt tctaaaaatt tttatccttg cgttgaaata     840
aaggcttctc ccgcaaaagt attacagggt cataatgttt ttggtacaac cgatttagct     900
ttatgctctg aggctttatt gcttaatttt gctaattctt tgccttgcct gtatgattta     960
ttggatgtta atgctactac tattagtaga attgatgcca ccttttcagc tcgcgcccca    1020
aatgaaaata tagctaaaca ggttattgac catttgcgaa atgtatctaa tggtcaaact    1080
aaatctactc gttcgcagaa ttgggaatca actgttatat ggaatgaaac ttccagacac    1140
cgtactttag ttgcatattt aaaacatgtt gagctacagc attatattca gcaattaagc    1200
tctaagccat ccgcaaaaat gacctcttat caaaaggagc aattaaaggt actctctaat    1260
cctgacctgt tggagtttgc ttccggtctg gttcgctttg aagctcgaat taaaacgcga    1320
tatttgaagt ctttcgggct tcctcttaat ctttttgatg caatccgctt tgcttctgac    1380
tataatagtc agggtaaaga cctgattttt gatttatggt cattctcgtt ttctgaactg    1440
tttaaagcat ttgagggga ttcaatgaat atttatgacg attccgcagt attggacgct    1500
atccagtcta acattttac tattacccc tctggcaaaa cttcttttgc aaaagcctct    1560
cgctattttg gttttatcg tcgtctggta acgagggtt atgatagtgt tgctcttact    1620
atgcctcgta attccttttg gcgttatgta tctgcattag ttgaatgtgg tattcctaaa    1680
tctcaactga tgaatctttc tacctgtaat aatgttgttc cgttagttcg ttttattaac    1740
gtagatttt cttcccaacg tcctgactgg tataatgagc cagttcttaa aatcgcataa    1800
ggtaattcac aatgattaaa gttgaaatta accatctca agcccaattt actactcgtt    1860
ctggtgtttc tcgtcagggc aagccttatt cactgaatga gcagctttgt tacgttgatt    1920
tgggtaatga atatccggtt cttgtcaaga ttactcttga tgaaggtcag ccagcctatg    1980
cgcctggtct gtacaccgtt catctgtcct ctttcaaagt tggtcagttc ggttccctta    2040
tgattgaccg tctgcgcctc gttccggcta agtaacatgg agcaggtcgc ggatttcgac    2100
acaatttatc aggcgatgat acaaatctcc gttgtacttt gtttcgcgct tggtataatc    2160
gctggggtc aaagatgagt gttttagtgt attcttttgc ctctttcgtt ttaggttggt    2220
```

```
gccttcgtag tggcattacg tattttaccc gtttaatgga aacttcctca tgaaaaagtc   2280
tttagtcctc aaagcctctg tagccgttgc taccctcgtt ccgatgctgt ctttcgctgc   2340
tgagggtgac gatcccgcaa aagcggcctt taactccctg caagcctcag cgaccgaata   2400
tatcggttat gcgtgggcga tggttgttgt cattgtcggc gcaactatcg gtatcaagct   2460
gtttaagaaa ttcacctcga aagcaagctg ataaaccgat acaattaaag gctccttttg   2520
gagccttttt tttggagatt ttcaacgtga aaaaattatt attcgcaatt cctttagttg   2580
ttcctttcta ttctcactcc gctgaaactg ttgaaagttg tttagcaaaa tcccatacag   2640
aaaattcatt tactaacgtc tggaaagacg acaaaacttt agatcgttac gctaactatg   2700
agggctgtct gtggaatgct acaggcgttg tagtttgtac tggtgacgaa actcagtgtt   2760
acggtacatg ggttcctatt gggcttgcta tccctgaaaa tgagggtggt ggctctgagg   2820
gtggcggttc tgagggtggc ggttctgagg gtggcggtac taaacctcct gagtacggtg   2880
atacacctat tccgggctat acttatatca accctctcga cggcacttat ccgcctggta   2940
ctgagcaaaa ccccgctaat cctaatcctt ctcttgagga gtctcagcct cttaatactt   3000
tcatgtttca gaataatagg ttccgaaata ggcaggggc attaactgtt tatacgggca   3060
ctgttactca aggcactgac cccgttaaaa cttattacca gtacactcct gtatcatcaa   3120
aagccatgta tgacgcttac tggaacggta aattcagaga ctgcgctttc cattctggct   3180
ttaatgagga tttatttgtt tgtgaatatc aaggccaatc gtctgacctg cctcaacctc   3240
ctgtcaatgc tggcggcggc tctggtggtg gttctggtgg cggctctgag ggtggtggct   3300
ctgagggtgg cggttctgag ggtggcggct ctgagggagg cggttccggt ggtggctctg   3360
gttccggtga ttttgattat gaaaagatgg caaacgctaa taaggggct atgaccgaaa   3420 atgccgatga aaacgcgcta cagtctgacg ctaaaggcaa acttgattct gtcgctactg   3480
attacggtgc tgctatcgat ggtttcattg gtgacgtttc cggccttgct aatggtaatg   3540
gtgctactgg tgattttgct ggctctaatt cccaaatggc tcaagtcggt gacggtgata   3600
attcaccttt aatgaataat ttccgtcaat atttaccttc cctccctcaa tcggttgaat   3660
gtcgcccttt tgtctttggc gctggtaaac catatgaatt ttctattgat tgtgacaaaa   3720
taaacttatt ccgtggtgtc tttgcgtttc ttttatatgt tgccaccttt atgtatgtat   3780
tttctacgtt tgctaacata ctgcgtaata aggagtctta atcatgccag ttcttttggg   3840
tattccgtta ttattgcgtt tcctcggttt ccttctggta actttgttcg gctatctgct   3900
tacttttctt aaaaagggct tcggtaagat agctattgct atttcattgt tcttgctct   3960 tattattggg cttaactcaa ttcttgtggg ttatctctct gatattagcg ctcaattacc   4020
ctctgacttt gttcagggtg ttcagttaat ctcccgtct aatgcgcttc ctgttttta   4080 tgttattctc tctgtaaagg ctgctatttt cattttgac gttaaacaaa aaatcgtttc   4140
ttatttggat tgggataaat aatatggctg tttattttgt aactggcaaa ttaggctctg   4200
gaaagacgct cgttagcgtt ggtaagattc aggataaaat tgtagctggg tgcaaaatag   4260
caactaatct tgatttaagg cttcaaaacc tcccgcaagt cgggaggttc gctaaaacgc   4320
ctcgcgttct tagaataccg gataagcctt ctatatctga tttgcttgct attgggcgcg   4380
gtaatgattc ctacgatgaa aataaaaacg gcttgcttgt tctcgatgag tgcggtactt   4440
ggtttaatac ccgttcttgg aatgataagg aaagacagcc gattattgat tggtttctac   4500
atgctcgtaa attaggatgg gatattattt ttccttgttca ggacttatct attgttgata   4560
```

```
aacaggcgcg ttctgcatta gctgaacatg ttgtttattg tcgtcgtctg gacagaatta    4620
ctttaccttt tgtcggtact ttatattctc ttattactgg ctcgaaaatg cctctgccta    4680
aattacatgt tggcgttgtt aaatatggcg attctcaatt aagccctact gttgagcgtt    4740
ggctttatac tggtaagaat ttgtataacg catatgatac taaacaggct ttttctagta    4800
attatgattc cggtgtttat tcttatttaa cgccttattt atcacacggt cggtatttca    4860
aaccattaaa tttaggtcag aagatgaaat taactaaaat atatttgaaa aagttttctc    4920
gcgttctttg tcttgcgatt ggatttgcat cagcatttac atatagttat ataacccaac    4980
ctaagccgga ggttaaaaag gtagtctctc agacctatga ttttgataaa ttcactattg    5040
actcttctca gcgtcttaat ctaagctatc gctatgtttt caaggattct aagggaaaat    5100
taattaatag cgacgattta cagaagcaag gttattcact cacatatatt gatttatgta    5160
ctgtttccat taaaaaaggt aattcaaatg aaattgttaa atgtaattaa ttttgttttc    5220
ttgatgtttg tttcatcatc ttcttttgct caggtaattg aaatgaataa ttcgcctctg    5280
cgcgattttg taacttggta ttcaaagcaa tcaggcgaat ccgttattgt ttctcccgat    5340
gtaaaaggta ctgttactgt atattcatct gacgttaaac ctgaaaatct acgcaatttc    5400
tttatttctg ttttacgtgc aaataatttt gatatgtag gttctaaccc ttccattatt    5460
cagaagtata atccaaacaa tcaggattat attgatgaat tgccatcatc tgataatcag    5520
gaatatgatg ataattccgc tccttctggt ggtttctttg ttccgcaaaa tgataatgtt    5580
actcaaactt ttaaaattaa taacgttcgg gcaaaggatt taatacgagt tgtcgaattg    5640
tttgtaaagt ctaatacttc taaatcctca aatgtattat ctattgacgg ctctaatcta    5700
ttagttgtta gtgctcctaa agatatttta gataaccttc tcaattcct ttcaactgtt    5760 gatttgccaa ctgaccagat attgattgag gttttgatat tgaggttca gcaaggtgat    5820 gctttagatt tttcatttgc tgctggctct cagcgtggca ctgttgcagg cggtgttaat    5880
actgaccgcc tcacctctgt tttatcttct gctggtggtt cgttcggtat ttttaatggc    5940
gatgttttag ggctatcagt tcgcgcatta aagactaata gccattcaaa atattgtct    6000 gtgccacgta ttcttacgct ttcaggtcag aagggttcta tctctgttgg ccagaatgtc    6060
cctttattta ctggtcgtgt gactggtgaa tctgccaatg taaataatcc atttcagacg    6120
attgagcgtc aaaatgtagg tatttccatg agcgtttttc ctgttgcaat ggctggcggt    6180
aatattgttc tggatattac cagcaaggcc gatagtttga gttcttctac tcaggcaagt    6240
gatgttatta ctaatcaaag aagtattgct acaacggtta atttgcgtga tggacagact    6300
cttttactcg gtggcctcac tgattataaa aacacttctc aggattctgg cgtaccgttc    6360
ctgtctaaaa tccctttaat cggcctcctg tttagctccc gctctgattc taacgaggaa    6420
agcacgttat acgtgctcgt caaagcaacc atagtacgcg ccctgtagcg cgcattaag    6480 cgcggcgggt gtggtggtta cgcgcagcgt gaccgctaca cttgccagcg ccctagcgcc    6540
cgctcctttc gctttcttcc cttcctttct cgccacgttc gccggctttc cccgtcaagc    6600
tctaaatcgg gggctccctt tagggttccg atttagtgct ttacggcacc tcgaccccaa    6660
aaaacttgat ttgggtgatg gttcacgtag tgggccatcg ccctgataga cggtttttcg    6720
ccctttgacg ttggagtcca cgttctttaa tagtggactc ttgttccaaa ctggaacaac    6780
actcaaccct atctcgggct attctttga tttataaggg attttgccga tttcggaacc    6840
accatcaaac aggattttcg cctgctgggg caaaccagcg tggaccgctt gctgcaactc    6900
tctcagggcc aggcggtgaa gggcaatcag ctgttgcccg tctcactggt gaaaagaaaa    6960
```

-continued

| | |
|---|---|
| accaccctgg cgcccaatac gcaaaccgcc tctccccgcg cgttggccga ttcattaatg | 7020 |
| cagctggcac gacaggtttc ccgactggaa agcgggcagt gagcgcaacg caattaatgt | 7080 |
| gagttagctc actcattagg caccccaggc tttacacttt atgcttccgg ctcgtatgtt | 7140 |
| gtgtggaatt gtgagcggat aacaatttca cacaggaaac agctatgacc atgattacga | 7200 |
| attcgagctc ggtacccggg gatcccgcct aaagagatag ggccgaccaa cgtcagacgc | 7260 |
| actcaatgtc acctggctgg gtttgtcagg tgtcgtgact ctgggcaaga ccggcaactg | 7320 |
| ctgttgttga gttccccatg gtcggtctca gtgggaactg cttccaactt ccgtctttat | 7380 |
| cgaggtaaca agcaccacgt agcttaagcc ctgtttactc attacaccaa ccaggaggtc | 7440 |
| agagttcgga gaaatgattt atgtgaaatg cgtcagccga ttcaaggccc ctatattcgt | 7500 |
| gcccaccgac gagttgctta cagatggcag ggccgcactg tcggtatcat agagtcactc | 7560 |
| cagggcgagc gtaaatagat tagaagcggg gttattttgg cgggacattg tcataaggtt | 7620 |
| gacaattcag cactaaggac acttaagtcg tgcgcatgaa ttcacaacca cttagaagaa | 7680 |
| catccaccct ggcttctcct gaga | 7704 |

<210> SEQ ID NO 2
<211> LENGTH: 7249
<212> TYPE: DNA
<213> ORGANISM: Artificial Sequence
<220> FEATURE:
<223> OTHER INFORMATION: p7249 scaffold permutation

<400> SEQUENCE: 2

| | |
|---|---|
| aagcttggca ctggccgtcg ttttacaacg tcgtgactgg gaaaaccctg gcgttaccca | 60 |
| acttaatcgc cttgcagcac atccccc ttt cgccagctgg cgtaatagcg aagaggcccg | 120 |
| caccgatcgc ccttcccaac agttgcgcag cctgaatggc gaatggcgct ttgcctggtt | 180 |
| tccggcacca gaagcggtgc cggaaagctg gctggagtgc gatcttcctg aggccgatac | 240 |
| tgtcgtcgtc ccctcaaact ggcagatgca cggttacgat gcgcccatct acaccaacgt | 300 |
| gacctatccc attacggtca atccgccgtt tgttcccacg gagaatccga cgggttgtta | 360 |
| ctcgctcaca tttaatgttg atgaaagctg gctacaggaa ggccagacgc gaattatttt | 420 |
| tgatggcgtt cctattggtt aaaaaatgag ctgatttaac aaaaatttaa tgcgaatttt | 480 |
| aacaaaatat taacgtttac aatttaaata tttgcttata caatcttcct gttttttgggg | 540 |
| cttttctgat tatcaaccgg gtacatatg attgacatgc tagttttacg attaccgttc | 600 |
| atcgattctc ttgtttgctc cagactctca ggcaatgacc tgatagcctt tgtagatctc | 660 |
| tcaaaaatag ctaccctctc cggcattaat ttatcagcta gaacggttga atatcatatt | 720 |
| gatggtgatt tgactgtctc cggcctttct cacccttttg aatctttacc tacacattac | 780 |
| tcaggcattg catttaaaat atatgagggt tctaaaaatt tttatccttg cgttgaaata | 840 |
| aaggcttctc ccgcaaaagt attacagggt cataatgttt ttggtacaac cgatttagct | 900 |
| ttatgctctg aggctttatt gcttaatttt gctaattctt tgccttgcct gtatgattta | 960 |
| ttggatgtta atgctactac tattagtaga attgatgcca ccttttcagc tcgcgcccca | 1020 |
| aatgaaaata tagctaaaca ggttattgac catttgcgaa atgtatctaa tggtcaaact | 1080 |
| aaatctactc gttcgcagaa ttgggaatca actgttatat ggaatgaaac ttccagacac | 1140 |
| cgtactttag ttgcatattt aaaacatgtt gagctacagc attatattca gcaattaagc | 1200 |
| tctaagccat ccgcaaaaat gacctcttat caaaaggagc aattaaaggt actctctaat | 1260 |

```
cctgacctgt tggagtttgc ttccggtctg gttcgctttg aagctcgaat taaaacgcga    1320
tatttgaagt ctttcgggct tcctcttaat cttttttgatg caatccgctt tgcttctgac   1380
tataatagtc agggtaaaga cctgattttt gatttatggt cattctcgtt ttctgaactg    1440
tttaaagcat ttgaggggga ttcaatgaat atttatgacg attccgcagt attggacgct    1500
atccagtcta acattttac tattaccccc tctggcaaaa cttcttttgc aaaagcctct     1560
cgctattttg gttttatcg tcgtctggta acgagggtt atgatagtgt tgctcttact      1620
atgcctcgta attcctttg gcgttatgta tctgcattag ttgaatgtgg tattcctaaa     1680
tctcaactga tgaatctttc tacctgtaat aatgttgttc cgttagttcg ttttattaac    1740 gtagatttt cttcccaacg tcctgactgg tataatgagc cagttcttaa aatcgcataa     1800
ggtaattcac aatgattaaa gttgaaatta accatctca agcccaattt actactcgtt    1860
ctggtgtttc tcgtcagggc aagccttatt cactgaatga gcagctttgt tacgttgatt    1920
tgggtaatga atatccggtt cttgtcaaga ttactcttga tgaaggtcag ccagcctatg   1980
cgcctggtct gtacaccgtt catctgtcct cttttcaaagt tggtcagttc ggttccctta  2040
tgattgaccg tctgcgcctc gttccggcta agtaacatgg agcaggtcgc ggatttcgac   2100
acaatttatc aggcgatgat acaaatctcc gttgtacttt gtttcgcgct tggtataatc   2160 gctggggtc aaagatgagt gttttagtgt attcttttgc ctctttcgtt ttaggttggt    2220
gccttcgtag tggcattacg tattttaccc gtttaatgga aacttcctca tgaaaaagtc   2280
tttagtcctc aaagcctctg tagccgttgc taccctcgtt ccgatgctgt ctttcgctgc   2340
tgagggtgac gatcccgcaa aagcggcctt taactccctg caagcctcag cgaccgaata   2400
tatcggttat gcgtgggcga tggttgttgt cattgtcggc gcaactatcg gtatcaagct   2460
gtttaagaaa ttcacctcga aagcaagctg ataaaccgat acaattaaag gctccttttg   2520
gagccttttt tttggagatt ttcaacgtga aaaaattatt attcgcaatt cctttagttg   2580
ttcctttcta ttctcactcc gctgaaactg ttgaaagttg tttagcaaaa tcccatacag   2640
aaaattcatt tactaacgtc tggaaagacg acaaaacttt agatcgttac gctaactatg   2700
agggctgtct gtggaatgct acaggcgttg tagtttgtac tggtgacgaa actcagtgtt   2760
acggtacatg ggttcctatt gggcttgcta tccctgaaaa tgagggtggt ggctctgagg   2820
gtggcggttc tgagggtggc ggttctgagg gtggcggtac taaacctcct gagtacggtg   2880
atacacctat tccgggctat acttatatca accctctcga cggcacttat ccgcctggta   2940
ctgagcaaaa ccccgctaat cctaatcctt ctcttgagga gtctcagcct cttaatactt   3000
tcatgtttca gaataatagg ttccgaaata ggcagggggc attaactgtt tatacgggca   3060
ctgttactca aggcactgac cccgttaaaa cttattacca gtacactcct gtatcatcaa   3120
aagccatgta tgacgcttac tggaacggta aattcagaga ctgcgctttc cattctggct   3180
ttaatgagga tttatttgtt tgtgaatatc aaggccaatc gtctgacctg cctcaacctc   3240
ctgtcaatgc tggcggcggc tctggtggtg gttctggtgg cggctctgag ggtggtggct   3300
ctgagggtgg cggttctgag ggtggcggct ctgagggagg cggttccggt ggtggctctg   3360
gttccggtga ttttgattat gaaaagatgg caaacgctaa taaggggct atgaccgaaa    3420 atgccgatga aaacgcgcta cagtctgacg ctaaaggcaa acttgattct gtcgctactg   3480
attacggtgc tgctatcgat ggtttcattg gtgacgtttc cggccttgct aatggtaatg   3540
gtgctactgg tgattttgct ggctctaatt cccaaatggc tcaagtcggt gacggtgata   3600
attcaccttt aatgaataat ttccgtcaat atttaccttc cctccctcaa tcggttgaat   3660
```

```
gtcgcccttt tgtctttggc gctggtaaac catatgaatt ttctattgat tgtgacaaaa   3720
taaacttatt ccgtggtgtc tttgcgtttc ttttatatgt tgccacctttt atgtatgtat   3780 tttctacgtt tgctaacata ctgcgtaata aggagtctta atcatgccag ttcttttggg   3840
tattccgtta ttattgcgtt tcctcggttt ccttctggta actttgttcg gctatctgct   3900
tacttttctt aaaaagggct tcggtaagat agctattgct atttcattgt ttcttgctct   3960
tattattggg cttaactcaa ttcttgtggg ttatctctct gatattagcg ctcaattacc   4020
ctctgacttt gttcagggtg ttcagttaat tctcccgtct aatgcgcttc cctgttttta   4080
tgttattctc tctgtaaagg ctgctatttt cattttttgac gttaaacaaa aaatcgtttc   4140
ttatttggat tgggataaat aatatggctg tttattttgt aactggcaaa ttaggctctg   4200
gaaagacgct cgttagcgtt ggtaagattc aggataaaat tgtagctggg tgcaaaatag   4260
caactaatct tgatttaagg cttcaaaacc tcccgcaagt cgggaggttc gctaaaacgc   4320
ctcgcgttct tagaataccg gataagcctt ctatatctga tttgcttgct attgggcgcg   4380
gtaatgattc ctacgatgaa aataaaaacg gcttgcttgt tctcgatgag tgcggtactt   4440
ggtttaatac ccgttcttgg aatgataagg aaagacagcc gattattgat tggtttctac   4500
atgctcgtaa attaggatgg gatattattt ttcttgttca ggacttatct attgttgata   4560
aacaggcgcg ttctgcatta gctgaacatg ttgtttattg tcgtcgtctg gacagaatta   4620 ctttacctttt tgtcggtact ttatattctc ttattactgg ctcgaaaatg cctctgccta   4680
aattacatgt tggcgttgtt aaatatggcg attctcaatt aagccctact gttgagcgtt   4740
ggctttatac tggtaagaat ttgtataacg catatgatac taaacaggct ttttctagta   4800
attatgattc cggtgtttat tcttatttaa cgccttattt atcacacggt cggtatttca   4860
aaccattaaa tttaggtcag aagatgaaat taactaaaat atatttgaaa aagttttctc   4920
gcgttctttg tcttgcgatt ggatttgcat cagcatttac atatagttat ataacccaac   4980
ctaagccgga ggttaaaaag gtagtctctc agacctatga ttttgataaa ttcactattg   5040
actcttctca gcgtcttaat ctaagctatc gctatgtttt caaggattct aagggaaaat   5100
taattaatag cgacgattta cagaagcaag gttattcact cacatatatt gatttatgta   5160
ctgtttccat taaaaaaggt aattcaaatg aaattgttaa atgtaattaa ttttgttttc   5220
ttgatgtttg tttcatcatc ttcttttgct caggtaattg aaatgaataa ttcgcctctg   5280
cgcgattttg taacttggta ttcaaagcaa tcaggcgaat ccgttattgt ttctcccgat   5340
gtaaaaggta ctgttactgt atattcatct gacgttaaac ctgaaaatct acgcaatttc   5400
tttatttctg ttttacgtgc aaataatttt gatatggtag ttctaacccc ttccattatt   5460
cagaagtata atccaaacaa tcaggattat attgatgaat tgccatcatc tgataatcag   5520
gaatatgatg ataattccgc tccttctggt ggtttctttg ttccgcaaaa tgataatgtt   5580
actcaaactt ttaaaattaa taacgttcgg gcaaaggatt taatacgagt tgtcgaattg   5640
tttgtaaagt ctaatacttc taaatcctca aatgtattat ctattgacgg ctctaatcta   5700
ttagttgtta gtgctcctaa agatatttta gataaccttc ctcaattcct ttcaactgtt   5760
gatttgccaa ctgaccagat attgattgag ggtttgatat tgaggttca gcaaggtgat   5820 gctttagatt tttcatttgc tgctggctct cagcgtggca ctgttgcagg cggtgttaat   5880
actgaccgcc tcacctctgt tttatcttct gctggtggtt cgttcggtat ttttaatggc   5940
gatgttttag ggctatcagt tcgcgcatta aagactaata gccattcaaa aatattgtct   6000
```

```
gtgccacgta ttcttacgct ttcaggtcag aagggttcta tctctgttgg ccagaatgtc    6060
ccttttatta ctggtcgtgt gactggtgaa tctgccaatg taaataatcc atttcagacg    6120
attgagcgtc aaaatgtagg tatttccatg agcgttttc  ctgttgcaat ggctggcggt    6180
aatattgttc tggatattac cagcaaggcc gatagtttga gttcttctac tcaggcaagt    6240
gatgttatta ctaatcaaag aagtattgct acaacggtta atttgcgtga tggacagact    6300
cttttactcg gtggcctcac tgattataaa aacacttctc aggattctgg cgtaccgttc    6360
ctgtctaaaa tcccttaat  cggcctcctg tttagctccc gctctgattc taacgaggaa    6420
agcacgttat acgtgctcgt caaagcaacc atagtacgcg ccctgtagcg gcgcattaag    6480
cgcggcgggt gtggtggtta cgcgcagcgt gaccgctaca cttgccagcg ccctagcgcc    6540
cgctcctttc gctttcttcc cttcctttct cgccacgttc gccggctttc cccgtcaagc    6600
tctaaatcgg gggctccctt tagggttccg atttagtgct ttacggcacc tcgaccccaa    6660
aaaacttgat ttgggtgatg gttcacgtag tgggccatcg ccctgataga cggttttcg    6720 cccttttgacg ttggagtcca cgttctttaa tagtggactc ttgttccaaa ctggaacaac    6780
actcaaccct atctcgggct attcttttga tttataaggg attttgccga tttcggaacc    6840
accatcaaac aggattttcg cctgctgggg caaaccagcg tggaccgctt gctgcaactc    6900
tctcagggcc aggcggtgaa gggcaatcag ctgttgcccg tctcactggt gaaaagaaaa    6960
accaccctgg cgcccaatac gcaaaccgcc tctccccgcg cgttggccga ttcattaatg    7020
cagctggcac gacaggtttc ccgactggaa agcgggcagt gagcgcaacg caattaatgt    7080
gagttagctc actcattagg caccccaggc tttacactt  atgcttccgg ctcgtatgtt    7140
gtgtggaatt gtgagcggat aacaatttca cacaggaaac agctatgacc atgattacga    7200
attcgagctc ggtacccggg gatcctctag agtcgacctg caggcatgc                7249
```

MOLECULAR MACHINE

The invention regards the field of nanotechnology and describes the utilization of electric fields for the manipulation of molecular mechanisms. In this way, a molecular machine is provided, which allows movement in response to said electrical fields.

In the past decades, several biomolecular mechanisms and machines have been demonstrated for the application in nanotechnology. However, none of them grew past the "proof of principle" phase.

Among the naturally occurring molecular machines mainly kinesin motors and microtubules were deployed, e.g., for the transport of nanoparticles (cf. prior art references 1 to 3). In so-called "in vitro motility assays" kinesin motors were fixed on lithographically patterned chip surfaces to transport microtubules through lithographically produced channel systems. Here electric manipulation was also used e.g. for the sorting of microtubules (cf. prior art reference 4).

In the past years, artificial biomolecular nanomachines were mainly produced on the basis of DNA molecules. The production of DNA machines utilizes the characteristic, sequence specific molecular interactions between DNA strands. Adequate choice of DNA sequences allows to "programmably" construct complex molecular structures from single DNA strands. A combination of relatively flexible single stranded DNA components with more rigid double stranded elements allows the construction of molecular mechanisms in which molecular components can be moved relative to each other. These include "DNA tweezers" as well as various "DNA walker" systems. An overview of such systems is given in prior art reference 5. With the recent development of the so-called "DNA origami method" it has become much easier to construct larger molecular systems (typically on the length scale of 10-100 nm). Recently this method was used to construct basic molecular machine elements, including several rotary joint and linear sliding structures (prior art references 6 to 9).

So far, the described molecular mechanisms have been actuated chemically or in some cases photo-chemically. In the case of chemical actuation, e.g., so-called DNA fuel strands were used to drive the movement of a mechanism through DNA strand hybridization reactions. Due to the slow kinetics of these reactions only very slow motion could be realized (prior art references 10 to 12). The same limitations apply to deoxyribozymes and DNA modifying enzymes (prior art reference 13).

Alternatively, motion of molecular mechanisms was achieved with a change of buffer conditions, e.g. by a change in pH or a change of the solution's ionic conditions. These methods come with the disadvantage that they unspecifically influence all system components and that buffer conditions are often not compatible with the chemistry of potential applications (e.g. enzymes are not functional in the specific conditions, nanoparticles can aggregate, etc.)

The aforementioned chemical methods typically require the external addition of solutions. In principle, this can be done with the help of microfluidic systems, which could allow a certain degree of automation. However, such an approach requires rather elaborate instruments and causes high material consumption.

At first glance, an attractive method for external control of nanomachines is based on photoswitchable molecules, typically derivatives of the photoswitchable molecule azobenzene (prior art references 14 to 16). Incorporation of such photoswitches into DNA double strands makes it possible to destabilize them upon light irradiation (in UV range) and stabilize them by irradiation with light of larger wavelength, and this procedure can be used to drive molecular mechanisms. The downside of this method, apart from the necessary chemical modification of the mechanisms, again is the slow and incomplete switching behavior.

Prior art reference 22 describes a biosensor including a gold platform. This biosensor allows only binary switching between an adhesive state and a non-adhesive state. No fine adjustment of the movement is possible. Prior art reference 23 describes the movement of molecular mechanisms in response to UV light.

None of the described approaches could ever demonstrate the exertion of a relevant force against an external load.

It is an object of the present invention to provide a molecular machine which allows quick reaction to control commands, which can generate high forces, and which can provide an exact movement.

The object is solved by the features of the independent claim. The dependent claims contain advantageous embodiments of the present invention.

The object is therefore solved by a molecular machine comprising a movement part and a control part. The movement part comprises several machine elements which are adapted to be moved with respect to each other. These machine parts are molecular structures, particularly nanomolecular structures. The movement part includes a first molecular element, a second molecular element and a linking element. The first molecular element and the second molecular element preferably are separate and/or independent elements. The linking element is adapted to constrain a relative movement of the first molecular element and the second molecular element while allowing a relative movement between the first molecular element and the second molecular element in at least one degree of freedom. Preferably, the first molecular element and the second molecular element can not be separated from each other and establish a moving mechanism with the linking element acting as bearing and/or joint.

In order to control the relative movement of the first molecular element and the second molecular element, the control part is configured to generate an electrical field around the movement part. Preferably, the control part includes an electrical device which applies said electrical field. The first molecular element is fixed relative to the control part such that the first molecular element is fixed relative to the electrical field generating means. Hence, even a change in the electrical field cannot cause a movement of the first molecular element. The first molecular element rather acts as a base for movement of the second molecular element. The second molecular element is therefore the only part which can be moved in response to the electrical field.

At least the second molecular element is electrically charged. The second molecular element can be an electrically charged molecule, particularly a biomolecule, or can be artificially electrically charged. In particular, an electrically charged functional group can be added to a molecular structure in order to create the electrically charged second molecular element. Due to the electrical charge, the second molecular element aligns to said electrical field. In case the electrical field is changed in orientation, the orientation of the second molecular element is also changed. This means that the control part can control fine adjustment of the second molecular element with respect to the first molecular element. The second molecular element can be transferred to and held in any orientation with respect to the first molecular element that is not prevented by the linking element. Additionally, a continuous movement of the second molecular element can be realized.

In summary, the movement part sets up the kinematics of the molecular machine, while the control part powers and controls any movement of said kinematics via electric actuation. Electric actuation solves several technical challenges that are currently faced by molecular nanomachines. In particular, electric actuation allows controlling molecular switches and mechanisms faster, with higher precision, and with less complex instrumentation compared to conventional methods. Moreover, the invention offers the solution to a central challenge of nanomanipulation (the "fat fingers" problem) since the externally controlled nanomanipulators are of the same small length scale as the manipulated nanoscale objects and molecules.

In a preferred embodiment, the control part comprises a fluidic channel. The movement part is provided in the fluidic channel. The control part further comprises an electrical device including electrodes. The electrodes are connected to the fluidic channel. In this way, the electrical field as described above can be created. The electrical device comprises a voltage source and electrical wiring to apply the voltage to the electrodes. Preferably, the electrical device comprises two electrodes for generating the electrical field. Alternatively, the voltage source can be a three-phase voltage source such that the electrical device has three electrodes. This allows providing a rotating electrical field such that the second molecular element can be rotated in a simple way.

Preferably, the control part comprises at least two electrical devices and fluidic channels with different orientations. In this way, two independent overlaying electrical fields can be created. The fluidic channels are arranged to intersect at an intersection area and the movement part is placed at the intersection area. Therefore, a two-dimensional movement of the second molecular element can be controlled. Alternatively, the above described three-phase voltage and the three electrodes might be used for two-dimensional movement control.

Favorably, the first molecular element is fixed to the fluidic channel. This means that the first molecular element can not move in response to the electrical field. The molecular element rather is a fixed base for the movement of the second molecular element. In this way, it is ensured that only the second molecular element can be moved. Further the fixation of the first molecular element allows very fine adjustment of the second molecular element, which aligns to the electrical field while the first molecular element does not move and/or align to the electrical field.

Providing the electrical device including electrodes might cause unwanted electrochemical effects. Particularly in case the movement part is employed for synthesis purposes, electrochemical effects to the synthesized products should be avoided. Therefore, the electrical device preferably includes an isolating element for isolating the electrodes from the movement part. The isolating elements particularly comprise membranes and/or gels and/or salt bridges. This means that only selected molecules can pass through the isolating elements such that the electrodes are separated from the movement part. However, the electrical field generated by the electrical devices is not influenced or at least not significantly influenced by the isolating element. Therefore, the control of movement of the second molecular element is not affected. The isolating element preferably also reduces the volume provided for reactions. This particularly allows holding the components of a desired reaction close to the movement part such that the components can manipulated and/or moved by the molecular machine.

The linking element is favorably part of the first molecular element or the second molecular element. Particularly, the first molecular element and/or the second molecular element might comprise a functional group which is adapted to link the first molecular element and the second molecular element. In this way, the manufacturing process of the molecular machine is simplified. Additionally, the linking element can be part of at least one of two or more mechanically interlocked molecules. This is particularly preferred in a case in which the movement part comprises rotaxanes. In such structures, the first molecular element comprises a linear part and the linking element and the second molecular element comprises a ring structure. The ring structure can rotate about the linear part and the linking element avoids the ring structure slipping off the linear part.

The first molecular element and/or the second molecular element and/or the linking element preferably are biomolecules. The biomolecules are particularly electrically charged. In a further preferred embodiment, the first molecular element and/or the second molecular element and/or the linking element are made of DNA (deoxyribonucleic acid), preferably DNA-origami, and/or RNA (ribonucleic acid) and/or protein and/or artificial charged supramolecular structures.

In a preferred embodiment, the first molecular element is a platform and the second molecular element is a positioning arm. The positioning arm is fixed to the platform via the linking element. The linking element constrains all relative movement of the first molecular element and the second molecular element except of a rotation of the second molecular element within a plane parallel to the first molecular element. Therefore, the positioning arm is preferably moved by aligning to two overlaid electrical fields. This allows adjusting the positioning arm in relation to the platform. Particularly, a full rotation of the positioning arm is possible, wherein the positioning arm can be stopped and hold in any position. Further, high forces are generated which allow manipulation of further molecules.

The first molecular element and/or the second molecular element are addressable. This means, that functional groups can be provided on the first molecular element and the second molecular element. Preferably, both, the first molecular element and the second molecular element can be addressed. Therefore, the movement part can be adapted to specific needs. This allows employing the molecular machine in various environments and/or for various purposes.

Preferably, fluctuations of the first molecular element and/or the second molecular element due to diffusion are within a tolerance of at most 10 nm, preferably at most 1 nm, particularly preferable at most 0.5 nm. Hence, a fine adjustment of the second molecular element is facilitated.

Preferably, any dimension of the first molecular element and the second molecular element is less than 1000 nm. Particularly, the above described platform is preferably made of square shape with a length of 50 to 55 nm. The positioning arm is preferably shorter than said length. Particularly, the positioning arm is adequately addressable within the overlap with the platform. Such dimensions allow manipulation of molecules with the molecular machine. Therefore, the molecular machine is a molecular nano-mechanism.

In a preferred embodiment, the linking element is made from a crossed two-layer scaffold routing. A top layer is preferably rotated with respect to a bottom layer by an angle between 80° and 100°, particularly 90°. Therefore, a stable base plate is generated.

The second molecular element is particularly made from a DNA six-helix bundle. Therefore, the second molecular element can be provided as positioning arm. This positioning arm might be used as robot arm for several purposes, for example for manipulating molecular mechanisms.

On the top layer of the first molecular element, the second molecular element forming the positioning arm is preferably connected to the plate via two adjacent scaffold crossovers with 3 and 4 unpaired bases, respectively. These short single-stranded segments create a flexible joint, which allows rotational movement of the second molecular element with respect to the first molecular element. While this joint cannot turn in the same direction indefinitely without winding up, it is still sufficiently flexible to allow the arm to reach any angle on the plate. This design is preferred over other potential designs for two reasons. First, this design allows us to use a one pot folding approach for the first molecular element and second molecular element, particularly the platform with the integrated 6HB arm, which confers the benefit of fast preparation and short experimental iteration periods. Second, a joint created by a double scaffold crossover provides higher resistance against external mechanical strain. For comparison, a single staple crossover would allow rotation around a single covalent bond, but the connection to the arm would always be oriented in a duplex unzipping geometry for one specific orientation of the arm during rotation. In this configuration, the connection to the first molecular element could potentially be unzipped, leading to the dissociation of the arm. By contrast, utilization of the scaffold strand (as in this work) to create the joint ensures a stable covalent connection between base plate and arm. With a circular scaffold strand, this strategy necessarily results in two single-stranded connections between arm and plate. For angles in which one strand is exposed to forces in unzipping geometry, the second strand is oppositely oriented in shear geometry and may therefore act as a strain relief. A linearized scaffold would allow for a covalent connection with only a single connecting strand, but would still be prone to unzipping when exposed to forces antiparallel to the direction of the scaffold strand in the plate next to its crossover to the arm structure. Particularly for experiments in which the length of the lever arm is exploited to create forces on the base plate (e.g. in the 20 bp unzipping experiment, FIGS. 9C and 9D), bearing forces of the same order are expected to act on the joint. In this case, a high mechanical stability of the joint is crucial and was therefore prioritized over the possibility of indefinite unidirectional rotation.

The second molecular element is preferably adapted to transport inorganic nanoparticles. Therefore, fast operations of biohybrid plasmonic systems are enabled.

A specific embodiment will be described together with the attached drawings.

Figure 1:
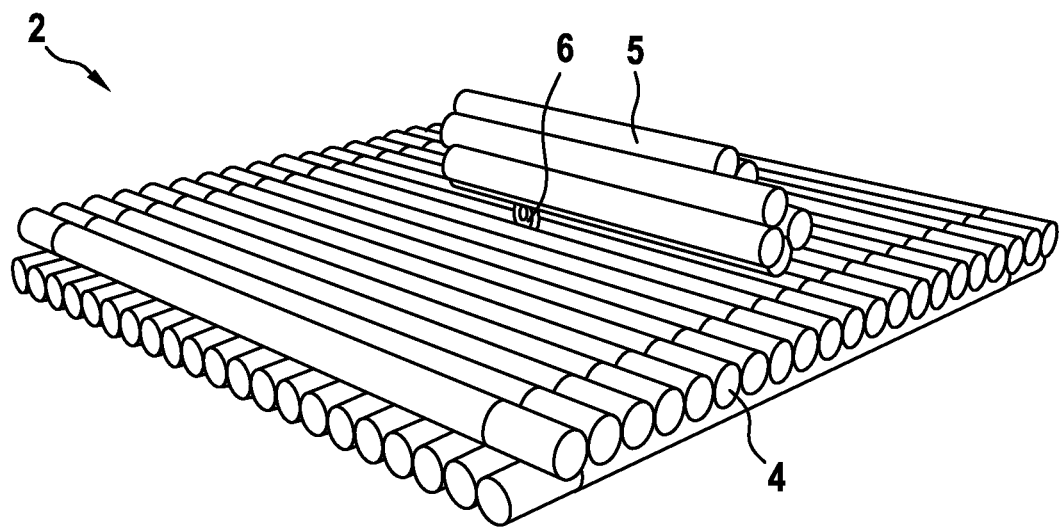
FIG. 1 is a schematic view of a moving part of a molecular machine according to an embodiment of the invention.

FIG. 7 shows stochastic switching experiments. (A) For single-molecule multi-color FRET experiments, a donor fluorophore (Alexa Fluor 488) is attached to the 6HB arm and two acceptor fluorophores (ATTO 565 and ATTO 647N) to staple strand extensions on opposite sides of the plate. The pictograms on the left show hybridization of an extended staple of the arm to the staple extension of the base plate labelled with ATTO 647N. The length of the docking duplex was varied between 8 and 10 bp. A schematic 3D representation is shown on the right. (B) Fluorescence traces obtained from the three fluorophores during donor excitation of the structures containing 9 bp docking duplexes. The change between green and red fluorescence indicates switching of the arm between corresponding docking sites. The zoom-in (bottom panel) reveals short periods of free diffusion between unbinding and rebinding events during which the donor (Alexa Fluor 488="blue") fluorescence is dominant. (C) Average dwell times for the bound and unbound states and their dependence on duplex length. Dwell times for the bound states (high acceptor signals-ATTO 647N="red" or ATTO 565="green", top panel) correspond to the times spent at the respective docking site. The dwell times for the unbound state (high donor signal-blue, bottom panel) represent the length of the traversal periods of the freely diffusing arm. (D) The average durations of the unbound states for various transitions and their dependence on duplex length. Based on start and end point of the traversal period (docking site or bound state-g or r before and after the unbound state), the unbound states can be classified as g→r and g→g or r→g and r→r traversals.

FIG. 8 shows external electric control of the robotic arm. (A) Two pointer extension designs for the robot arm and corresponding TEM images. The linear extension (left) pointer has a length of 411 nm (total length from center of rotation to tip: 436 nm). The pointer on the right has a shape complementary connection that withstands higher torque (total length of 354 nm, pivot point to tip: 332 nm). (B) Cross section and (C) top and isometric view of the cross-shaped electrophoretic sample chamber. (D) A schematic depiction of the experimental setup with four electrodes. (E) Fluorescence microscopic images of three structures that are switched in the electric field. For the highlighted particle, movements are shown as snapshots and kymographs. The two arrows indicate the axes chosen for the kymographs. Top: Switching left and right with 1 Hz. Bottom: Switching up and down with 1 Hz. (F) Top: One clockwise turn of 1 Hz rotation. Bottom: The kymographs show multiple turns of clockwise rotation followed by multiple counter-clockwise turns, separately for x and y axis and as an overlay. Reversal of the voltage and thus of the rotation direction is indicated by a red arrowhead. (G) Kymographs (x- and y-projection) obtained from a frequency sweep from 0 to 8 Hz and back, shown as an overlay of the kymograph along x-axis and y-axis. (H) High speed 360° clockwise and counter-clockwise rotation with 25 Hz. For each frame, the center of the pointer tip is indicated by a red cross. Reversal of the rotation direction is indicated by red arrowheads. Unlabeled scale bars: 1 µm.

FIG. 9 shows controlled hybridization and force-induced duplex dissociation. (A) Field-controlled switching of the extended robot arm between two 9 bp docking positions. Left: Scheme of the setup. Right: Single molecule localization image of pointer positions acquired during electrical rotation at 1 Hz. The number of localizations is increased at angles corresponding to the two docking positions. (B) Angle plotted over time for 1, 2, and 4 Hz rotation with 110V. The arm shows pronounced lagging for two angles (highlighted by grey bands), higher frequencies result in a larger number of missed turns, indicated by the red arrowheads. (C) Unzipping of a 20 bp DNA duplex with the extended robot arm. Extensions from the platform and from the arm feature a short 8 bp strain relief domain that prevents the staple strands from being pulled out of the structure. Experiments with two example particles are shown. Without electric field, the arm is fixed at one of two docking positions on the base plate. (D) Rotation requires unzipping of the duplex, which is shown in the images (before rotation, during rotation and after rotation) and kymographs at the bottom. Particle #1 rebinds to the starting position, whereas particle #2 rebinds to the position on the opposite side.

FIG. 10 shows electrically controlled movement of molecules and nanoparticles. (A) Configuration of the robot arm with shape complementary extension for transport of the FRET donor Alexa Fluor 488 between two 9 nt docking sites with the acceptors ATTO 565 and ATTO 647N. (B) Acceptor signals for continuous donor excitation for electrical rotation at 1 Hz (top), 2 Hz (middle) and 4 Hz (bottom). (C) For application of the robot arm in switchable plasmonics, a gold nanorod (AuNR) with 25 nm length is attached to the side of the 6HB arm and 11 ATTO 565 and ATTO 655 dyes are placed on opposite halves of the platform. (D) TEM micrograph of structure with a 25 nm AuNR and fluorescence traces for continuous excitation of the dyes while the robot arm is rotated at 1 Hz, 2 Hz and 4 Hz.

FIG. 11 is a schematic overview of fixing the platform of the molecular machine according to the embodiment of the invention.

DESCRIPTION OF THE EMBODIMENT

FIG. 1 is a schematic view of a movement part 2 of a molecular machine 1 according to an embodiment of the invention. In the embodiment, the movement part 2 comprises a platform 4, which corresponds to the first molecular element. On the platform 4, a position arm 5 is mounted, which corresponds to the second molecular element. A linking element 6 constrains the relative movement between platform 4 and positioning arm 5 such that the only possible relative movement is a rotation of the positioning arm 5 in a plane parallel to the platform 4.

Platform 4 and positioning arm 5 are constructed with the DNA origami method. The DNA origami method is well-known in the art and is for example described in prior art references 17 to 18. The square platform 4 consists of two layers of DNA double helices. In all figures, each double helix is represented by a cylinder. The positioning arm 5 is a six helix bundle. The linking element 7 comprises two DNA strands and connects the positioning arm 5 to the platform 4. Transmission electron microscopy micrographs can show the structure and quality of these objects.

The platform 4 and the positioning arm 5 can be built from different molecules e.g. RNA, proteins, artificial charged supramolecular structures. The positioning arm 5 might be elongated by coupling to further structures. An example for such elongation is described with respect to FIG. 4.

DNA molecules and thus also DNA origami structures are heavily charged biomolecules that can be electrically or electrophoretically manipulated. This fact can be exploited to achieve control and movement of molecular mechanisms.

Figure 2:
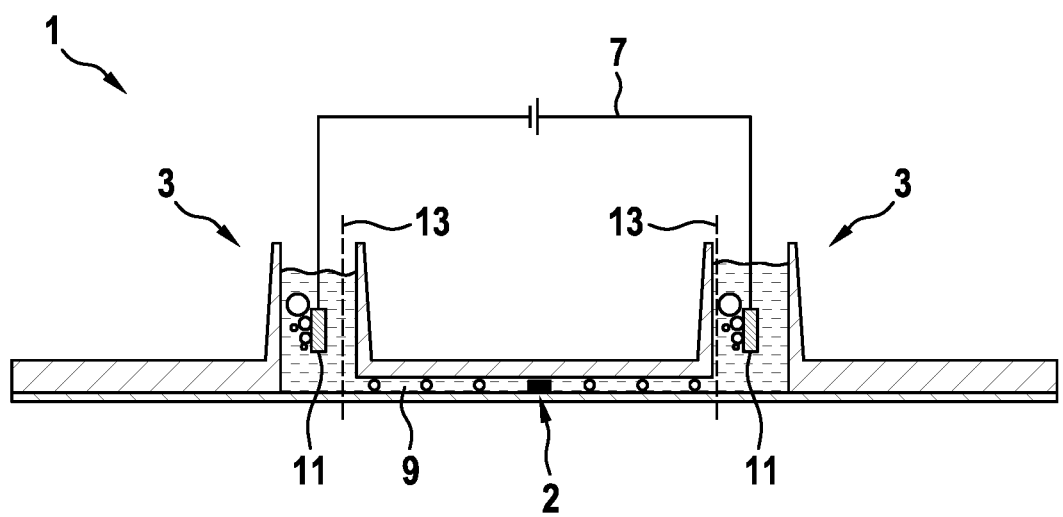
FIG. 2 is a schematic view of a first alternative of a control part of the molecular machine according to the embodiment of the invention.
Figure 3:
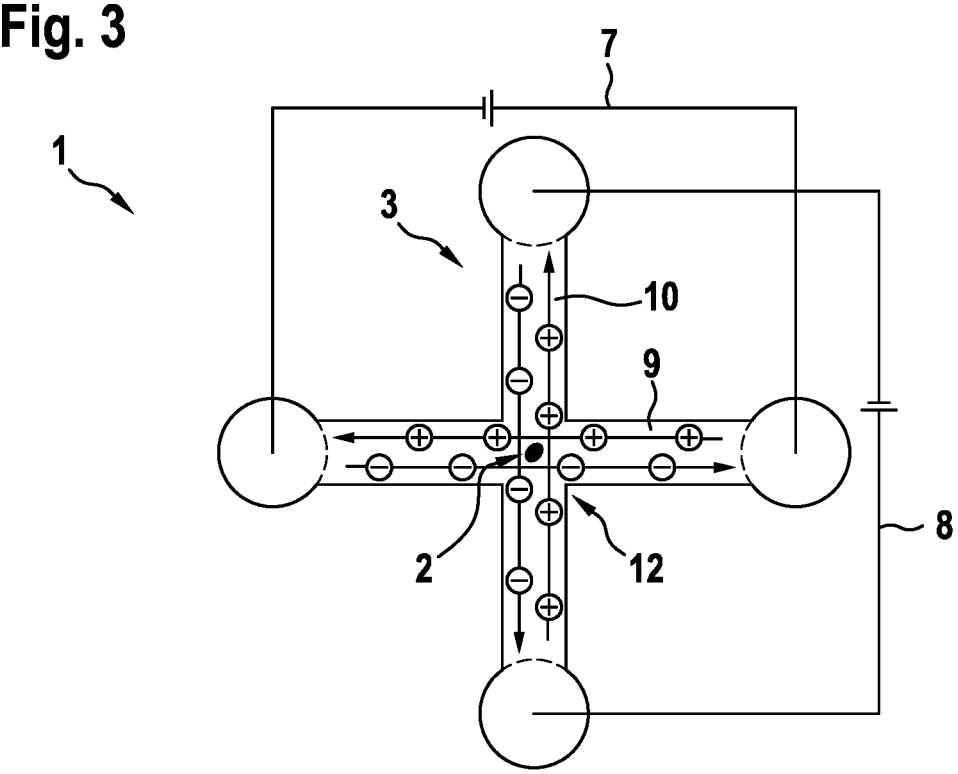
FIG. 3 is a schematic view of a second alternative of a control part of the molecular machine according to the embodiment of the invention.

Electric fields can be created in a simple electrophoretic or micro-electrophoretic setup. In the embodiment, a control part 3 is employed, which is shown in FIGS. 2 and 3. FIG. 2 is a schematic view of the molecular machine 1 including a control part 3 according to a first alternative, while FIG. 3 is a schematic view of the molecular machine including a control part 3 according to a second alternative.

As shown in FIG. 2, a fluidic channel 9 is provided which is contacted by platinum electrodes 11 of an electrical device 7. The movement part 2 is placed in the center of this fluidic channel 7, preferably as far away from the electrodes as possible. Isolating elements 13 might be provided in order to isolate the electrodes 13 from the movement part 2. The Isolating elements 13 preferably comprise membranes, gels or salt bridges. The isolating elements 13 do not allow transfer of selected molecules such that the electrodes are separated form the movement part 2 such that no unwanted traveling of elements from the movement part 2 to the electrodes 11 can take place. This avoids unwanted electrochemical influences of the electrodes 11.

Electric control is achieved by applying voltages to the electrodes. For that purpose, low control voltages as output channels of a DAQ board (data acquisition board) are amplified to adequate voltages by an operational amplifier. In the embodiments, the electrical device 7 applies voltages of up to 200 V.

Two-dimensional movement of the positioning arm 5 can be realized with a crossed channel geometry. This is shown in FIG. 3. The control part 3 comprises a first electrical device 7 and a second electrical device 8, both are identical to the above described electrical device of FIG. 2. The first electrical device 7 is connected to a first fluidic channel 9 and the second electrical device 9 is connected to a second fluidic channel 10, wherein the first fluidic channel 9 and second fluidic channel 10 are both identical as the above described fluidic channel of FIG. 2. The first fluidic channel 9 and the second fluidic channel 10 intersect at an intersection area 12 and are orientated perpendicular to each other. The movement part 2 is placed in the intersection area 12. Due to such a design, the electrical fields of the first electrical device 7 and the second electrical device 8 are superposed. Superposition of electrical fields in the fluidic channels 9, 10 allows to adjust the positioning arm 5 in arbitrary angles or to rotate it in circles relative to the platform 4.

In order to ensure that only the positioning arm 5 rotates while the platform 4 remains still, the platform 4 is fixed to at least one of the fluidic channels 9, 10 of the control part 3. In this way, the platform is fixed relative to the control part 3 which means that no movement of the platform 4 is possible in response to the electrical field.

In an alternative setup, lithographically designed microelectrodes can be used, which require much smaller voltages for manipulation. In principle, this enables the miniaturization of the whole setup and the integration e.g. on a USB-Stick.

The electrically charged positioning arm 5 aligns to the electrical fields generated via the first electrical device 7 and the second electrical device 8. In this way, an exact positioning of the positioning arm 5 can be reached. Particularly, the positioning arm 5 can be moved with a tolerance of at most 1 nm.

Proof of Functionality

Evidence for the electro-controlled movement of positioning arms 5 can be provided in several ways.

Figure 4:
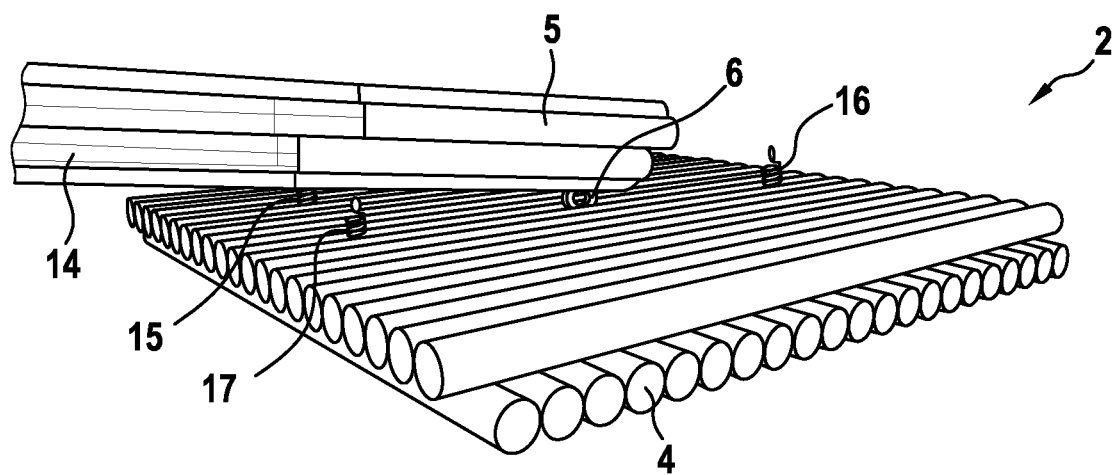
FIG. 4 is a schematic view of the moving part of the molecular machine according to the embodiment of the invention, which is modified for proof of functionality.

FIG. 4 is a sketch of the DNA platform 4 with the positioning arm 5 that is modified with a blue donor dye 15. The platform 4 was labeled at two positions with a green first acceptor dye 16 and red second acceptor dye 17, respectively. The positioning arm 5 movement can be proven via single molecule FRET (fluorescence resonance energy transfer). Further, for better electric coupling (via the DNA-structures charge) and to enable direct optical observation an additional lever/pointer structure 14 is provided to extend the positioning arm 5 to a length of several 100 nm (in this example ~400 nm).

The movement of the positioning arm can be characterized by means of single molecule fluorescence resonance energy transfer (smFRET), which demonstrates the system's positioning precision on the nanometer scale. As the blue donor dye 15, Alexa Fluor 488 is employed, as the green first acceptor dye 16, ATTO 565 is employed, and as the red second acceptor dye 17, ATTO 647N is employed. The blue donor dye 15 can excite the first acceptor dye 16 and second acceptor dye 17 via FRET if donor and acceptor are in closer proximity than the Foerster radius (~6 nm).

Figure 5:
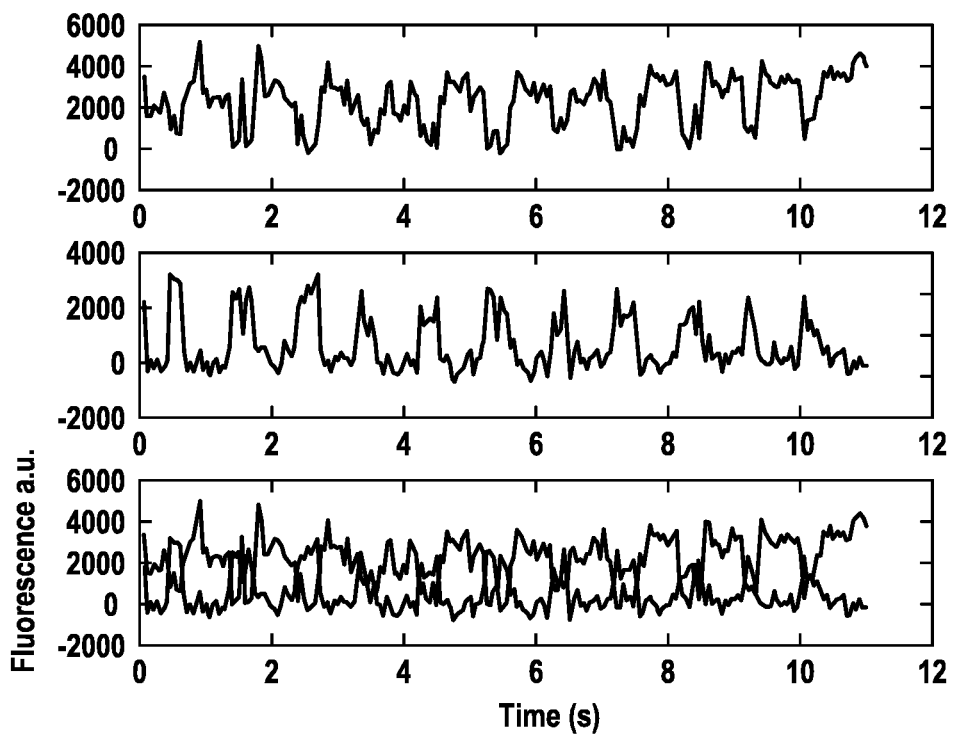
FIG. 5 is a schematic view of montage of single images from a microscope video showing the movement of the molecular machine according to the embodiment of the invention.

FIG. 5 illustrates single molecule FRET traces corresponding to the sketch in FIG. 4. The rotation of the positioning arm 5 is externally driven at 1 Hz while the donor dye 15 on the positioning arm 5 is being excited. This results in an alternating emission of green by the first acceptor dye 16, as shown in the top diagram of FIG. 5, and red by the second acceptor dye 17, as shown in the middle diagram of FIG. 5. An overlay of both traces, which is shown in the bottom diagram of FIG. 5, clearly shows the periodic alternating excitation.

Figure 6:
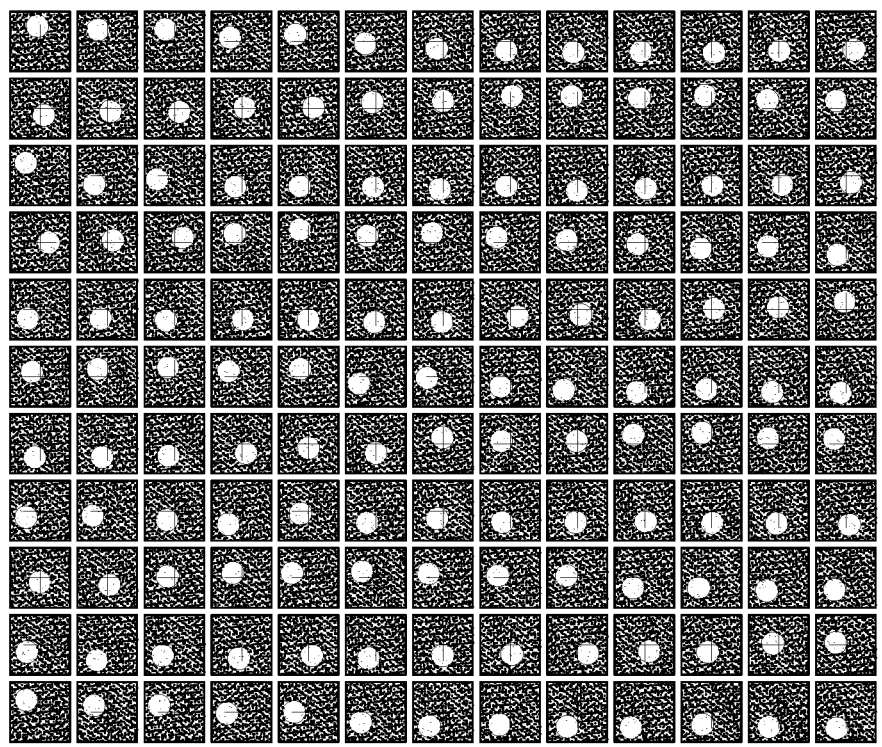
FIG. 6 is a schematic view of a diagram showing movement of the molecular machine according to the embodiment of the invention.

As shown in FIG. 6, the invention can provide a periodic movement of the positioning arm 5 from one position of the platform 4 to the other. This experiment also demonstrates the potential of the invention to transport and position molecules on the platform 4, which is of great importance for a wide range of applications.

An alternative way of proof of movement of the positioning arm 5 is shown in FIG. 6. FIG. 6 shows a montage of single images from a microscope video, which shows the electrically driven rotation of the positioning arm (exposure per frame: 50 ms, Scale bar: 500 nm). Fluorescent dyes are fixed to the tip of positioning arm 5. The origami platform 4 is located in the image center and is indicated by a cross. The particle rotates in an external field. For FIG. 6, fluorescent dyes have been placed on the tip of the extension of the positioning arm 5, i.e. on the additional lever/pointer structure 14. The positioning arm 5 is rotated in circles with a frequency of 1 Hz. As shown on the image series, the particle at the tip of the positioning arm is performing the desired rotational movement. This also shows the controlled movement of a nanoscale object on a length scale of 1 μm.

Industrial Application Perspectives

The key capability to position molecules precisely, fast and electrically controlled as well as the possibility to locally exert directed forces trough molecular mechanisms on the nanoscale enables a wide variety of application opportunities in nanotechnology. Below, three possible areas of application will be briefly discussed.

Single Molecule Sensing and Force Spectroscopy

Highly specific molecular interactions are responsible for a wide range of biological processes and are also the mechanism of action of pharmacological substances. For this reason, biological research has been focused on the precise biochemical and biophysical characterization of these interactions for quite some time. In biophysical research, the strength of interactions is often analyzed in single molecule experiments. Here special instruments are used to exert forces on the binding partners. This includes experiments with atomic force microscopes, optical tweezers and magnetic tweezers.

The movement part 2 of platform 4 and positioning arm 5 according to the described embodiment of the invention make it possible to apply forces to molecules in situ. That is to say, in the case of the invention, the force applying lever itself is a molecular structure. Contrary to the other methods mentioned, it is relatively simple to conjugate the molecules and binding partners that are to be characterized to the platform 4 and the positioning arm 5. The experimental setup used to create electric forces is much simpler. This enables highly parallelizable execution of force measurements of molecular interaction partners since a vast number of measuring platforms 4 can be actuated at the same time. The sensor principle can also be used for screening of molecule libraries by "barcoding" (cf. prior art reference 19) of single platforms 4.

DNA Templated Synthesis

In the past 15 years, DNA templated synthesis was established as a novel method to increase the efficiency of chemical reactions and for the sequence based production of molecule libraries. This approach exploits the highly increased local concentration of molecules that were conjugated to a DNA strand and are thereby colocalized by sequence specific base pairing on the template (cf. prior art references 20 and 21).

This principle can be transferred to reactions with electrically driven molecular mechanisms. Electrically addressable moving molecular mechanisms can bring molecules into close proximity to induce their reaction. In this way for example, the same reaction can be repeated depending on an external clocking signal or sequential reactions can be performed according to a programmable protocol. Contrary to existing "proof of principle" experiments, the possibility of repeated and highly parallelized performance of such reactions enable the production of technologically relevant amounts of substances. The invention, i.e. the development of the electrical switchable molecular machine 1, is therefore an enabling technology for the realization of genuine molecular robotic systems and molecular assembly lines.

Photonics/Plasmonics

The molecular actuators according to the invention can readily be modified with inorganic particles like e.g. metal or semiconductor particles. For instance, a change in position of the molecular mechanisms can vary the particles' orientation with respect to a polarized external field. Accordingly, the occurrence of plasmonic effects (e.g. field enhancement, energy transfer, heating effects) can be switched via electric control.

Summary

With the described invention, nanoscale objects or molecules can be controllably moved and positioned. As an embodiment and for the demonstration of the general working principle a molecular positioning arm 5 from DNA molecules was explained. The nanoscale molecular positioning arm 5 is fixated on a specifically addressable platform 4 with a flexible joint that allows rotation around the pivot point. The positioning arm 5 movement can be precisely controlled by external electric fields. The positioning arm 5 can transport molecules, control chemical processes and exert forces on other molecules "in situ". The method exploits the intrinsic electric charge of biomolecules and can be generally applied to synthetic as well as naturally occurring biomolecular mechanisms.

Further Aspects

In the molecular machine, sequence-specific switching is deliberately abandoned and electrical fields are used to move the components of a DNA machine with respect to each other. Thus many orders of magnitude in operation speed, almost perfect switching yield and the capability of computer-controlled nanoscale motion and positioning are gained.

The actuator unit of our system is comprised of a 55×55 nm$^2$ DNA origami plate (platform 4) with an integrated, 25 nm long arm (positioning arm 5) defined by a DNA six-helix bundle (6HB), allowing for a high-yield one-pot folding procedure. For the rigid DNA plate, a crossed two-layer scaffold routing is utilized, in which the top layer is rotated with respect to the bottom layer by 90°. The 6HB functioning as the robot arm is connected to the top-layer of the base plate via a flexible joint (linking element 6) created by three and four unpaired bases, respectively. Successful assembly of the structure with ≈90% yield was verified using transmission electron microscopy (TEM) and atomic force microscopy (AFM). Consistent with the design, AFM yields a height of 4 nm for the base plate and an additional 4 nm for the 6HB arm.

First, the diffusive motion of the arm with respect to the base plate is investigated using single-molecule multi-color Förster Resonance Energy Transfer (FRET) experiments. This is illustrated in FIG. 7. For these experiments, two staple strands on opposite sides of the plate were extended with an identical short docking sequence, while a staple strand on the arm was extended with the complementary sequence. Transient binding of the arm results in stochastic switching between the two docking sites, which we observed with the help of three reporter dyes—a FRET donor at the tip of the arm, and two different acceptor dyes at the docking sites (FIG. 7A). A typical trace of stochastically alternating FRET signals is shown in FIG. 7B. Upon donor excitation, a high donor (blue, solid line) fluorescence indicates a freely diffusing arm, while a high acceptor fluorescence (green, dashed line, or red, dotted line) indicates docking at the respective site. Dwell times for the three states were extracted from fluorescence traces of over 1000 robot arm platforms using a hidden Markov model (HMM) analysis. As expected, the dwell time in the bound states increases with docking duplex length (FIG. 7C, top panel). Interestingly, the dwell time spent in the unbound state also increases (FIG. 7C, bottom panel), indicating slower diffusion and/or a reduced hybridization rate for longer docking duplexes. Observed state transitions can be classified into transitions from one binding site to the other (green/red or red/green), or rebinding events to the same docking site (green/green, red/red). When the arm initially unbinds from the green docking site, it binds to either site with roughly the same transition time (FIG. 7D, top panel). Conversely, arms starting at the red docking site have a higher tendency to return to the same site (FIG. 7D, bottom panel). This bias is consistent with the expected orientation of the arm on the base plate, which is designed to point towards the red docking site. The corresponding higher effective concentration of the arm in the vicinity of the red docking site results in faster rebinding transitions. Photophysical origins of the observed changes in the FRET signal (such as fluorescent dark states or environmental quenching of the fluorophores) were excluded by performing alternating laser excitation experiments.

Figure 8A:
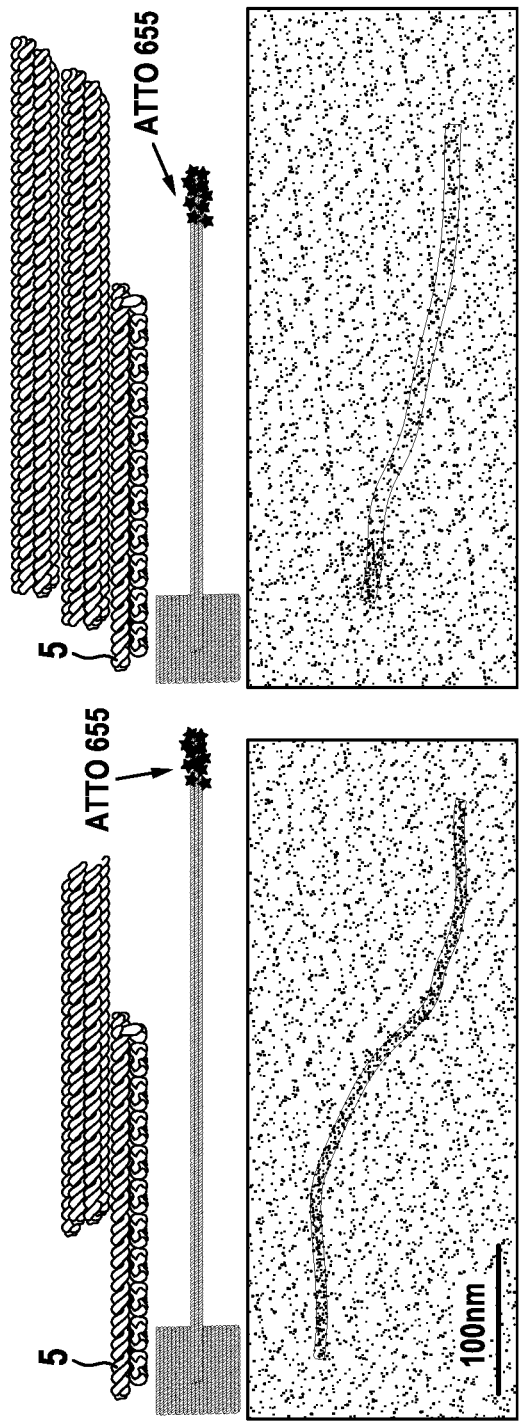

To facilitate direct observation of the arm's motion by diffraction-limited fluorescence microscopy, two versions of pointer structures were designed that were multiply labeled with the fluorophore ATTO 655. Version one extended the arm linearly by 411 nm (FIG. 8A left). Version two extended the arm by 308 nm (FIG. 8A, right) and was modularly plugged onto the robot arm using a shape-complementary connector structure, creating a more stable connection between pointer and arm to allow for better torque transmission. Both pointers are based on a rigid 6HB with a persistence length >1 µm (25). The two designs were motivated by the differing requirements for the experiments described below. For rotational diffusion experiments in the absence of docking sites, the linear pointer was found to interact less with the base plate than the shape-complementary pointer. However, when used to exert forces the linear pointer displayed a reduced stability and tended to break at the connection site. In the presence of docking sites, single molecule localization images of both pointers were consistent with the positions of the docks on the platform, proving that the extensions point along the axis of the short arm and that the interactions with the docking sites dominated over unspecific sticking.

Figure 8B:
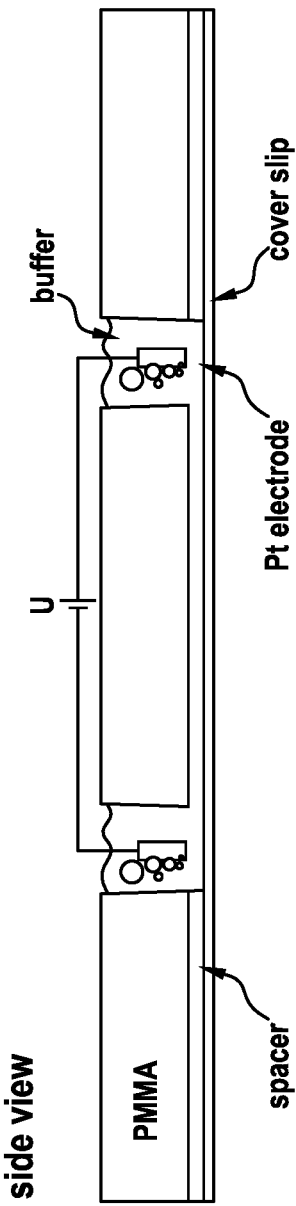
Figure 8G:
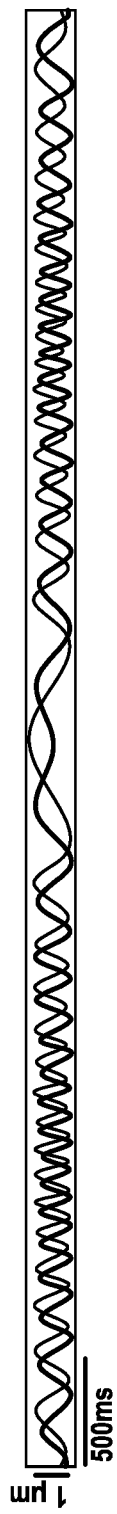

In order to realize dynamic external control of the robot arm, electrical fields were applied to the system—a natural choice for the manipulation of charged biomolecules. Electrical fields have been previously used only to stretch or orient substrate-immobilized DNA duplexes but not to dynamically control the conformation of nanomechanical DNA devices. We created a cross-shaped electrophoretic chamber constituted by two perpendicular fluidic channels intersecting at the center of a microscopy cover slip, with two pairs of platinum electrodes inserted into the four buffer reservoirs (FIGS. 8B & C). DNA nanostructures immobilized at the center of the cross chamber experience a superposition of the fields generated by the electrode pairs. Hence, a voltage can be applied to arbitrarily control the direction that the arm points (FIG. 8D).

Figure 8H:
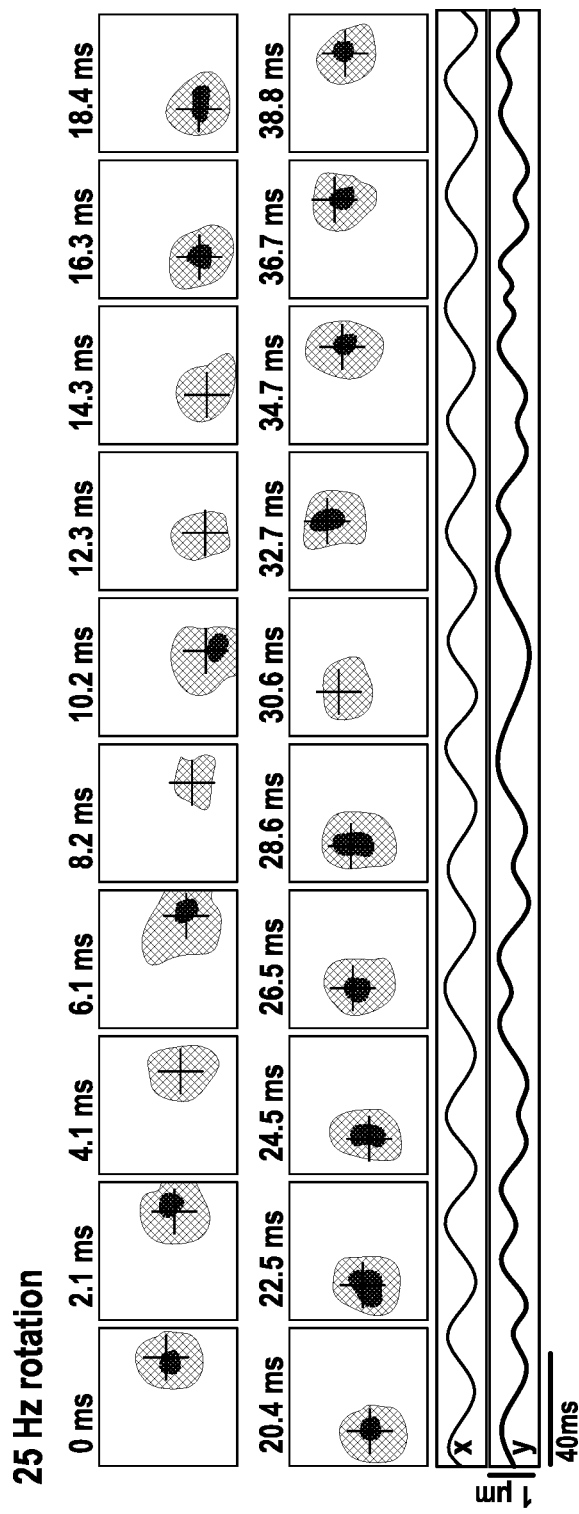

Electrical actuation of the arms results in a movement of the pointers, which were observed with an EMCCD camera using TIRF microscopy. In FIG. 8E, switching of an arm in two perpendicular directions is shown, rotation with a constant frequency of one Hertz (FIG. 8F) and with variable frequency (FIG. 8G), ramping from 0 to 8 Hz and back to 0 Hz. In order to characterize faster arm movements, TIRF microscopy videos with a 2 ms time resolution using a CMOS camera were recorded. An image series taken from a video in which the robot arm was rotated back and forth at f=25 Hz is shown in FIG. 8H. Kymographs displaying the projected motion of the arm's pointer along the x- and y-axis show the expected sinusoidal characteristics. In high-viscosity buffer solution containing 65% sucrose, motion of the arm was significantly slowed down.

Next, the angular positioning precision of the arm that can be achieved in the absence of docking sites by the electrical field alone is assessed. For large applied voltages (≥120 V in our setup) the angular standard deviation is ≈0.1 rad, which translates to a positioning precision of ≈2.5 nm on the plate.

Figure 9A:
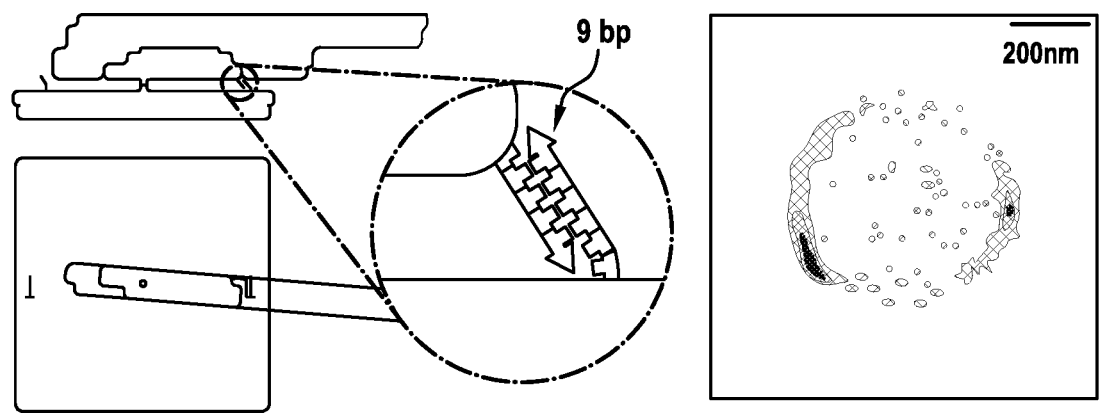
Figure 9B:
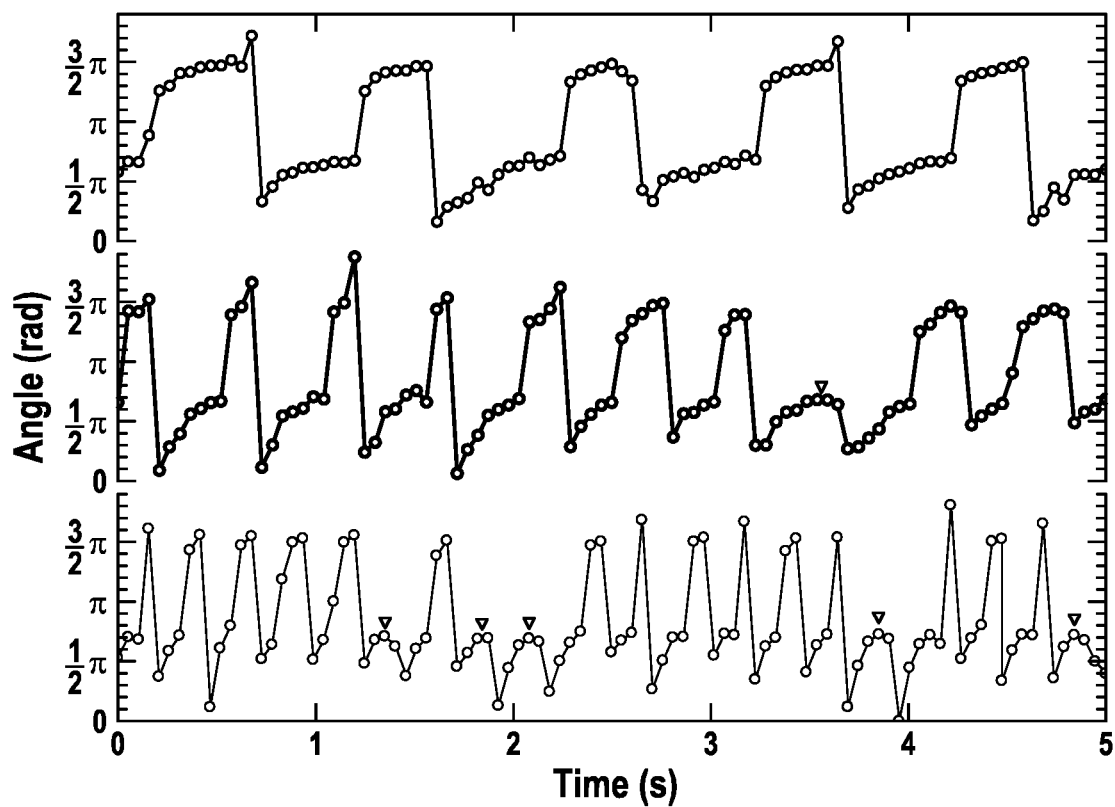

In order to investigate the interaction of the arm with binding sites on the platform during electrical manipulation, "latching experiments" were performed with the same arrangement of docks as in FIG. 7 and an identical 9 base pair (bp) docking sequence (FIG. 9A). When rotated at frequencies of f=1, 2, and 4 Hz temporary stalling of the pointer at the two angle positions that corresponded to the two docking sites were observed (FIG. 9B), indicating that the arm "snaps" into the binding positions during rotation.

Whereas the signal followed the external control faithfully for f=1 Hz, occasional "skips" occurred for f=2 Hz and 4 Hz. This behavior is caused by the statistical nature of single molecule duplex dissociation, whose frequency increases exponentially with the application of a force and, in dynamic experiments, also depends on the force rate. Apparently, the dissociation rate (~0.4 s−1, cf. FIG. 7B) of the docking duplex is sufficiently enhanced by the electrical force to follow the 1 Hz rotation. For higher frequencies, the duplex does not always dissociate fast enough and the arm cannot follow the rotation of the electrical field. By contrast, at a slower rotation speed of f=0.1 Hz, dynamic latching can be observed also to four different docking sites.

Figure 9C:
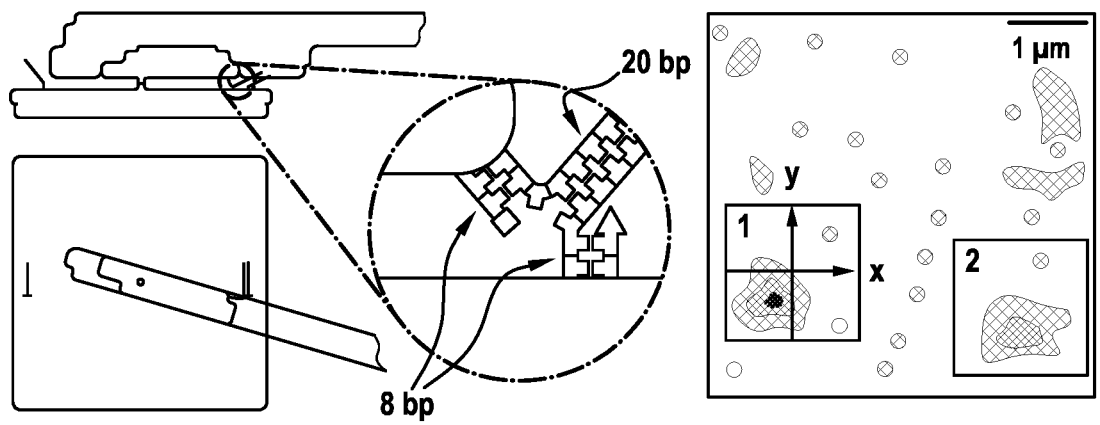
Figure 9D:
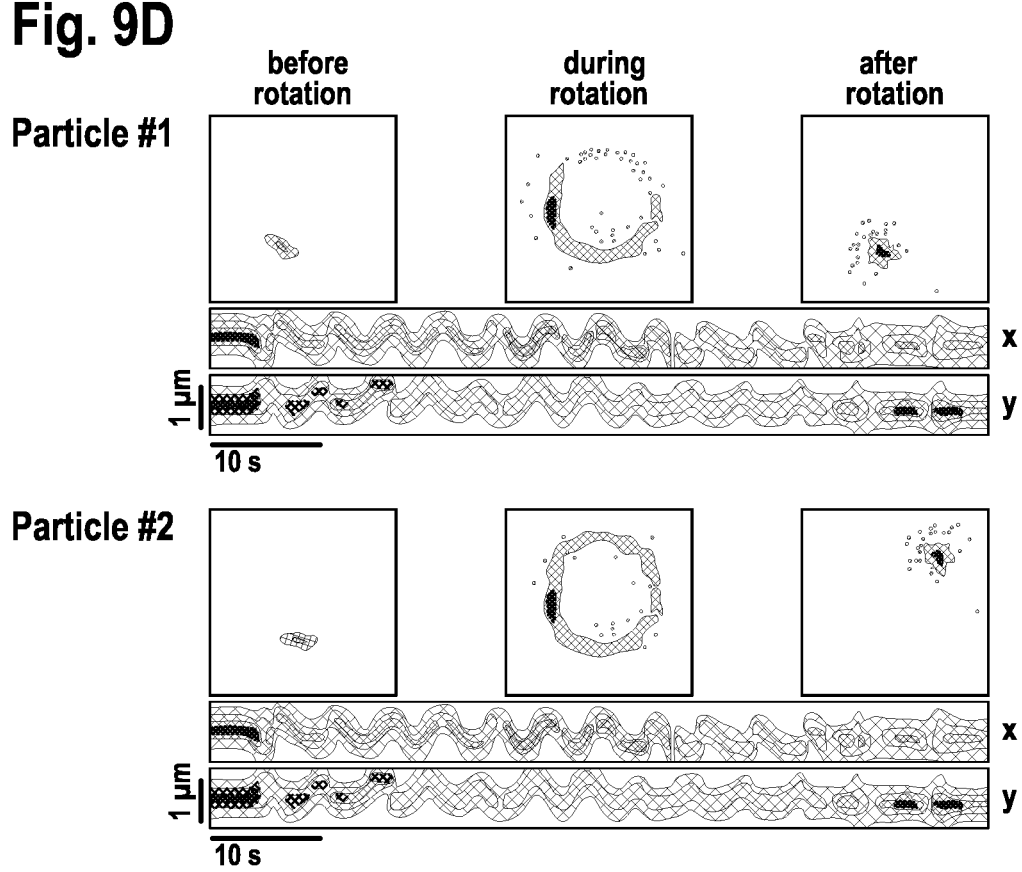

Next it is tested whether the robotic arm can wrest apart a 20 bp docking duplex, which is a stable structure at room temperature. While the arm is firmly locked in place in the absence of an electrical field, it can be released from the docking site by actuating the arm and rotated as shown in FIGS. 9C and 9D. Unzipping is expected to be most effective when the field is applied perpendicularly to the fixed arm. As the base plates are randomly oriented with respect to the sample chamber, the field is slowly rotated at a frequency of 0.2 Hz in order to guarantee each structure has sufficient time to experience a strong enough unzipping force. When switching off the field during rotation at an arbitrary phase, the arm immediately localizes to an available docking site.

At the field strengths generated in the sample chamber, field-induced melting of DNA duplexes is not expected as observed, e.g., for DNA structures immobilized on electrode surfaces. Instead, the arm acts as a lever which mechanically transduces the electrical force acting on its large charge to the docking duplex. Force-induced unzipping of DNA duplexes has been previously achieved using single molecule manipulation techniques such as AFM, optical tweezers or within nanopores. These experiments have shown that DNA unzipping requires forces on the order of 10-20 pN, which is consistent with the typical binding free energy of DNA base-pairs and their sub-nanometer spacing. A rough theoretical treatment suggests that forces that can be generated by the robot arm are on this scale. Importantly, the ability to separate stable duplexes by force facilitates the electrically controlled dissociation of the arm from one docking site and its subsequent placement at a different target position, which is then maintained also at zero field.

Figure 10A:
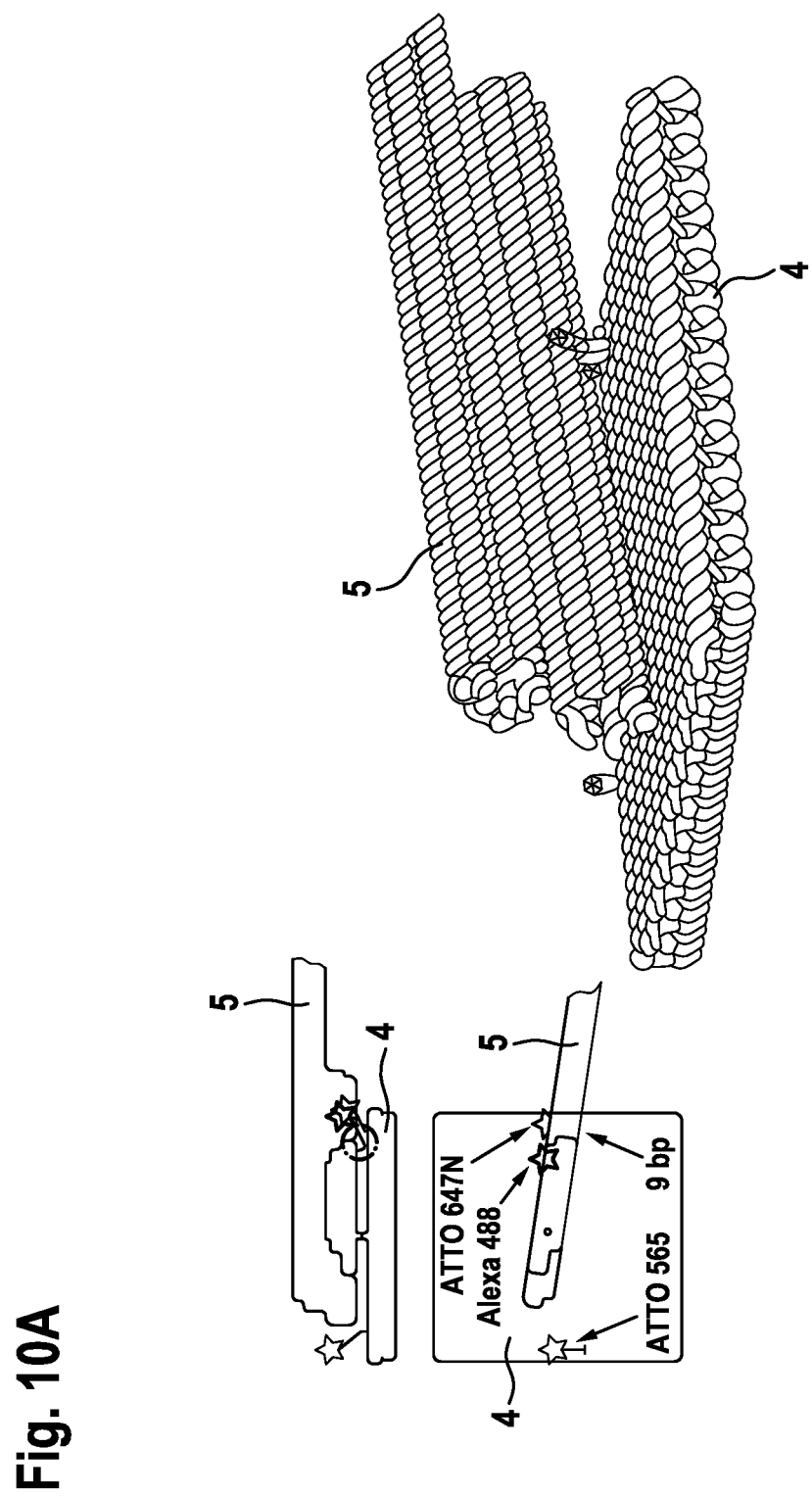

In order to show controlled movement of a cargo molecule attached to the arm, the three-color FRET system already employed in the stochastic switching experiments was utilized (FIG. 10A). In contrast to the stochastic switching experiments, the donor fluorophore is actively transported between two 9 nucleotides (nt) long docking positions by rotating the arm with the help of the high torque extension at rotation frequencies of f=1, 2, and 4 Hz, respectively. Alternating FRET traces (FIG. 10B) with the periodicity of the externally applied field are observed. In agreement with the latching experiments (FIG. 9B), higher rotation frequencies come with an increase in the number of "skips".

Figure 10D:
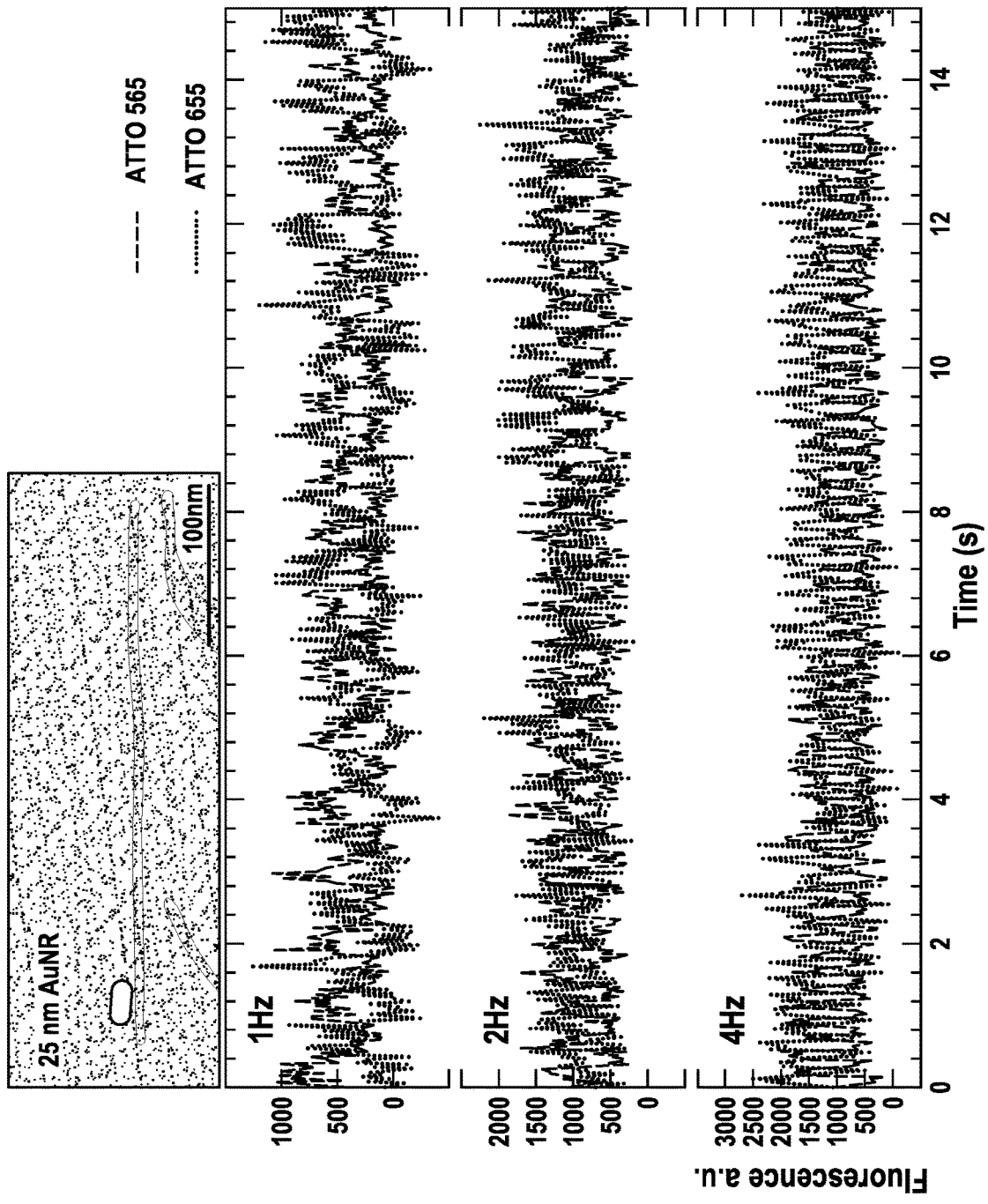

To demonstrate transport of inorganic nanoparticles by the robot arm, a gold nanorod (AuNR) was attached to one side of the 6HB arm, and its plasmonic interaction was probed with red (dotted line) and green (dashed line) fluorophores immobilized on the platform (FIG. 10C). As shown in FIG. 10D, the AuNR alternatingly modulates the fluorescence of the fluorophores during rotation of the arm at the externally prescribed frequency. Electrical manipulation enables faster operation of switchable biohybrid plasmonic systems than previously achieved with the fuel strand technique. More sophisticated systems involving multiple particles for the creation of switchable field enhancement or circular dichroism appear feasible.

In summary, an electrical actuation was introduced as a viable strategy for fast, computer-controlled operation of biohybrid nanorobotic systems, which can exert forces at the molecular scale. Compared to nanoscale manipulation methods such as scanning probe techniques, optical or magnetic tweezers, electrical control is contact-free and can be implemented with low-cost instrumentation. The robotic movements achieved are at least 5 orders of magnitude faster than previously reported for the fastest DNA motor systems and comparable to ATPase driven biohybrids. The robot arm system may be scaled up and integrated into larger hybrid systems using a combination of lithographic and self-assembly techniques. For instance, the platforms can be easily connected to form long filaments with multiple DNA robot arms or to create extended lattices. Utilization of algorithmic self-assembly will enable the creation of structures with different types of robot platforms with dedicated tasks. Lithographic patterning of the substrate will further allow the fabrication of robot arm arrays with defined platform orientations. Using nanostructured control electrodes, single robot arms could even be addressed individually and their positioning state could act as a molecular mechanical memory. Combined with appropriate pick-up and release mechanisms, it is conceivable that this technology can be also applied to DNA-templated synthesis. Electrically clocked synthesis of molecules with a large number of robot arms in parallel could then be the first step towards the realization of a genuine nanorobotic production factory.

Short Description of Materials and Methods:

In the following, the materials and methods used in the above explained embodiments are shortly described.

Buffer Solution Summary
- FB20—Origami folding buffer 20 mM $MgCl_2$: 1×TAE+ 20 mM $MgCl_2$
- NaB—Origami storage and assembly buffer: 1×TAE+1 M NaCl
- EB—Electrophoresis buffer: 0.5×TBE+6 mM $MgCl_2$
- EBPC—Electrophoresis buffer based photo cocktail: EB+2 mM Trolox (UV activated for about 15 min)+50 nM Protocatechuate 3,4-Dioxygenase (PCD)+2.5 mM Protocatechuic acid (PCA)+10 mM Ascorbic Acid (AA).
- StSwB—Stochastic switching buffer: 1×TE+12.5 mM MgCl2
- StSwBPC—Stochastic switching buffer based photo cocktail: StSwB+1 mM Trolox (UV activated for about 15 min)+10% Glycerol+10% (w/v) Glucose+10% (v/v) Glucoseoxidase-Catalase solution. Adjusted from protocol in Stein et al. (42).

DNA Origami Preparation

The scaffold strand for DNA origami folding was provided as a 100 nM solution in $ddH_2O$. All basic staple strands were added in a 2-fold excess over the scaffold strand. Staple strands with special functions, i.e., staples with additional extended sequences for site-specific binding or chemical modifications (fluorophores/biotin) were supplied in 5-fold excess. The solution was adjusted to contain 1×TAE and 20 mM $MgCl_2$. The structures were annealed in a Thermocycler (Bio-Rad Tetrad, Hercules, Calif., USA) that controls a temperature ramp from 70° C. to 20° C. over 12 h and successively holds the temperature at 40° C. for at least 3 hours. The unpurified samples were stored at room temperature until further use. A complete list of all oligonucleotide sequences is attached.

Structure Purification

All DNA origami samples were separated from excess strands by PEG precipitation. The detailed protocol can be found in the following paragraph. Fluorescent dyes for smFRET experiments were directly folded into the origami structure as covalent modifications of staple strands. All other dyes were attached by means of an adapter strand that hybridizes to an extended staple sequence. Adapter strands were added in 2-fold excess over each binding site and incubated for 1 h, followed by an additional step of PEG precipitation.

PEG Precipitation Protocol

The sample was mixed thoroughly in a 1:1 ratio with precipitation buffer (1×TAE, 1 M NaCl, 11% w/v PEG8k), and centrifuged at 20° C. with 20,000 rcf for 20 minutes. Afterwards the supernatant was carefully removed and the pellet resuspended in assembly buffer (1×TAE+1 M NaCl). Magnesium was replaced by sodium to avoid potential unspecific binding. This process is repeated a second time followed by determination of the concentration with a nanophotometer (NanoPhotometer Pearl, Implen GmbH, München, Germany).

Pointer Attachment

Pointer extensions were attached to the short 6HB arm of the robotic platform through incubation of 20 nM platform structure with 25 nM of the extension structure for at least 1 h at 37° C. while shaking.

AFM Imaging

AFM data was acquired with an Asylum Research Cypher ES (Oxford Instruments, Abingdon, UK) using Olympus BL-AC40TS-C2 (Olympus, Japan) cantilevers in AC mode. Structures were deposited on freshly cleaved mica and imaged in 1×TAE containing 12.5 mM $MgCl_2$.

TEM Imaging

TEM images were acquired with a Philips CM100 kV TEM and an AMT 4×4 Megapixel CCD camera. For negative staining, 25 µl NaOH was added to a 2% uranyl formate solution. The staining solution was centrifuged for 5 min at 20,000 rcf to avoid stain crystals. 5 µl of Nanostructure samples were incubated on glow discharged formvar coated carbon Cu400 TEM grids provided by Science Services (München, Germany) and incubated for 30 s. Subsequently, the grid was washed with 5 µl of staining solution, incubated for 40 s with 15 µl staining solution and dried with filter paper.

Biotin-PEG Slide Preparation

25×25 mm #1.5 cover slips (Menzel-Gläser, Braunschweig, Germany) were used. Biotin-PEG-silane MW 3,400 was acquired from Laysan Bio, Inc., Arab, USA and stored under an argon atmosphere. The procedure for PEG modification of cover slips was adapted from a protocol that was kindly provided by Matthias Schickinger (Dietz lab, TUM).

Cleaning:
 1. Place cover slips in a chemically inert rack inside a staining jar.
 2. Soak slides in 2 M NaOH for ~20 minutes, rinse with ddH2O.
 3. Heat 200 ml 2% Hellmanex II (Hellma GmbH & Co. KG, Müllheim, Germany) to ~100° C. and pour in staining jar. Sonicate 5 minutes.
 4. Rinse 3× with ddH2O, fill up with ddH2O. Sonicate 5 minutes.
 5. Repeat step 4.
 6. Fill staining jar with ethanol (99%). Sonicate 5 minutes.
 7. Dry in oven at 70° C., ~1 h.

PEG Coating:
 1. Prepare 0.5% biotin-PEG-silane in ethanol (p.a.) ~25 µl solution per slide.
 2. Add acetic acid (99%) to 1% final concentration.
 3. Place first slide on clean surface and add 25 µl of biotin-PEG-silane solution.
 4. Immediately place second slide on top. Repeat process until all slides are stacked.
 5. Incubate for 30 minutes at 70° C.
 6. Place stack in staining jar and sonicate in $ddH_2O$ for 5 minutes. Rinse twice.
 7. Separate slides and put back in rack.
 8. Repeat step 6.
 9. Blow dry with $N_2$ and store in dark and dry place.

Flow Chamber Production

Flow chambers were assembled from three elements: a biotin-PEG functionalized cover slip, a PMMA chip and a layer of double-sided tape. The double-sided tape acts as a spacer between the coverslip and PMMA chip and defines the channel height (about 50 µm). The double-sided tape 3M 467MP (3M Company, Maplewood, Minn., USA) was cut with a laser cutter (Trotec Speedy 100, Trotec Laser, Marchtrenk, Austria) to achieve precise and reproducible channel geometries. The double-sided tape was attached to the center of the PMMA chip and covered with the cover slip. The cover slip was pressed onto the slide with office clamps for at least 30 minutes.

5 mm thick PMMA plates were laser-cut into rectangular pieces of 75×25 mm with reservoirs that can hold 150-200 µl buffer volume each. Small indentations on the outside edge are used to fix a custom-made plug carrying 4 platinum electrodes. The electrodes are deliberately placed in large buffer reservoirs distant from the sample area to minimize detrimental effects of electrochemical processes occurring at the electrodes on the sample. The fully assembled sample during the experiment is shown in FIG. S6D. A 4-pin LEMO plug connects the 4-electrode plug to the power source.

Sample Preparation for Electric Field Alignment Experiments

Cutting of PMMA and tape as well as PEG functionalization was performed in advance at a larger scale (in batches of 20-30 pieces) and the components could then be stored over several weeks. Before each measurement, the fully assembled sample chambers were prepared for the experiment and discarded afterwards. Each chamber was flushed with 400 µl $ddH_2O$, then flushed with 20 µl NeutrAvidin (ThermoFisher Scientific, Waltham, Mass., USA) solution (0.5 mg/ml in ddH2O) and incubated for 30 seconds. Afterwards, the channels were rinsed thoroughly with 600 µl ddH2O followed by 400 µl assembly buffer (1×TAE, 1 M NaCl). 20 µl origami solution (500 µM structure concentration) was supplied to the flow chamber and incubated for 10 seconds. Afterwards, the channels were thoroughly flushed with 600 µl assembly buffer followed by 600 µl electrophoresis buffer (0.5×TBE, 6 mM MgCl2). The remaining buffer was removed from all edges of the reservoirs and 400 µl of the intended imaging buffer for the specific experiment was added. All electrophoretic switching experiments except the smFRET experiments were conducted in electrophoresis buffer. For increased lifetimes in smFRET electric switching experiments, the buffer was amended by an oxygen scavenging system (0.5×TBE, 6 mM MgCl2, 2 mM Trolox UV activated for >15 min, 50 nM Protocatechuate 3,4-Dioxygenase (PCD)+2.5 mM Protocatechuic acid (PCA)+10 mM L-Ascorbic acid (AA), adjusted from Aitken et al. (41)). PCD, PCA, AA and Trolox were acquired from Sigma-Aldrich, St. Louis, Mo., USA.

Voltage Control

A custom written LabView program was used to generate control voltages between +3.85 V and −3.85 V on two independent output cannels of a NI PCI-6036E DAQ Board (National Instruments Corporation, Austin, Tex., USA). The control voltages were amplified linearly to ±200 V by a home built DC amplifier containing an Apex PA443 high voltage operational amplifier (Apex Microtechnology, Tucson, Ariz., USA). The current setup controls the direction and strength of the electric field on a millisecond time scale, mainly limited by the loop time of the LabView program. A faster electrical response could be realized when necessary.

Alignment Strength Measurements

For each measurement, the structures were first rotated clockwise and counter clockwise with 1 Hz and 120 V for several turns and then aligned in one static direction with the target voltage for at least 1000 acquisition frames. The resulting videos were analyzed with the ThunderSTORM ImageJ plugin (45). Each point spread function was localized with a 2D Gaussian fit. The whole dataset was drift corrected and spot localizations with a fit accuracy of 50 nm or worse were discarded. Well-formed particles, which were sufficiently far from any other particle for reliable localization, were picked and the event list was further processed with MATLAB. For each individual particle, the localizations obtained during the first rotations were used to fit a circle. Subsequently the angular distribution of the localizations was measured in the presence of an electric field applied at a fixed angle. For each voltage, 38-150 particles were analyzed and the mean of each dataset was plotted.

AuNR Modification Protocol

AuNRs were purchased from Sigma-Aldrich (München, Germany). 50 µl thiolated DNA (100 µM) was incubated with 10 mM Tris(carboxyethyl) phosphine hydrochloride (TCEP) for at least 30 min. The DNA, 50 µl sodium dodecyl sulfate (SDS), and 10×TAE buffer were added to 1 ml AuNRs (1 nM). The pH was adjusted to 3 with HCl and incubated for 1 hour on a shaker. Subsequently, 0.5 M NaCl was added and the solution was again incubated for 3 h. Excess oligonucleotides were removed by centrifugation at 6,000 rcf for 20 min. The supernatant was removed and the pellet was dissolved in 2 ml 0.5×TAE containing 0.03% SDS. The centrifugation procedure was repeated 4 times. DNA functionalized AuNRs were added in 5-fold excess to the DNA nanostructures and incubated over night. Unbound AuNRs were removed from the origami sample by agarose gel electrophoresis purification.

Polymerization into Filaments

Polymerization of base plates was performed using a one-pot folding protocol. Two different scaffold lengths were used, which resulted in a statistical distribution of base plates with integrated robot arms and base plates that did not carry an arm. For baseplates without an arm, a p7249 scaffold was used. For base plates with an arm structure, we used a p7704 scaffold. The two folding solutions were pipetted separately and mixed in a 1:20 ratio of arm-less (p7249) and arm-forming (p7704) solution before folding. Polymerization was achieved by replacing the staples used for passivation of the edges of the bottom layer of the base plate by a set of staples that connects these two edges.

Fluorescence Microscopy a) TIRF Microscopy Setup for Stochastic Switching Kinetics Single-molecule multi-color FRET experiments were performed on a home built multi-color prism-type TIRF (total internal reflection fluorescence) setup based on an inverted microscope (TE 2000-U, Nikon, Japan) with four continuous-wave diode-pumped solid state lasers (Cobolt, Solna, Sweden) for excitation: 491 nm (Cobolt Calypso, 75 mW), 532 nm (Cobolt Samba, 100 mW), 561 nm (Cobolt Jive, 75 mW) and 647 nm (Cobolt MLD, 120 mW). The laser beams were aligned through an acousto-optical tunable filter (AOTFnC.400-650-PV-TN, Pegasus Optik, Wallenhorst, Germany) and coupled into a single-mode fiber to allow for intensity regulation and switching between the laser lines for alternating laser excitation (ALEX (24), see also below). The sample chambers were formed by sandwiching a nesco film channel cut-out between coverslip and a surface-functionalized quartz prism with holes to insert the sample. The quartz prisms were prepared as described earlier in Schluesche et al. (47). Briefly, the prism surface was silanized (3-aminopropyl-triethoxysilane, Sigma-Aldrich, St. Louis, Mo., USA) and then incubated with a solution of 45% polyethylene glycol (mPEG-SVA, MW 5000) and 3% biotin-PEG (biotin-PEG-SVA, MW 5000, Laysan Bio Inc., Arab, Ala., USA) in 100 mM sodium bicarbonate (pH 9.0) to achieve surface passivation.

Fluorescence from the sample was collected by a water immersion objective (CFI Plan Apo IR 60× NA 1.27 WI objective, Nikon) and separated by the dichroic mirrors 630 DCXR and 560 DCXR (AHF Analysentechnik AG, Tübingen, Germany). After selecting the different spectral regions with the respective emission filters HQ 525/50, HQ 595/50 and HQ 715/150, the fluorescence of the donor (Alexa Fluor 488) and two acceptor (ATTO 565 and ATTO 647N) fluorophores was detected on individual EMCCD cameras (Andor iXon 3, Andor Technologies, Belfast, UK).

b) Experimental Procedure for Stochastic Switching Kinetics Experiments Without Pointer Extension The prisms were initially incubated with a streptavidin (Sigma-Aldrich, St. Louis, Mo., USA) solution (0.3 mg/ml in PBS) for 20 minutes and washed with stochastic switching buffer (StSwB: 1×TE+12.5 mM $MgCl_2$). The samples were diluted to 100 µM in StSwB, added to the sample chamber and immobilize on the prism surface through biotin-streptavidin-biotin linkage. Untethered structures were removed by flushing with StSwB after 2-3 min. The prism was then flushed twice with stochastic switching buffer-based photo-cocktail (StSwBPC). Finally, the prism was filled completely with StSwBPC and the holes were sealed to facilitate oxygen removal. In the case of continuous donor excitation, the videos were recorded with 11 mW 491 nm excitation and simultaneous detection on the three EMCCD cameras at 30 ms exposure for 3000 frames. For the alternating laser excitation (ALEX) experiments, the laser excitation wavelength was synchronized with the camera frame rate using the AOTF and was switched frame by frame in the sequence red-green-blue (647 nm:3 mW, 561 nm:5 mW and 491 nm:11 mW). ALEX videos were recorded for 3000 frames at 30 ms exposure and simultaneous detection. The videos were analyzed with a custom-written MATLAB program (Mathworks, Mass., USA). Each fluorescent spot in a movie is presumed to represent a single structure. Spots belonging to the same structure were identified on the videos of the three fluorescence detection channels and fluorescence intensity traces were extracted from them.

c) Hidden Markov Model (HMM) Analysis of the Traces

Intensity traces for each color were individually subjected to a three-state HMM analysis. Two of the states correspond to the arm bound to either of the docking sites and are characterized by low donor fluorescence due to quenching by FRET to the acceptor at the docking site. The third state corresponds to the freely diffusing arm (unbound), characterized by high donor fluorescence in the absence of quenching by FRET.

Similarly, every trace of each of the two acceptors was individually subjected to a two-state HMM analysis, where one state corresponds to the arm bound to a particular docking site, characterized by high acceptor fluorescence due to FRET from the donor. The other state corresponds to the arm either docked to the other site or diffusing freely and is characterized by low acceptor fluorescence due to the absence of FRET. From the HMM analysis, the Viterbi path—the most likely sequence of states—was obtained for each fluorophore and for each trace. As an example, the trace from FIG. 7 in the top panel was replotted, whereas, in the bottom panel, the same trace is shown superimposed with the Viterbi paths of the three fluorophores in their designated colors. The anti-correlated movement of the donor and acceptors is clearly seen with every transition in the donor Viterbi path being mirrored by a transition of either of the acceptors.

Subsequently, the dwell times of the high fluorescence states of the fluorophores were determined from the Viterbi paths. The dwell time for a high acceptor fluorescence state corresponds to the time spent by the arm in the bound state (bound to a particular docking site). The dwell time for a high donor fluorescence signal corresponds to the time spent by the arm in the unbound state, where it can diffuse between the docking sites.

d) Stochastic Switching Without Pointer Extension: Control Experiments

Control experiments without docking: A control experiment for the stochastic switching experiments was performed by measuring samples where the arm lacks the extended staple strand for docking to the docking site with donor excitation. The resulting traces display an almost constant high donor fluorescence signal with hardly any switching of the fluorescence signals of the acceptors. Only a residual signal is observed in the acceptor channels, which can be accounted for by the direct-excitation of the acceptors upon donor excitation (491 nm) and crosstalk from the donor channel. This shows that, in the absence of the extended staple strand, docking of the arm does not occur. Hence, no stochastic switching of the acceptor signal is observed as the arm's rotational diffusion is much faster than the acquisition rate of the EMCCD cameras used in the setup (~30 fps).

ALEX experiments with docking: For samples with an extended staple strand on the arm for docking (docking duplex lengths 8-10 bp), videos were recorded with alternating laser excitation (ALEX), where the lasers were alternated every frame (frame time ~33 ms) in the sequence red-green-blue (647 nm laser-561 nm laser-491 nm laser) and with simultaneous detection on all three EMCCD cameras. An exemplary trace of an ALEX experiment with a 9 bp docking duplex arm structure shows that initially all fluorophores were present and active. At t≈275 s, the donor Alexa Fluor 488 bleaches. This was accompanied by a drop in total intensity (grey) to zero implying that the signal in the acceptor channels was solely due to FRET from the donor. Furthermore, upon 561 nm excitation (direct excitation of ATTO 565), there is clearly no FRET between the two acceptors. This is expected since the distance between the acceptors (~43 nm) is beyond the working range of FRET. The residual signal in the ATTO 647N channel after 561 nm excitation is attributed to the spectral crosstalk from ATTO 565 and a small amount of direct excitation of ATTO 647N by the 561 nm laser. Upon excitation with the 647 nm laser, only fluorescence from ATTO 647N is observed. The trace in figure S3B bottom panel shows that the ATTO 647N fluorophore is active throughout the experiment and does not bleach for the entire duration of the ~300 s long movie. The ALEX experiment thus demonstrates that the stochastic switching of the signals of the three fluorophores is only seen upon donor excitation, with all intensities dropping to zero when the donor bleaches. Since direct excitation of the acceptors shows that they were active for the entire duration of the experiment, a contribution of fluorophore photophysics to the stochastic switching of the signals can be ruled out.

e) TIRF Microscopy of Structures with Pointer Extension

All experiments involving electric field alignment were performed on a home built, objective type TIRF microscope based on an Olympus IX71 (Olympus, Japan). Three laser light sources with wavelengths 642 nm (Toptica iBeam smart, diode laser, 150 mW, Gräfelfing, Germany), 532 nm (Oxxius 532-50, diode-pumped solid state laser, 50 mW, Lannion, France), and 488 nm (Toptica iPulse, diode laser, 20 mW) are aligned in parallel, widened by a factor of 8.3 and focused on the back focal plane of a 100× oil immersion objective (UAPON 100×O TIRF objective, NA 1.49 oil, Olympus, Japan). The filter cube was configured with a ZT532/640RPC dichroic mirror and a ZET532/640 (Chroma Technology, Olching, Germany) emission filter. Except for the high-speed imaging experiments, the detected image is split into two emission channels, which are projected on two separate halves of the CCD chip of an Andor iXon 897 EMCCD camera (Andor Technologies, Belfast, UK). For this purpose, a Hamamatsu W-viewer (Hamamatsu Photonics, Japan) with the two filters (BrightLine HC 582/75 and ET Bandpass 700/75) and two dichroic mirrors (Beam splitter 630 DCXR and Beam Splitter Q 630 SPXR) was mounted on the left IX71 camera port (all from AHF analysentechnik AG, Tübingen, Germany). Structures with a multiply labeled extension were observed with 642 nm excitation and a laser power of 1-4 mW, depending on the desired observation time and SNR. For electric switching of the FRET signal, 7 mW of 488 nm excitation was used. Structures functionalized with AuNRs were excited with 1 mW at 642 nm and 1.7 mW at 532 nm. High-speed videos were recorded with an Andor Neo sCMOS camera (Andor Technologies, Belfast, UK) mounted to the right camera port of the Olympus IX71 body. In these measurements, the sample was excited with 50 mW at 642 nm.

Cadnano Designs

DNA origami structures were designed using cadnano. For the creation of 3D graphics, a set of MATLAB tools was used to convert the JSON file generated in cadnano into a PDB file that can be further used in UCSF Chimera. JSON files are available upon request from the authors.

Supplementary Text

Comparison of the Two Pointer Designs

In this work, two different approaches were utilized to create pointer extension structures for the central 6HB arm integrated with the platform. These extensions serve two purposes. First, they facilitate the observation of the robot arm's motion with diffraction limited light microscopy methods. Second, they act as highly charged levers that allow the application of larger forces to the central arm unit.

Stability: The linear pointer extension is attached to the tip of the arm. While this rather straightforward approach allows an extension by over 400 nm using the common p7249 scaffold, the low number of possible staple connections between the two origami structures did not seem to withstand the high bending forces that are associated with the transmission of torque to the arm. By contrast, the shape complementary pointer with its more bulky connector structure has a roughly 100 nm shorter range but connects to the arm with a larger number of staples, which are also spread over a larger area. This design appeared to be more stable against torque induced breakage.

Interactions with the plate/substrate: The two pointer designs significantly differed in their unspecific interactions with the origami base plate. While the linear extension showed relatively little interactions, the shape complementary pointer displayed two pronounced bias angles during rotational diffusion, or when actuated with low field strength. These undesired bias angles complicate the analysis of the movements.

Super-resolution imaging and defective devices: To compare the two pointer designs in terms of free rotational diffusion, a combination of localization microscopy and DNA-PAINT super-resolution microscopy was used. Three corners of the base plate were labeled with transient binding sites for DNA PAINT. For each image, videos were recorded with 1-2 mW at 642 nm excitation and 25 ms exposure. About 1000 frames with 25 ms exposure time were analyzed (spot detection, localization via Gaussian fitting, drift correction) with the ThunderSTORM ImageJ plugin. To reduce potential, unspecific sticking effects promoted by divalent ions, assembly buffer for imaging was used (1×TAE, 1 M NaCl). Subsequently, PAINT imaging buffer (1×TAE, 1 M NaCl, 0.05% TWEEN20, 5 nM imager strands) was added and a DNA-PAINT video was recorded (7000 frames, 250 ms exposure, 50 mW 642 nm excitation). The linear pointer has a slight bias to point in one direction perpendicular to the helix axis of the top layer of the origami plate, whereas the shape complementary pointer has two much stronger bias points on opposite sides of the plate along this direction.

Apart from a large fraction of correctly assembled structures, super-resolution images showed mainly two types of apparently damaged or misassembled structures. For type 1, the particle shows localizations also within a filled circle, instead of a ring-like pattern. This localization pattern suggests that the tip of the pointer is not restricted to the X-Y plane as designed but moves in the entire hemisphere above the base plate. It is assumed that the entire structure is misfolded or the connection between arm and pointer extension is defective. Type 2 is characterized by a ring without bias angles. Most of these structures also show a circular dot in the DNA-PAINT overlay rather than three distinct points indicating the labeled corners of the DNA base plate. A possible explanation for Type 2 defects is structures that are bound with only one biotin anchor, which could rotate along a single biotinylated staple strand. Movement would then still be restricted to the X-Y plane combined with a round, spot-like appearance of the base plate in the DNA-PAINT reconstruction.

Origami Staple List for Base Plate

| Oligo | Sequence | Staple Type | 1 | 7 | 8 | 9A,B | 9C,D | 10A,B | 10C,D |
|---|---|---|---|---|---|---|---|---|---|
| 32[167] 34[168] | AGACAAAAACACCACGG AATAAGTGTCAGAGG | basics | yes | yes | yes | yes | yes | yes | yes |
| 38[103] 40[104] | ATAAAGTAGGCGTTAAA TAAGAATTTAACCTC | basics | yes | yes | yes | yes | yes | yes | yes |
| 18[135] 20[136] | GGGACATTATGAAAAAT CTAAAGCATATCTTT | basics | yes | yes | yes | yes | yes | yes | yes |
| 34[103] 36[104] | CAAGAAACAAATAAGAA ACGATTTACCTCCCG | basics | yes | yes | yes | yes | yes | yes | yes |
| 36[63] 35[63] | GCTATTTTGCACCCAGT AATTTGCCAGTTACA | basics | yes | yes | yes | yes | yes | yes | yes |
| 21[120] 19[119] | TTCATCATAACAACTAAT AGATGAGAGCCA | basics | yes | yes | yes | yes | yes | yes | yes |
| 4[103]6[104] | TAGAGCTTTGTTTAGCT ATATTTTCCTGTAAT | basics | yes | yes | yes | yes | yes | yes | yes |
| 30[39] 32[40] | TCACAAAGAAACGTCAC CAATGAAAATCAC | basics | yes | yes | yes | yes | yes | yes | yes |
| 19[56] 17[63] | GATAAAACTTTTTGAATG GCTATTTTGATTAGTAAT AACA | basics | yes | yes | yes | yes | yes | yes | yes |
| 13[120] 11[119] | GTTTGCCTAACTCACAT TAATTCGGGATCC | basics | yes | yes | yes | yes | yes | yes | yes |
| 28[39] 30[40] | AGTACCGAGAATGGAAA GCGCACTTGATAT | basics | yes | yes | yes | yes | yes | yes | yes |
| 40[135] 42[136] | CATAGGTTATGTGAGTG AATAACAGATGAA | basics | yes | yes | yes | yes | yes | yes | yes |
| 40[167] 42[168] | CTGAGAAGCGTCGCTAT TAATTAAAAGAAAT | basics | yes | yes | yes | yes | yes | yes | yes |
| 8[135] 10[136] | AGAAAAGCTTGACCGTA ATGGGATCCAGCTTT | basics | yes | yes | yes | yes | yes | yes | no |

-continued

| Oligo | Sequence | Staple Type | FIG. 1 | 7 | 8 | 9A,B | 9C,D | 10A,B | 10C,D |
|---|---|---|---|---|---|---|---|---|---|
| 33[120] 31[119] | ACATACATGTAAATATTG ACGGAATGTAGCGC | basics | yes | yes | yes | yes | yes | yes | yes |
| 34[135] 36[136] | ACAAGAAAATGAAAATA GCAGCGGTATTCT | basics | yes | yes | yes | yes | yes | yes | yes |
| 36[95] 35[87] | GAGGTTTTGAAGCCTTA TTTAT | basics | yes | yes | yes | yes | yes | yes | yes |
| 40[39] 42[40] | AACGCGAGATGATGAAA CAAACAGGCGAAT | basics | yes | yes | yes | yes | yes | yes | yes |
| 16[71] 18[72] | TCCTGAGATCACTTGCC TGAGTAGTGGCAC | dock down 3' | yes | yes | yes | yes | yes | yes | no |
| 19[120] 17[127] | GCAGCAACTGGCCAACA GAGATATCCAGAACAAT ATT | basics | yes | yes | yes | yes | yes | yes | yes |
| 2[103]4 [104] | AAAGAAGTATAGTCAG AAGCAAAGGATGGCT | basics | yes | yes | yes | yes | yes | yes | yes |
| 22[135] 24[136] | CCAAATCCGGTCAATCA TAAGGTTTCATGA | basics | yes | yes | yes | yes | yes | yes | yes |
| 32[39] 34[40] | CAGTAGCAGGAAACGCA ATAATAAGCAGAT | basics | yes | yes | yes | yes | yes | yes | yes |
| 18[39] 20[40] | ATGCGCGAATACCGAAC GAACCACCAACTCGT | basics | yes | yes | yes | yes | yes | yes | yes |
| 12[167] 14[168] | AAGCATAACCGAAATCG GCAAAAGGGTTGA | dock right 5' | yes | yes | yes | yes | no | yes | yes |
| 34[71] 36[72] | ACCGAAGCAAATAAACA GCCATATTAAATCAA | basics | yes | yes | yes | yes | yes | yes | yes |
| 4[71]6 [72] | CTCAACATATTAGATACA TTTCGTCAACGC | dock up 5' | yes | yes | yes | yes | yes | yes | no |
| 32[71] 34[72] | AGCCATTTGAACTGGCA TGATTAAGCTATCTT | basics | yes | yes | yes | yes | yes | yes | yes |
| 31[120] 29[119] | GTTTTCATCCCTCAGAG CCGCCACGTAATAAG | basics | yes | yes | yes | yes | yes | yes | yes |
| 22[71] 24[72] | GAACGAGTCCTGATAAA TTGTGTCTAAAACGA | basics | yes | yes | yes | yes | yes | yes | yes |
| 18[71] 20[72] | AGACAATAAGAGGTGAG GCGGTCTTAGAAG | dock down 5' | yes | yes | yes | yes | yes | yes | yes |
| 21[88] 19[87] | TCATCATATAATACATTT GAGGATAGTATTAA | basics | yes | yes | yes | yes | yes | yes | yes |
| 16[135] 18[136] | CAGAGCGGACCGCCAG CCATTGCATAATAAAA | basics | yes | yes | yes | yes | yes | yes | no |
| 40[103] 42[104] | CGGCTTAGCTTTTTTAAT GGAAACATCGGGAG | basics | yes | yes | yes | yes | yes | yes | yes |
| 20[71] 21[87] | TATTAGACAACCACCAG AAGGAGCGGAATTA | basics | yes | yes | yes | yes | yes | yes | yes |
| 36[127] 35[119] | CGAGGCGTTTTAGCGAT TTGTTTA | basics | yes | yes | yes | yes | yes | yes | yes |
| 1[32]2 [40] | TTTAAGAACTGGCTCAA ATACTGC | basics | yes | yes | yes | yes | yes | yes | yes |
| 2[135]4 [136] | GATAAAAAAAGATTAAG AGGAAGCATTGCTCC | basics | yes | yes | yes | yes | yes | yes | yes |

-continued

| Oligo | Sequence | Staple Type | FIG. 1 | 7 | 8 | 9A,B | 9C,D | 10A,B | 10C,D |
|---|---|---|---|---|---|---|---|---|---|
| 6[167]8[168] | AGCAATAAGCCTGAGAGTCTGGAAAACTAG | basics | yes | yes | yes | yes | yes | yes | yes |
| 7[88]5[95] | GTTCTAGCGGGAGAAGCCTTTATTCAAATGGTCAATAACC | basics | yes | yes | yes | yes | yes | yes | yes |
| 2[71]4[72] | AAATGTTTAAATCAAAAATCAGGGCTGTAG | dock up 3' | yes | yes | yes | yes | yes | yes | yes |
| 36[159]35[159] | TATAGAAGGCTTATCCCTTTACAGAGAATA | basics | yes | yes | yes | yes | yes | yes | yes |
| 26[167]28[168] | TTTCTGTACAGCCCTCATAGTTAGTTAAGAGG | basics | yes | yes | yes | yes | yes | yes | yes |
| 30[167]32[168] | GAGCCGCCGTTTGCCATCTTTTCAAGCGCCAA | basics | yes | yes | yes | yes | yes | yes | yes |
| 23[120]22[104] | GGCGCAGAAACGTAACAAAGCTGCTCATTCAG | basics | yes | yes | yes | yes | yes | yes | yes |
| 28[71]30[72] | GGAATAGGTTCCAGTAAGCGTCATGACAGGAG | basics | yes | yes | yes | yes | yes | yes | yes |
| 32[135]34[136] | AGGGAAGAAAGGTGGCAACATAGATAACCC | basics | yes | yes | yes | yes | yes | yes | yes |
| 21[152]19[151] | TACTTCTGAGGAAGGTTATCTAAAATCACCTT | basics | yes | yes | yes | yes | yes | yes | yes |
| 26[71]28[72] | [Biotin] TTTT CACGTTGAATTTTCAGGGATAGCATATAGCCC | biotin | yes | yes | yes | yes | yes | yes | yes |
| 1[120]2[136] | GGTAGAAAGATTCATCAGTTGAGCAGACGAC | basics | yes | yes | yes | yes | yes | yes | yes |
| 24[39]26[40] | TTTGACCGCTTGCTTTCGAGGTGGCTCCAA | basics | yes | yes | yes | yes | yes | yes | yes |
| 32[103]34[104] | TTAAAGGTAGTATGTTAGCAAACGAATAAGAG | basics | yes | yes | yes | yes | yes | yes | yes |
| 12[103]14[104] | CTCACTGCAGTTGCAGCAAGCGGTCAAAGGGC | basics | yes | yes | yes | yes | yes | yes | yes |
| 38[135]40[136] | [Biotin] TTTT AGAGGCAATTACTAGAAAAAGCATCAAAAT | biotin | yes | yes | yes | yes | yes | yes | yes |
| 34[167]36[168] | GTAATTGAACATAAAAACAGGGAATAGCAAGC | basics | yes | yes | yes | yes | yes | yes | yes |
| 38[71]40[72] | [Biotin] TTTT GTCCAGACTGGTTTGAAATACCGATATATGTA | biotin | yes | yes | yes | yes | yes | yes | yes |
| 28[167]30[168] | CTGAGACTAAACAGTTAATGCCCCCTCCCTCA | basics | yes | yes | yes | yes | yes | yes | yes |
| 6[103]8[104] | ACTTTTGCTGATAAATTAATGCCGATTGTATA | basics | yes | yes | yes | yes | yes | yes | yes |
| 36[71]38[72] | GATTAGTTCCCATCCTAATTTACGGTAATTCT | basics | yes | yes | yes | yes | yes | yes | yes |
| 7[120]5[127] | AGCTATTCAAAAACATTATGACCATTTGGGGCGCGAG | basics | yes | yes | yes | yes | yes | yes | yes |
| 38[39]40[40] | CTAATGCTAGTTAATTTCATCTAGACAAAG | basics | yes | yes | yes | yes | yes | yes | yes |

-continued

| Oligo | Sequence | Staple Type | FIG. 1 | 7 | 8 | 9A,B | 9C,D | 10A,B | 10C,D |
|---|---|---|---|---|---|---|---|---|---|
| 8[71]10[72] | TTGTTAAACATCAACATTAAATGGCGCAAC | basics | yes | yes | yes | yes | yes | yes | no |
| 6[135]8[136] | GGTTGTACTTTGAGAGATCTACAATGATAATC | basics | yes | yes | yes | yes | yes | yes | no |
| 28[63]27[63] | TGTATCACCGTACTCACAGAGCCACCACCCTC | basics | yes | yes | yes | yes | yes | yes | yes |
| 30[71]32[72] | GTTGAGGCCACCGTAATCAGTAGCCCGACTTG | basics | yes | yes | yes | yes | yes | yes | yes |
| 18[103]20[104] | TCTGACCTGCAACAGTGCCACGCTTAGAGCCG | basics | yes | yes | yes | yes | yes | yes | yes |
| 41[88]39[95] | TGAATTACGTTGGGTTATATAACCCGTGTGATAAATAA | basics | yes | yes | yes | yes | yes | yes | yes |
| 12[135]14[136] | GAGTGAGCCCAGCAGGCGAAAATCGTCCACTA | basics | yes | yes | yes | yes | yes | yes | no |
| 4[39]6[40] | GGTGTCTGCAATTCTGCGAACGAGCATATATT | basics | yes | yes | yes | yes | yes | yes | yes |
| 42[135]41[119] | TATACAGTAACAGTACCTTTTACAGTACATA | basics | yes | yes | yes | yes | yes | yes | yes |
| 19[152]17[159] | GCTGAACCCCAGTCACACGACCAGACAGGAAAAACGCTCA | basics | yes | yes | yes | yes | yes | yes | yes |
| 21[56]19[55] | AACAAAGATTTACAAACAATTCGACAGCAGAA | basics | yes | yes | yes | yes | yes | yes | yes |
| 14[135]16[136] | TTAAAGAACAAGTGTAGCGGTCACGTTAGAAT | basics | yes | yes | yes | yes | yes | yes | no |
| 42[71]41[55] | ATACCAAGTTACAAAATCGCGCAGATCAAGAA | basics | yes | yes | yes | yes | yes | yes | yes |
| 22[175]24[168] | TCATCAAGAGTAATCTCTTTGAAAGAGGACAGACGGCTAC | basics | yes | yes | yes | yes | yes | yes | yes |
| 14[159]13[159] | CCAGTTTGGAACAAGACTGTTTGATGGTGGTT | basics | yes | yes | yes | yes | yes | yes | no |
| 24[71]26[72] | AAGAGGCATTGATACCGATAGTTGAATTTTTT | basics | yes | yes | yes | yes | yes | yes | yes |
| 10[39]12[40] | GCTATTACGGCGATTAAGTTGGGTGGCCAACG | dock left 3' | yes | no | yes | no | no | no | yes |
| 24[135]26[136] | GGAAGTTGTCGCTGAGGCTTGCAACTTTCA | basics | yes | yes | yes | yes | yes | yes | yes |
| 16[167]18[168] | GAGCACGTTGGAAATACCTACATACATTGG | basics | yes | yes | yes | yes | yes | yes | yes |
| 10[71]12[72] | TGTGGGACAGTCACGACGTTGTAAACCTG | basics | yes | yes | yes | yes | yes | yes | no |
| 2[95]1[87] | TTTTGCCAGAGGGGGTCTACGTTA | basics | yes | yes | yes | yes | yes | yes | yes |
| 36[103]38[104] | ACTTGCGGATCAATAATCGGCTGTAAGAGAAT | basics | yes | yes | yes | yes | yes | yes | yes |
| 9[88]7[87] | TAACAACCTTTAAATTGTAAACGTATTCAACC | basics | yes | yes | yes | yes | yes | yes | no |
| 2[127]1[119] | CCAAAATAGCGAGAGTTATTACA | basics | yes | yes | yes | yes | yes | yes | yes |

-continued

| Oligo | Sequence | Staple Type | FIG. 1 | 7 | 8 | 9A,B | 9C,D | 10A,B | 10C,D |
|---|---|---|---|---|---|---|---|---|---|
| 18[167] 20[168] | CAGATTCATCAAATATCA AACCCAGTTGAA | basics | yes | yes | yes | yes | yes | yes | yes |
| 29[88] 27[95] | TTTTGATGGAGGGTTGA TATAAGAGCCCAATAGG AACC | basics | yes | yes | yes | yes | yes | yes | yes |
| 14[127] 13[119] | CGTGGACTCCAACGTCC ACGCTG | basics | yes | yes | yes | yes | yes | yes | no |
| 30[103] 32[104] | [Biotin] TTTT CCACCAGAGCCTTTAGC GTCAGACATTATTCA | biotin | yes | yes | yes | yes | yes | yes | yes |
| 32[63] 31[63] | GGGAATTAGAGCCAGCA AACCATCGATAGCAG | basics | yes | yes | yes | yes | yes | yes | yes |
| 2[63]1 [55] | AGACTGGATAGCGTCCT TATACCA | basics | yes | yes | yes | yes | yes | yes | yes |
| 35[120] 33[119] | ACGTCAAATTGAGTTAA GCCCAATTAGAAAAT | basics | yes | yes | yes | yes | yes | yes | yes |
| 14[71] 16[72] | ACGTGAACGCCGGCGA ACGTGGCGCCAGAA | basics | yes | yes | yes | yes | yes | yes | no |
| 22[103] 24[104] | TGAATAAGCTCCATGTT ACTTAGCAATACGTA | basics | yes | yes | yes | yes | yes | yes | yes |
| 14[103] 16[104] | GAAAACCAAAGCGAAA GGAGCGGCCGATTAA | basics | yes | yes | yes | yes | yes | yes | yes |
| 24[167] 26[168] | AGAGGCTTCTTTTGCGG GATCGTCAAATGAAT | basics | yes | yes | yes | yes | yes | yes | yes |
| 23[56] 22[40] | TATCATCGAGTAAATTG GGCTTGAGATGGTTT | basics | yes | yes | yes | yes | yes | yes | yes |
| 11[88]9 [87] | GGCCAGTGATTCGCCAT TCAGGCTTGAGCGAG | basics | yes | yes | yes | yes | yes | yes | yes |
| 8[103] 10[104] | AGCAAATACGTCGGATT CTCCGTGAACCAGGC | basics | yes | yes | yes | yes | yes | yes | yes |
| 31[88] 29[87] | TCAAGTTTGCCGCCGCC AGCATTACATGGC | basics | yes | yes | yes | yes | yes | yes | yes |
| 16[39] 18[40] | ACCGAGTATTGTAGCAA TACTTCTAGTCTTTA | basics | yes | yes | yes | yes | yes | yes | yes |
| 41[152] 39[159] | CTGTAAATAGTCAATAG TGAATTTCTGTTTAGTAT CATAT | basics | yes | yes | yes | yes | yes | yes | yes |
| 10[103] 12[104] | AAAGCGCCCCAAGCTTT CTTTAGGGCGTTGCG | basics | yes | yes | yes | yes | yes | yes | yes |
| 1[56]2 [72] | GTCAGGACGTTGGGAA GAAAATAATAGTA | basics | yes | yes | yes | yes | yes | yes | yes |
| 6[63]5 [63] | AAATTTTAGAACCCTTA GATTTAGTTTGACC | basics | yes | yes | yes | yes | yes | yes | yes |
| 33[88] 31[87] | TATTACGCGAATTATCA CCGTCAGACAGAA | basics | yes | yes | yes | yes | yes | yes | yes |
| 2[167]4 [168] | AACACTATATCGCGTTTT AATTCTCCAACA | basics | yes | yes | yes | yes | yes | yes | yes |
| 6[39]8 [40] | TTAAATGCAAAAGGGTG AGAAAGGTGTTAAAT | basics | yes | yes | yes | yes | yes | yes | yes |
| 4[135]6 [136] | TTTTGATACTGAAAAGG TGGCATCGCTAAATC | basics | yes | yes | yes | yes | yes | yes | no |

-continued

| Oligo | Sequence | Staple Type | FIG. 1 | 7 | 8 | 9A,B | 9C,D | 10A,B | 10C,D |
|---|---|---|---|---|---|---|---|---|---|
| 4[167]6[168] | GGTCAGGAGTAGCATTAACATCCAAAATTA | basics | yes | yes | yes | yes | yes | yes | yes |
| 30[135]32[136] | GCCACCACGGCATTTCGGTCAATTGAGGG | basics | yes | yes | yes | yes | yes | yes | yes |
| 38[167]40[168] | CATATTTAGCGTTATACAAATTCTTTAAGACG | basics | yes | yes | yes | yes | yes | yes | yes |
| 8[39]10[40] | CAGCTCATAATTCGCGTCTGGCCTGCCTCTTC | basics | yes | yes | yes | yes | no | yes | yes |
| 10[167]12[168] | GGCCTCAGGTTTCCTGTGTGAAAGAGCCGG | dock right 3' | no | no | yes | no | no | no | yes |
| 1[152]2[168] | ATACCACATTCAACTAATGCAGATAAGAGC | basics | yes | yes | yes | yes | yes | yes | yes |
| 2[159]1[151] | CATAACCCTCGTTTACATTTAGGA | basics | yes | yes | yes | yes | yes | yes | yes |
| 40[71]42[72] | AATGCTGATAATTACATTTAACAATGCTTTGA | basics | yes | yes | yes | yes | yes | yes | yes |
| 28[159]27[159] | CCTCAAGAGAAGGATTTGTAGCATTCCACAGA | basics | yes | yes | yes | yes | yes | yes | yes |
| 9[120]7[119] | CGGCGGACCCAAAAACAGGAAGGAGAGGGT | basics | yes | yes | yes | yes | yes | yes | no |
| 20[39]21[55] | ATTAAATCTTGAGTAACATTATCATTTTGCGG | basics | yes | yes | yes | yes | yes | yes | yes |
| 29[120]27[127] | TTTTAACGTTGCTCAGTACCAGGCGAGTTTCGTCACCAGT | basics | yes | yes | yes | yes | yes | yes | yes |
| 13[88]11[87] | CCTGAGAGCCGCTTTCCAGTCGGGAAAACGAC | basics | yes | yes | yes | yes | yes | yes | yes |
| 23[88]22[72] | GCGACCTGGCTTGCCCTGACGAGAAACACCA | basics | yes | yes | yes | yes | yes | yes | yes |
| 42[103]41[87] | AAACAATAACGGATTCGCCTGATTTTCATT | basics | yes | yes | yes | yes | yes | yes | yes |
| 10[159]9[159] | GAAGATCGCACTCCAGAGGTCACGTTGGTGTA | basics | yes | yes | yes | yes | yes | yes | no |
| 19[88]17[95] | CACCGCCTGAAAGCGTAAGAATACGAAGAACTCAACTAT | basics | yes | yes | yes | yes | yes | yes | yes |
| 24[63]23[55] | AAAGAATACACTAAAAGAGATTTG | basics | yes | yes | yes | yes | yes | yes | yes |
| 12[71]14[72] | TCGTGCCACTGATTGCCCTTCACGCCCACT | basics | yes | yes | yes | yes | yes | yes | no |
| 20[103]21[119] | TCAATAGATTCCTGATTATCAGATGATGGCAA | basics | yes | yes | yes | yes | yes | yes | yes |
| 14[63]13[63] | CATCACCCAAATCAAGGTGAGACGGGCAACAG | basics | yes | yes | yes | yes | yes | yes | no |
| 32[159]31[159] | GGGCGACATTCAACCGTAGCCCCCTTATTAGC | basics | yes | yes | yes | yes | yes | yes | yes |
| 26[135]28[136] | [Biotin] TTTTACAGTTTACAAACTACAACGCCAGGATTAG | biotin | yes | yes | yes | yes | yes | yes | yes |
| 6[159]5[159] | AGCCTCAGAGCATAAAAATTCTACTAATAGTA | basics | yes | yes | yes | yes | yes | yes | yes |

-continued

| Oligo | Sequence | Staple Type | FIG. 1 | 7 | 8 | 9A,B | 9C,D | 10A,B | 10C,D |
|---|---|---|---|---|---|---|---|---|---|
| 36[39] 38[40] | TTATCCTATAGATAAGTC CTGAATGTTCAG | basics | yes | yes | yes | yes | yes | yes | yes |
| 11[120] 9[119] | CCGGGTAGCTTCTGGTG CCGGAGGAACAAA | basics | yes | yes | yes | yes | yes | yes | yes |
| 28[103] 30[104] | GCCGTCGAATACAGGA GTGTACTGCAGAACCA | basics | yes | yes | yes | yes | yes | yes | yes |
| 24[127] 23[119] | TCCATTAAACGGGTAAC GGAACGA | basics | yes | yes | yes | yes | yes | yes | yes |
| 26[103] 28[104] | CAACTAAACATGTACCG TAACACTGGATAAGT | basics | yes | yes | yes | yes | yes | yes | yes |
| 6[71]8 [72] | AAGGATAACACCATCAA TATGATTAATATT | basics | yes | yes | yes | yes | yes | yes | no |
| 26[39] 28[40] | AAGGAGCCAGAACCGC CACCCTGGAGGTTT | basics | yes | yes | yes | yes | yes | yes | yes |
| 10[63]9 [63] | AGGGCGATCGGTGCGG TCCTGTAGCCAGCTTT | basics | yes | yes | yes | yes | yes | yes | no |
| 23[152] 22[136] | CTGACCAATGACAAGAA CCGGATATTCATTAC | basics | yes | yes | yes | yes | yes | yes | yes |
| 14[95] 13[87] | GTCTATCAGGGCGATGC GCCTGGC | basics | yes | yes | yes | yes | yes | yes | no |
| 42[167] 41[151] | TGCGTAGATTTTCAGGT TTAACGTCCTTGCTT | basics | yes | yes | yes | yes | yes | yes | yes |
| 24[159] 23[151] | TGAGGACTAAAGACTTG AACCGAA | basics | yes | yes | yes | yes | yes | yes | yes |
| 24[95] 23[87] | ACGAAGGCACCAACCG AAATCC | basics | yes | yes | yes | yes | yes | yes | yes |
| 36[135] 38[136] | AAGAACGAAGAACGGGT ATTAAATTTAGGC | basics | yes | yes | yes | yes | yes | yes | yes |
| 14[167] 16[168] | GTGTTGTTACACCCGCC GCGCTTCTTTGAC | basics | yes | yes | yes | yes | yes | yes | yes |
| 41[120] 39[127] | AATCAATACTGAGAGAC TACCTTTAAACACCGGA ATCATA | basics | yes | yes | yes | yes | yes | yes | yes |
| 28[135] 30[136] | CGGGGTTGGGTCAGTG CCTTGACCCTCAGA | basics | yes | yes | yes | yes | yes | yes | yes |
| 36[167] 38[168] | AAATCAGAATCGAGAAC AAGCAAGAGAATCGC | basics | yes | yes | yes | yes | yes | yes | yes |
| 16[103] 18[104] | AGGGATTTCGGCCTTGC TGGTAATAGAACCCT | basics | yes | yes | yes | yes | yes | yes | yes |
| 41[56] 39[63] | AACAAAATTGCAAATCC AATCGCATCTGACCTAA ATTTAA | basics | yes | yes | yes | yes | yes | yes | yes |
| 20[135] 21[151] | AGGAGCACATATAATCC TGATTGTTTGGATTA | basics | yes | yes | yes | yes | yes | yes | yes |
| 2[39]4 [40] | GGAATCGTCTTTAAACA GTTCAGATAAAGTAC | basics | yes | yes | yes | yes | yes | yes | yes |
| 8[167] 10[168] | CATGTCAAGATGGGCGC ATCGTACAGTATC | basics | yes | yes | yes | yes | yes | yes | yes |
| 24[103] 26[104] | ATGCCACTCAACCATCG CCCACGCGAAAGGAA | basics | yes | yes | yes | yes | yes | yes | yes |

-continued

| Oligo | Sequence | Staple Type | FIG. 1 | 7 | 8 | 9A,B | 9C,D | 10A,B | 10C,D |
|---|---|---|---|---|---|---|---|---|---|
| 1[88]2[104] | ATAAAACGAACTAACGGAACAACAGCTTTTGC | basics | yes | yes | yes | yes | yes | yes | yes |
| 14[39]16[40] | GGTCGAGGGGAGCCCCCGATTTAGTGAGGCC | basics | yes | yes | yes | yes | yes | yes | yes |
| 22[39]24[40] | AATTTCAAAACAAAGTACAACGCACTCATC | basics | yes | yes | yes | yes | yes | yes | yes |
| 10[135]12[136] | CCGGCACCCCGAGCTCGAATTCGTTGCCTAAT | basics | yes | yes | yes | yes | yes | yes | no |
| 35[88]33[87] | CCCAATCCAATGAAATAGCAATAGACTCCT | basics | yes | yes | yes | yes | yes | yes | yes |
| 12[39]14[40] | CGCGGGGAGTTTTCTTTTCACCATTTTTTGG | dock left 5' | yes | yes | yes | yes | no | yes | yes |
| 34[39]36[40] | AGCCGAACGTCTTTCCAGAGCCCTACAATT | basics | yes | yes | yes | yes | yes | yes | yes |
| 3T38[95]7[159] | CCTTTTTAATTTTTGCGCGGATTGCATCAAA | crossover top/bottom layer | yes | yes | yes | yes | yes | yes | yes |
| 3T26[127]11[63] | GAGCTAAATCAGAGATAAAAGAAACGCAAAG | crossover top/bottom layer | yes | yes | yes | yes | yes | yes | yes |
| 3T34[63]3[127] | CCGACAAAACCCCGGTAGGCTATCAGGTCATT | crossover top/bottom layer | yes | yes | yes | yes | yes | yes | yes |
| 3T8[159]37[95] | ATTCGCATGAATAATCGCCGACAATGACAA | crossover top/bottom layer | yes | yes | yes | yes | yes | yes | yes |
| 3T4[159]37[63] | TGGGATTTTATAATCAGAGCTTGACGGGGAAA | crossover top/bottom layer | yes | yes | yes | yes | yes | yes | yes |
| 3T16[95]29[159] | GTTTTAAAAAAAAAAGAATTTCTTAAACAGC | crossover top/bottom layer | yes | yes | yes | yes | yes | yes | yes |
| 3T30[159]15[95] | TAGACAGGAACCGCCAGTAACAGTGCCCGTAT | crossover top/bottom layer | yes | yes | yes | yes | yes | yes | yes |
| 3T26[95]7[63] | AGGTCAGAAATATAATTCTTTACCCTGACTAT | crossover top/bottom layer | yes | yes | yes | yes | yes | yes | yes |
| 3T16[159]37[159] | AGTGTAAACCAGTAATCTTTCCTTATCATTCC | crossover top/bottom layer | yes | yes | yes | yes | yes | yes | yes |
| 3T38[63]3[159] | AGAGGTCAGAAAAGTAACGGAATACCCAAAA | crossover top/bottom layer | yes | yes | yes | yes | yes | yes | yes |

-continued

| Oligo | Sequence | Staple Type | FIG. 1 | 7 | 8 | 9A,B | 9C,D | 10A,B | 10C,D |
|---|---|---|---|---|---|---|---|---|---|
| 3T34[159]15[127] | GCTGCATTTGAGAATAATAACCGATATATTCG | crossover top/bottom layer | yes | yes | yes | yes | yes | yes | yes |
| 3T30[63]3[95] | GGAATTGCTAAATTTTCCGGAGACAGTCAAAT | crossover top/bottom layer | yes | yes | yes | yes | yes | yes | yes |
| 3T38[159]15[159] | AATTGCTGCGATTGGCGTCTCTGAATTTACCG | crossover top/bottom layer | yes | yes | yes | yes | yes | yes | yes |
| 3T16[63]25[159] | ACAACGCCCTTTCCTCGCTGCGCGTAACCACC | crossover top/bottom layer | yes | yes | yes | yes | yes | yes | yes |
| 3T16[127]33[159] | TCATATGTAGGTAAAAGCATGTAGAAACCA | crossover top/bottom layer | yes | yes | yes | yes | yes | yes | yes |
| 3T12[63]25[127] | CAGCGGAGAATGAATCAACGCCAGGGTTTTCC | crossover top/bottom layer | yes | yes | yes | yes | yes | yes | yes |
| 3T8[63]25[95] | TTAGAGAGTAAACAACACAAGAAAAATAATAT | crossover top/bottom layer | yes | yes | yes | yes | yes | yes | yes |
| 3T4[63]25[63] | TTTTCGAGGCCTGGGAATCATGGTCATAGCT | crossover top/bottom layer | yes | yes | yes | yes | yes | yes | yes |
| 3T12[159]37[127] | GACGACAATACCTTTACCGAAAGACTTCAAAT | crossover top/bottom layer | yes | yes | yes | yes | yes | yes | yes |
| 3T4[95]29[63] | AGTGTTTTTGCTAAACAGGGAGTTAAAGGCCG | crossover top/bottom layer | yes | yes | yes | yes | yes | yes | yes |
| 3T4[127]33[63] | GCGCTAATACAGGAGGGCGCTAGGGCGCTGG | crossover top/bottom layer | yes | yes | yes | yes | yes | yes | yes |
| 3T38[127]11[159] | AAATCTCCTATGCAACAAACGAGAATGACCAT | crossover top/bottom layer | yes | yes | yes | yes | yes | yes | yes |
| 3T26[159]15[63] | ACCCTCAGAACGGTACGAGAAAGGAAGGGAAG | crossover top/bottom layer | yes | yes | yes | yes | yes | yes | yes |
| 3T26[63]3[63] | ATAACGTGAACATGTAACCAAGTACCGCACTC | crossover top/bottom layer | yes | yes | yes | yes | yes | yes | yes |

6HB Arm StSw

| Oligo Position | Sequence | Staple Type | FIG. 1 | 7 | 8 | 9A,B | 9C,D | 10A,B | 10C,D |
|---|---|---|---|---|---|---|---|---|---|
| 1[63]3[76] | GGAAGCAGTTCCCAGT CACGATTCATGC | basics | yes | yes | no | no | no | no | no |
| 1[13]2[20] | TTTAGGGCTTAAGCTAC GTGGTTCTGACGTTGGT TTT | basics | yes | yes | no | no | no | no | no |
| 4[62]3[48] | AACCCCGCTTCTAATCT ATTTGGTGGAT | basics | yes | yes | no | no | no | no | no |
| 2[55]3[62] | AGCCAGGGTTCTTCTAA GTGG | basics | yes | yes | no | no | no | no | no |
| 3[20]4[16] | TTTCGGCCCTAGGAGA AGCCAGACGCTCGCCC TGGAGTGACTCTATTT | basics | yes | yes | no | no | no | no | no |
| 2[90]0[70] | CGGTCTTGCCCAGACT GAGACTCGGCTGACGC ATT | basics | yes | yes | no | no | no | no | no |
| 2[48]0[28] | TGACATTGAGTGCGGC TTGTTCCTCCTGGTTGG TG | basics | yes | yes | no | no | no | no | no |
| 5[70]3[69] | GAATATATGTCCCGCCA AAATTTGTGAA | basics | yes | yes | no | no | no | no | no |
| 5[49]0[63] | AAGCAACTCGTCGGTG GGCACTCACATA | basics | yes | yes | no | no | no | no | no |
| 0[85]1[105] | AACGACCATGGGGAAC TCAACTTT | basics | yes | yes | no | no | no | no | no |
| 5[16]0[13] | TTTTGATACCGATAATG AGTAAACTTT | basics | yes | yes | no | no | no | no | no |
| 3[77]5[88] | GCACGACATGACAAGG GGCCTTGTTT | basics | yes | yes | no | no | no | no | no |
| 5[28]1[55] | CAGTGCGGCCCTGCCA TCTGTACTCTGAACCTC GATAAAGAC | basics | yes | yes | no | no | no | no | no |
| 2[69]0[49] | CACCTGACAAACCCGG AAGTTAATCATTTCTCC GA | basics | yes | yes | no | no | no | no | no |
| 4[102]3[90] | TTTCTGAATTGTCAACC TTTTAAGTG | FRET Donor | yes | no | no | no | no | no | no |

6HB Arm Linear Extension

| Oligo Position | Sequence | Staple Type | FIG. 1 | 7 | 8 | 9A,B | 9C,D | 10A,B | 10C,D |
|---|---|---|---|---|---|---|---|---|---|
| 1[50]3[62] | AAAGACAGCCAGGG TTCTTCTAAGTGG | basics | no | no | yes | no | no | no | no |
| 1[30]3[41] | GTGGTTCTGACGTTG GTTTTTTTCGGCCCT AGGAGAAGCCAG | basics | no | no | yes | no | no | no | no |
| 4[62]3[48] | AACCCCGCTTCTAAT CTATTTGGTGGAT | basics | no | no | yes | no | no | no | no |
| 2[48]0[34] | TGACATTGAGTGCGG CTTGTTCCTCCTGG | basics | no | no | yes | no | no | no | no |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 0[53]1[71] | TCCGAAAGCAACTCG TCGGTGGGCACTCA CATAGGAAGCAGT | basics | no | no | yes | no | no | no | no |
| 0[21]1[29] | GTAAACTTTTTTAGG GCTTAAGCTAC | basics | no | no | yes | no | no | no | no |
| 4[41]0[22] | ACGCTCGCCCTGGA GTGACTCTATTTTTT GATACCGATAATGA | basics | no | no | yes | no | no | no | no |
| 0[33]1[49] | TTGGTGCAGTGCGG CCCTGCCATCTGTAC TCTGAACCTCGAT | basics | no | no | yes | no | no | no | no |
| 2[69]0[54] | CACCTGACAAACCCG GAAGTTAATCATTTC | basics | no | no | yes | no | no | no | no |
| 4[111]3[90] | GTAAGCGTCATACTG AATTGTCAACCTTTTA AGTG | Crossover Arm to 6hb Ext | no | no | yes | no | no | no | no |
| 2[114]6[77] | TTAAAGGCCGCTAAC AGCAGTTGCTCCTTA GTGTTATAGTTGTAT AA | Crossover Arm to 6hb Ext, Arm Extension to Dock | no | no | yes | no | no | no | no |
| 1[71]5[97] | TTCCCAGTCACGATT CATGCGCACGACATG ACAAGGGGCCTTGA GAGTCTGGAGC | Crossover Arm to 6hb Ext | no | no | yes | no | no | no | no |
| 0[97]3[69] | GGTCATTGCCTGAAT CGGCTGACGCATTGA ATATATGTCCCGCCA AAATTTGTGAA | Crossover Arm to 6hb Ext | no | no | yes | no | no | no | no |
| 2[90]1[114] | CGGTCTTGCCCAGAC TGAGACCGACCATG GGGAACTCAACTTTG CGGGATCG | Crossover Arm to 6hb Ext | no | no | yes | no | no | no | no |

6HB Arm High Torque Extension

| Oligo Position | Sequence | Staple Type | FIG. 1 | 7 | 8 | 9A,B | 9C,D | 10A,B | 10C,D |
|---|---|---|---|---|---|---|---|---|---|
| 5[209]3[223] | AGCAACTCATCATTTC GTGGTGCTTGTTAAAC TCAATGGTTGT | AuNRExt | no | no | no | yes | yes | no | no |
| 3[203]2[189] | GATGTTCCTAATCTATT TACGCTCGCCCGAGAA GCCCCAGAG | Basics | no | no | no | yes | yes | yes | yes |
| 1[176]3[202] | CGGAATACGTAATGAG TAAACAGGGCTGGTCT TGCAGGGTG | Crossover to Extension, AuNRExt | no | no | no | yes | yes | yes | no |
| 6[224]4[231] | TTCTGAATTGTCAACC TTATGACAATGT | Crossover to Extension, 5PrDockExtension | no | no | no | yes | no | yes | yes |
| 0[247]1[256] | TTTTCTGAATCGGCTG AAAAGACGGAAGTTGG AAGCCGGATAA | Crossover to Extension, AuNRExt | no | no | no | yes | yes | yes | no |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 3[224]5[250] | GAATTCACCCGCCAGGCACGAATATAGGGGCCTGGTCATAG | Crossover to Extension | no | no | no | yes | yes | yes | yes |
| 2[253]6[255] | CAGGAGTTCCCACTGAGACTTAAGTGTCCTTAGTGTT | Crossover to Extension, 3PrDockExtension | no | no | no | no | no | no | yes |
| 5[175]0[175] | CAATGATACCGACAGTGCGGCCTCCTGGTTGGTCCAAAGAA | Crossover to Extension | no | no | no | yes | yes | yes | yes |
| 2[188]4[171] | TCACGACACCTGACCGTTGGTCGGCCAGTGGAGTGACTCTCAAGAA | Crossover to Extension, AuNRExt | no | no | no | yes | yes | yes | no |
| 3[154]2[152] | CCTTTCATTGAGTGCGTCTGAAAACCCAGCCAGGTGATTAAGAA | Crossover to Extension, AuNRExt | no | no | no | yes | yes | yes | no |
| 7[217]3[216] | CAATAGACACATAAGTCGGTGAAATAACCCCGCTTTTCTAAG | Crossover to Extension, AuNRExt | no | no | no | yes | yes | yes | no |
| 3[231]7[230] | TGCGCACGACCGACCATGGGGCCTCGATCGCATTTAAATTCA | Crossover to Extension | no | no | no | yes | yes | yes | yes |
| 2[216]7[209] | CAACAGCAGTTGCCTAAGCTACTCCGAATATTTTG | Crossover to Extension, AuNRExt | no | no | no | yes | yes | yes | no |
| 7[196]5[208] | ATAAGTTCTCTGACCCTGCCATCTGTA | Crossover to Extension | no | no | no | yes | yes | yes | yes |

6HB Arm High Torque Extension AuNR

| Oligo Position | Sequence | Staple Type | FIG. 1 | 7 | 8 | 9A,B | 9C,D | 10A,B | 10C,D |
|---|---|---|---|---|---|---|---|---|---|
| 1[176]Short Au8ADist | CGGAATACGTAATGAGTAAAAAAAAA | 8A 3Prime | no | no | no | no | no | no | yes |
| 3[154]Short Au8ADist | CCTTTCATTGAGTGCGTCTGAAACCCAAAAAAAA | 8A 3Prime | no | no | no | no | no | no | yes |
| 5[209]Short Au8ADist | AGCAACTCATCATTTCGTGGTGAAAAAAAA | 8A 3Prime | no | no | no | no | no | no | yes |
| 0[247]Short Au8ADist | TTTTCTGAATCGGCTGAAAAGACGAAAAAAAA | 8A 3Prime | no | no | no | no | no | no | yes |
| 7[217]Short Au8ADist | CAATAGACACATAAGTCGGTGAAATAACCCCGCTTTTCTAAGCAACAGCAAAAAAAA | 8A 3Prime | no | no | no | no | no | no | yes |
| 2[188]Short Au8AProx | AAAAAAAATCACGACACCTGACCGTTGGTCGGCCAGTGGAGTGACTCTCAAGAA | 8A 5Prime | no | no | no | no | no | no | yes |
| 1[195]Short Au8AProx | AAAAAAAAACAGGGCTGGTCTTGCAGGGTG | 8A 5Prime | no | no | no | no | no | no | yes |
| 1[217]Short Au8AProx | AAAAAAAACTTGTTAAACTCAATGGTTGT | 8A 5Prime | no | no | no | no | no | no | yes |
| 2[209]Short Au8AProx | AAAAAAAAAGTTGCCTAAGCTACTCCGAATATTTTG | 8A 5Prime | no | no | no | no | no | no | yes |

| Oligo Position | Sequence | Staple Type | FIG. 1 | 7 | 8 | 9A,B | 9C,D | 10A,B | 10C,D |
|---|---|---|---|---|---|---|---|---|---|
| 1[238]Short Au8AProx | AAAAAAAAGAAGTTGGAAGCCGGATAA | 8A 5Prime | no | no | no | no | no | no | yes |
| 2[168]Short Au8AProx | AAAAAAAAAGCCAGGTGATTAAGAA | 8A 5Prime | no | no | no | no | no | no | yes |

Linear Extension

| Oligo Position | Sequence | Staple Type | FIG. 1 | 7 | 8 | 9A,B | 9C,D | 10A,B | 10C,D |
|---|---|---|---|---|---|---|---|---|---|
| 0[391]3[384] | TAGCAAAACGGCGGTTTCGGTCATAGCCCCTCAGA | basics | no | no | yes | no | no | no | no |
| 0[517]3[510] | TTCGCAACCGGCACTAGCACCATTACCATGAATAA | basics | no | no | yes | no | no | no | no |
| 0[223]3[216] | AAGATTCAACGTTACAGCATTGACAGGATATTATT | basics | no | no | yes | no | no | no | no |
| 0[643]3[636] | TATAATGCTGCAAGCAAAGGGCGACATCTGAGAG | basics | no | no | yes | no | no | no | no |
| 1[868]3[881] | CTCGTTTAGAAGGATATGCTTATACAA | basics | no | no | yes | no | no | no | no |
| 1[343]3[356] | TATCATCGTTTCAGTGTATCACCGTACT | basics | no | no | yes | no | no | no | no |
| 1[994]3[1007] | AGAGTCTATTTGAGGAATATAAAGTACC | basics | no | no | yes | no | no | no | no |
| 0[412]3[405] | CATACAGGATAGGTGTAGCGCGTTTTCAAACCGCC | basics | no | no | yes | no | no | no | no |
| 0[265]3[258] | CCTCATAATCAGCTCACCCTCAGAGCCGCAAGAGA | basics | no | no | yes | no | no | no | no |
| 1[889]3[902] | AAAACCATTGCGGACCAGTATAAAGCCA | basics | no | no | yes | no | no | no | no |
| 0[580]3[573] | TCCATATGTTGGGAAAGGTGAATTATCAATAGCGA | basics | no | no | yes | no | no | no | no |
| 1[1057]3[1070] | CTTGCCTGTTATCTTCAGCTAATGCAGA | basics | no | no | yes | no | no | no | no |
| 1[931]3[944] | AGAGGGGCCGAACGTCGCCATATTTAAC | basics | no | no | yes | no | no | no | no |
| 1[826]3[839] | AAAGGAATGGCAATACACCGGAATCATA | basics | no | no | yes | no | no | no | no |
| 1[1036]3[1049] | CTTTGATAGCACTACGACGACAATAAAC | basics | no | no | yes | no | no | no | no |
| 0[475]3[468] | GGGCGCGCGACAGTAACCATCGATAGCATACCGTA | basics | no | no | yes | no | no | no | no |
| 1[1078]3[1091] | AAACTATAGTTGAATGTTTATCAACAAT | basics | no | no | yes | no | no | no | no |
| 0[496]4[483] | GTTTAGCGATCGCAGGCCGGAAACGTCA | basics | no | no | yes | no | no | no | no |
| 0[979]3[972] | TACGCCAGGTTTGCCTAATATCAGAGAGCAGAGGC | basics | no | no | yes | no | no | no | no |
| 1[910]3[923] | TTTTGCAAGTTTGAACAGTAGGGCTTAA | basics | no | no | yes | no | no | no | no |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 1[700]3 [713] | AGGACGTTTTAACGCCAATCG CAAGACA | basics | no | no | yes | no | no | no | no |
| 0[601]3 [594] | TACGGTGGGGCCTCATTGAC GGAAATTAACGCTGA | basics | no | no | yes | no | no | no | no |
| 0[202]3 [195] | GGCCGGATAAGCAAGCAGGT CAGACGATCCCCCTG | basics | no | no | yes | no | no | no | no |
| 0[328]3 [321] | GACCCTGGCCAGCTAGCCAC CACCGGAAGGTTGAT | basics | no | no | yes | no | no | no | no |
| 1[280]3 [293] | AAACACTTTGAAAATTGCTCA GTACCAG | basics | no | no | yes | no | no | no | no |
| 1[322]3 [335] | ACAAAGTAAAGGAAATAAGTA TAGCCCG | basics | no | no | yes | no | no | no | no |
| 0[181]3 [174] | CATCAATCCCAAAAGATATTC ACAAACATGCCCGT | basics | no | no | yes | no | no | no | no |
| 1[1162]3 [1175] | TTTTGACAGCAAATGGCTGTC TTTCCTT | basics | no | no | yes | no | no | no | no |
| 1[1120]3 [1133] | CCAGCCATATCAAATCCCATC CTAATTT | basics | no | no | yes | no | no | no | no |
| 1[1183]3 [1196] | AATGGATAGTGCCACAAGAAC GGGTATT | basics | no | no | yes | no | no | no | no |
| 0[1000]3 [993] | AGGGATTGGTGGTTAAGTCA GAGGGTAAAATAAGA | basics | no | no | yes | no | no | no | no |
| 1[427]3 [440] | GGGAACCGCGTAACATTTTCA GGGATAG | basics | no | no | yes | no | no | no | no |
| 0[1021]3 [1014] | GCTAAACTGAGACGATTAACT GAACACCGACAAAA | basics | no | no | yes | no | no | no | no |
| 0[1168]3 [1161] | GCGGGCGCCCGAGAAGCCTA ATTTGCCAAATAATC | basics | no | no | yes | no | no | no | no |
| 1[385]3 [398] | CATGTTAAATGAATACCGCCA CCCTCAG | basics | no | no | yes | no | no | no | no |
| 0[1042]3 [1035] | CTCGTTAGCCCTTCGGAAGC GCATTAGAGTCCAGA | basics | no | no | yes | no | no | no | no |
| 1[196]3 [209] | AGGAAGTCAGCTTGCCTATTT CGGAACC | basics | no | no | yes | no | no | no | no |
| 1[847]3 [860] | AAGAGCAATATTCCGAAAAAG CCTGTTT | basics | no | no | yes | no | no | no | no |
| 1[406]3 [419] | GGCGCAGTCGTCTTACCCTC AGAGCCAC | basics | no | no | yes | no | no | no | no |
| 1[805]3 [818] | TAATGCACTGATTGTAAGGCG TTAAATA | basics | no | no | yes | no | no | no | no |
| 0[1063]3 [1056] | GAGCACGAGAGAGTGAGAGA ATAACATAAACATGT | basics | no | no | yes | no | no | no | no |
| 1[259]3 [272] | AAGAGGCGCTCCAAAGGATT AGGATTAG | basics | no | no | yes | no | no | no | no |
| 0[664]3 [657] | GCTTAGATAACGCCATGGTTT ACCAGCGCTCCGGC | basics | no | no | yes | no | no | no | no |
| 1[763]3 [776] | AGAAAGAACCTACCTGACCTA AATTTAA | basics | no | no | yes | no | no | no | no |
| 0[790]3 [783] | AAGACTTCCTGTGTAAGACTC CTTATTATGGTTTG | basics | no | no | yes | no | no | no | no |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 0[748]3[741] | CCAGACCCGGGTACCATACATAAAGGTGCAAATAT | basics | no | no | yes | no | no | no | no |
| 1[469]3[503] | TGTACAGACTACAAACACTGAGTTTCGTCAATAAATCAATATATGTGAG | basics | no | no | yes | no | no | no | no |
| 0[685]3[678] | AAGAGGTCACGACGCACAATCAATAGAAATAACTA | basics | no | no | yes | no | no | no | no |
| 0[160]3[153] | TTCTAGCCCGGTTGCCTCATTAAAGCCAGGTCAGT | basics | no | no | yes | no | no | no | no |
| 0[706]3[699] | CCTTTAACCAGTGCCACGGAATAAGTTTTGCAAAT | basics | no | no | yes | no | no | no | no |
| 0[769]3[762] | TAATTCGTAATCATTGTTAGCAAACGTACATCTTC | basics | no | no | yes | no | no | no | no |
| 0[349]3[342] | CGGTTGTATGTGAGAATCAAAATCACCGGAATAGG | basics | no | no | yes | no | no | no | no |
| 1[364]3[377] | GTCGAAATTTGCTATTTAGTACCGCCAC | basics | no | no | yes | no | no | no | no |
| 0[727]3[720] | ACAGGTCAGGTCGAATAAAAGAAACGCAAAGAACG | basics | no | no | yes | no | no | no | no |
| 0[433]3[426] | TAGCATTTGGGCGCGTTTGCCTTTAGCGCACCCTC | basics | no | no | yes | no | no | no | no |
| 0[1126]3[1119] | GTAACCAGGTTCCGTCCCAATCCAAATAAATAATA | basics | no | no | yes | no | no | no | no |
| 1[784]3[797] | TTTAGGACTGAATAAAATACCGACCGTG | basics | no | no | yes | no | no | no | no |
| 1[511]3[524] | TAATCTTCATTTGACCTTGCTTCTGTAA | basics | no | no | yes | no | no | no | no |
| 0[286]3[279] | AAGGATATAGGAACAACCGCCACCCTCACGGGGTT | basics | no | no | yes | no | no | no | no |
| 0[832]3[825] | AAGCAAACGAGCCGAAACGCAATAATAAAGAATAA | basics | no | no | yes | no | no | no | no |
| 0[1084]3[1077] | GCGTACTCACGCTGATGAAAATAGCAGCACGCGCC | basics | no | no | yes | no | no | no | no |
| 1[175]3[188] | AGGACTAGCCGACAATAAACAGTTAATG | basics | no | no | yes | no | no | no | no |
| 0[1147]3[1140] | AGTGTAGCCTTATAAATAAACAGCCATAACGAGCA | basics | no | no | yes | no | no | no | no |
| 5[98]0[98] | AAACAAGAGAATCGTACAAAGGCTATCA | basics | no | no | yes | no | no | no | no |
| 1[532]3[545] | ATTCATTATTAATTCTATTAATTAATTT | basics | no | no | yes | no | no | no | no |
| 0[811]3[804] | AAAGATTCTCACAACCCAAAAGAACTGGTGATAAA | basics | no | no | yes | no | no | no | no |
| 1[238]3[251] | GAAGGCATGTATCGAGGCTGAGACTCCT | basics | no | no | yes | no | no | no | no |
| 0[118]4[112] | AGAGATCATGAACGCGTTCCA | basics | no | no | yes | no | no | no | no |
| 1[448]3[461] | TGAAAGACACAGACAATAGGAACCCATG | basics | no | no | yes | no | no | no | no |
| 0[139]3[132] | CGGAGAGAGCATGTAAGCGCAGTCTCTGACTGGTA | basics | no | no | yes | no | no | no | no |

|  |  |  | FIG. | | | | | |
|---|---|---|---|---|---|---|---|---|
| Oligo Position | Sequence | Staple Type | 1 | 7 | 8 | 9A,B | 9C,D | 10A,B | 10C,D |
| 0[853]3[846] | TACCCTGAAAGCCTGTTACCAGAAGGAAATTACTA | basics | no | no | yes | no | no | no | no |
| 1[574][587] | AATAAGGCTGAGCATAGCTTAGATTAAG | basics | no | no | yes | no | no | no | no |
| 0[895][888] | GTTCAGAGCGTTGCCCGAAGCCCTTTTTATTCTTA | basics | no | no | yes | no | no | no | no |
| 0[1189]3[1182] | GAAGGGAGTTCCAGCGCTAACGAGCGTCATCATTC | basics | no | no | yes | no | no | no | no |
| 1[301]3[314] | AGCGATTGCGAATAAGTGCCGTCGAGAG | basics | no | no | yes | no | no | no | no |
| 0[244]3[237] | TGCCTGATTCGCATAACCACCACCAGAGTATTAAG | basics | no | no | yes | no | no | no | no |
| 0[1210]3[1203] | CCGGCGACCACTATTTTTATCCTGAATCAAACCAA | basics | no | no | yes | no | no | no | no |
| 1[217][230] | TAAATATTTCGAGCTGAAACATGAAAG | basics | no | no | yes | no | no | no | no |
| 1[553][566] | AACAAAGAACAAACGAATCCTTGAAAAC | basics | no | no | yes | no | no | no | no |
| 1[658]3[671] | ATTACCTGGGAGAATTAGGTTGGGTTAT | basics | no | no | yes | no | no | no | no |
| 1[595][608] | AAACACCCGAATTAGAAGAGTCAATAGT | basics | no | no | yes | no | no | no | no |
| 1[1015]3[1028] | TTAACCGAGAGCCGGGTAAAGTAATTCT | basics | no | no | yes | no | no | no | no |
| 1[679]3[692] | AACTGGCAGTAACATATGTAAATGCTGA | basics | no | no | yes | no | no | no | no |
| 1[616]3[629] | ATTGGGCAGTTACATCAAAATCATAGGT | basics | no | no | yes | no | no | no | no |
| 1[637]3[650] | TTTCAACGCCTGATACTACCTTTTTAAC | basics | no | no | yes | no | no | no | no |
| 1[1141]3[1154] | ACGCTCAATCACCTTGTAGAAACCAATC | basics | no | no | yes | no | no | no | no |
| 0[874]3[867] | ATAAATCGTGAGCTGTAAGCAGATAGCCAGTATCA | basics | no | no | yes | no | no | no | no |
| 0[1105]3[1098] | CTTAATGGCGAAAATTTTTTGTTTAACAGATAAG | basics | no | no | yes | no | no | no | no |
| 0[916]3[909] | CCCCCTCTTCCAGTGAAATAGCAATAGCACGCTCA | basics | no | no | yes | no | no | no | no |
| 0[538][531] | TAGTTTGGAAACCATAGAGCCAGCAAAAATCGTCG | basics | no | no | yes | no | no | no | no |
| 0[937][930] | CGTCATATGCCAGCATAATAAGAGCAAGTTGAGAA | basics | no | no | yes | no | no | no | no |
| 1[133]3[146] | GACAGCATTCGGTCATAAGTTTTAACGG | basics | no | no | yes | no | no | no | no |
| 0[454][447] | CATCAATTCTGCCAAATCAGTAGCGACACAAGCCC | basics | no | no | yes | no | no | no | no |
| 0[958][951] | TAGCGTCGGCCAACACAAGAATTGAGTTAACGCCA | basics | no | no | yes | no | no | no | no |
| 0[622][615] | GTTTTAAAGCTGGCATTGAGGGAGGGAAGAATTTA | basics | no | no | yes | no | no | no | no |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 0[307]3 [300] | GAGAAGCTTCGCGTCCTCAG AGCCGCCAGCGGATA | basics | no | no | yes | no | no | no | no |
| 1[721]3 [734] | TACGTTAGAAATTGCGAGAAA ACTTTTT | basics | no | no | yes | no | no | no | no |
| 1[154]3 [167] | GCAACGGCGCCCACGCCTTG AGTAACAG | basics | no | no | yes | no | no | no | no |
| 1[742]3 [755] | CGGAACATGCACGTATTTTAG TTAATTT | basics | no | no | yes | no | no | no | no |
| 1[1099] 3[1112] | ATATCCACTGGTCATCCTGAA CAAGAAA | basics | no | no | yes | no | no | no | no |
| 0[370]3 [363] | CCTCAGATCGGATTTAGCGTT TGCCATCCAGGAGG | basics | no | no | yes | no | no | no | no |
| 0[559]3 [552] | AATTCTGCGCCATTCGACTTG AGCCATTTCCCTTA | basics | no | no | yes | no | no | no | no |
| 1[973]3 [986] | TCAGTGAAGACTTTATTTTCG AGCCAGT | basics | no | no | yes | no | no | no | no |
| 3[100]3 [125] | CATGGCTTTTGATGATACAGG AGTGT | basics | no | no | yes | no | no | no | no |
| 4[419]1 [426] | TCAGACTCACGTTGGTGTAGA AACATCCATCATAA | basics | no | no | yes | no | no | no | no |
| 4[461]1 [468] | GCACCGTGTTTGAGGGGACG AAGCTGAATGAACGG | basics | no | no | yes | no | no | no | no |
| 2[1140] 0[1127] | TGCTGAACCTCAAATTGCAAC GCTGCGC | basics | no | no | yes | no | no | no | no |
| 2[405]0 [392] | TCCAGACGTTAGTACTTAGCC AAAGAAT | basics | no | no | yes | no | no | no | no |
| 4[692]1 [699] | ATTTTGTTTGTAAAACGACGG TTGCTCCACCAGTC | basics | no | no | yes | no | no | no | no |
| 4[1070] 1[1077] | CTTTACATGCAGCAAGCGGTC ATGGTTGAGAACTC | basics | no | no | yes | no | no | no | no |
| 4[1259] 1[1266] | TTTTGAAATCAGGGCGATGGC AAGCACTACCCTTC | basics | no | no | yes | no | no | no | no |
| 2[552]0 [539] | ATCAAGAAAACAAAACCCAAA GTAGATT | basics | no | no | yes | no | no | no | no |
| 4[167]1 [174] | AATAAATATAATCAGAAAAGC ATGATATGGCTTTG | basics | no | no | yes | no | no | no | no |
| 5[959]0 [959] | GCGCGGGGAGAGGCGAATCC TGAGAAGA | basics | no | no | yes | no | no | no | no |
| 2[1245] 0[1232] | CCACCAGCAGAAGAAAGGGA CCCCCCGA | basics | no | no | yes | no | no | no | no |
| 2[1077] 0[1064] | AGGAATTGAGGAAGGAGTAG ACTTTGAC | basics | no | no | yes | no | no | no | no |
| 2[783]0 [770] | ATGGAAGGGTTAGATTCATCA CGCGTTT | basics | no | no | yes | no | no | no | no |
| 2[195]0 [182] | ATACCGATAGTTGCAAGACTT AAATCAC | basics | no | no | yes | no | no | no | no |
| 4[314]1 [321] | CCGCCTCCTGGCCTTCCTGTA TAATACTGCGCGAA | basics | no | no | yes | no | no | no | no |
| 4[1238] 1[1245] | TTAGTTGTCAAAGGGCGAAAA AAGGGAGATTCTGG | basics | no | no | yes | no | no | no | no |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 4[1028]1[1035] | CGGGAGAGGCAACAGCTGATTGAATCAGAATACTT | basics | no | no | yes | no | no | no | no |
| 4[734]1[741] | GCAACATCTCTAGAGGATCCCGGAAGCAGAACTAA | basics | no | no | yes | no | no | no | no |
| 2[846]0[833] | TGATTATCAGATGATTACGAGTAGTCAG | basics | no | no | yes | no | no | no | no |
| 4[881]1[888] | AAGAAAAAACTCACATTAATTAAACGAGGACGATA | basics | no | no | yes | no | no | no | no |
| 4[377]1[384] | CCCTTATCTCCGTGGGAACAAATTAAGCCCTGCTC | basics | no | no | yes | no | no | no | no |
| 4[482]1[489] | CCAATGAATCGGCCTCAGGAATATATTTGCATAGG | basics | no | no | yes | no | no | no | no |
| 2[1224]0[1211] | GAGGTGAGGCGGTCCAGTCACGGGAAAG | basics | no | no | yes | no | no | no | no |
| 2[741]0[728] | AAAACAGAAATAAAATAAAACAACTCCA | basics | no | no | yes | no | no | no | no |
| 2[951]0[938] | ATTAAATCCTTTGCGTAATAGGCGGAAT | basics | no | no | yes | no | no | no | no |
| 4[230]1[237] | CCGCCGCATATTTTGTTAAAAGTAATGTCCACTAC | basics | no | no | yes | no | no | no | no |
| 4[440]1[447] | GAATCAAATCGTAACCGTGCATCTACTACCAACTT | basics | no | no | yes | no | no | no | no |
| 4[1175]1[1182] | TTTCCAGTAGGGTTGAGTGTTAGAAAGCCGTCTGA | basics | no | no | yes | no | no | no | no |
| 4[587]1[594] | TTCATTAAGGGCGATCGGTGCTCTGGAATGACGAG | basics | no | no | yes | no | no | no | no |
| 4[209]1[216] | GGTTGAGATATTTAAATTGTAAAAAGGGAAACGGG | basics | no | no | yes | no | no | no | no |
| 2[342]0[329] | CGGAGTGAGAATAGACAACGGACATTAT | basics | no | no | yes | no | no | no | no |
| 4[1007]1[1014] | CTGAACATTTCTTTTCACCAGAGGAGGCACGCAAA | basics | no | no | yes | no | no | no | no |
| 4[272]1[279] | GAGCCACCATTTTTTAACCAAAAAATTTTACACTA | basics | no | no | yes | no | no | no | no |
| 2[1287]0[1274] | ACTGATAGCCCTAAAAAGCGTGTCGAGG | basics | no | no | yes | no | no | no | no |
| 4[1217]1[1224] | GCTACAATAAAGAACGTGGACCTTGACGACGACCA | basics | no | no | yes | no | no | no | no |
| 2[510]0[497] | ATTACCTTTTTTAAACCTTCAATAACCT | basics | no | no | yes | no | no | no | no |
| 2[132]2[115] | GCTGAGGCTTGCAGGGAG | basics | no | no | yes | no | no | no | no |
| 2[1014]0[1001] | TCAATAGATAATACGTCCATCCGATTAA | basics | no | no | yes | no | no | no | no |
| 4[503]1[510] | TTAGCAACTCCAGCCAGCTTTATGGTCATCAAGAG | basics | no | no | yes | no | no | no | no |
| 2[384]0[371] | TTTCTGTATGGGATTCCGCGAAATAAAG | basics | no | no | yes | no | no | no | no |
| 4[986]1[993] | TTGAGCGGTATTGGGCGCCAGTTAGACAGAGTAAA | basics | no | no | yes | no | no | no | no |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 4[125]1[132] | AATTTACGTAATCGTAAAACTGGTAGCTAGCGAAA | basics | no | no | yes | no | no | no | no |
| 4[671]1[678] | AATTCATAGGGTTTTCCCAGTCATTTTTTTTAAG | basics | no | no | yes | no | no | no | no |
| 2[888]0[875] | ACAAAGAAACCACCACCAGACAATGACC | basics | no | no | yes | no | no | no | no |
| 4[566]1[573] | CCGTCACCAGGCTGCGCAACTAACAGTTTTCAGTG | basics | no | no | yes | no | no | no | no |
| 1[952]1[972] | TTTAGACTGGTGTTTTTATAA | basics | no | no | yes | no | no | no | no |
| 2[300]0[287] | ATAATTTTTTCACGCATCTTTTCAACGC | basics | no | no | yes | no | no | no | no |
| 2[1182]0[1169] | CGCTGAGAGCCAGCGCTCAATGAAAGGA | basics | no | no | yes | no | no | no | no |
| 2[174]0[161] | ATGACAACAACCATCTACAGATCAACCG | basics | no | no | yes | no | no | no | no |
| 4[1154]1[1161] | GTTACAAAATCAAAGAATAGCTAGGGCACCTACA | basics | no | no | yes | no | no | no | no |
| 2[1056]0[1043] | AAAATATCTTTAGGTAGTAATTGCTTTC | basics | no | no | yes | no | no | no | no |
| 2[930]0[917] | TTATTAATTTTAAAAAGAAGATTGAAT | basics | no | no | yes | no | no | no | no |
| 4[335]1[342] | GAACCAGTTCATCAACATTAAACCAAAAAGATTTG | basics | no | no | yes | no | no | no | no |
| 4[524]1[531] | TCACCAGCGCTTCTGGTGCCGACCATTAACCGGAT | basics | no | no | yes | no | no | no | no |
| 1[490]0[476] | CTGGCTGTGGAAACAGTACCCAGTACAAACCAGGCTCATTTG | basics | no | no | yes | no | no | no | no |
| 4[1091]1[1098] | GTCAAAGTTTGCCCCAGCAGCGCCGCTGCTGGTA | basics | no | no | yes | no | no | no | no |
| 2[594]0[581] | TTCATTTCAATTACCTTGCCCGTTTCAT | basics | no | no | yes | no | no | no | no |
| 2[762]0[749] | ATATCAAAATTATTACATTATAAGCGAA | basics | no | no | yes | no | no | no | no |
| 4[629]1[636] | TCAACCGGAAAGGGGGATGTGCTGTAGCGGTTTAA | basics | no | no | yes | no | no | no | no |
| 2[699]0[686] | TCAGATGAATATACTCATTATTTTTGAT | basics | no | no | yes | no | no | no | no |
| 4[1133]1[1140] | TTATTTAAAATCGGCAAAATCCGGTCACAGGAAAA | basics | no | no | yes | no | no | no | no |
| 2[426]0[413] | GATCTAAAGTTTTGACGGTCAAATAAAT | basics | no | no | yes | no | no | no | no |
| 2[363]0[350] | AACAACTTTCAACAGCCTGATGCTAAAT | basics | no | no | yes | no | no | no | no |
| 2[1035]0[1022] | ACAACTAATAGATTTTGTAGCAGCGGGA | basics | no | no | yes | no | no | no | no |
| 1[115]0[119] | TCACCCTCAGCATTTTTG | basics | no | no | yes | no | no | no | no |
| 2[279]0[266] | TCTCCAAAAAAAAGAAAGAATTAGAAC | basics | no | no | yes | no | no | no | no |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 4[818]1[825] | CGGAATATTCCACACAACATAGCGGATTAACGCCA | basics | no | no | yes | no | no | no | no |
| 4[776]1[783] | CGCAGTAGGTCATAGCTGTTTCAAATATGTTGAGA | basics | no | no | yes | no | no | no | no |
| 2[468]0[455] | CGCCTGTAGCATTCGGACAGAAAGGTGG | basics | no | no | yes | no | no | no | no |
| 4[944]1[951] | AAGCCCATGCATTAATGAATCCAATACTTAAAATG | basics | no | no | yes | no | no | no | no |
| 4[839]1[846] | ACCGAGGGAAGCATAAAGTGTACTATTAGCATAGT | basics | no | no | yes | no | no | no | no |
| 4[146]1[153] | GAATGGACAATCATATGTACCTGATAAAGAGGGTA | basics | no | no | yes | no | no | no | no |
| 4[860]1[867] | GAACAAGGGGTGCCTAATGAAAAAATCCATAACC | basics | no | no | yes | no | no | no | no |
| 4[755]1[762] | GAAAATACGAGCTCGAATTCGAGCTTCATACAGGT | basics | no | no | yes | no | no | no | no |
| 2[636]0[623] | TGCTTTGAATACCATTGAGATTCAACAT | basics | no | no | yes | no | no | no | no |
| 2[153]0[140] | GCATAACCGATATATCGGAACTTAATGC | basics | no | no | yes | no | no | no | no |
| 2[657]0[644] | ACAATAACGGATTCTTTAATCTGCTGAA | basics | no | no | yes | no | no | no | no |
| 4[293]1[300] | CCCTCAGGCCATCAAAAATAACTTTATTGACCCCC | basics | no | no | yes | no | no | no | no |
| 4[650]1[657] | CCAAAGAGCGATTAAGTTGGGGCTTAATATTGTGA | basics | no | no | yes | no | no | no | no |
| 2[321]0[308] | CAACTAAAGGAATTATACCAATTTGCGG | basics | no | no | yes | no | no | no | no |
| 2[1203]0[1190] | ACACCGCCTGCAACTATTTACGAGAAAG | basics | no | no | yes | no | no | no | no |
| 2[972]4[959] | ACAAACAATTCGACAACTCGTACATGTAATTTAGGATAACCC | basics | no | no | yes | no | no | no | no |
| 2[993]0[980] | GATTTAGAAGTATTGGCCACCGGAACGG | basics | no | no | yes | no | no | no | no |
| 2[825]0[812] | TCATCAATATAATCGATACATGCATCAA | basics | no | no | yes | no | no | no | no |
| 4[1112]1[1119] | AGAAACGTCCTGTTTGATGGTCCACACCATTACCG | basics | no | no | yes | no | no | no | no |
| 2[573]0[560] | AAAGAAGATGATGACTGCTCAGATTCCC | basics | no | no | yes | no | no | no | no |
| 4[713]1[720] | AAGACACCAAGCTTTGCCTGCAGGATTAAAAAATC | basics | no | no | yes | no | no | no | no |
| 2[258]0[245] | AAGGAGCCTTTAATCCAACCTAATGCAA | basics | no | no | yes | no | no | no | no |
| 2[531]0[518] | ACATTTAACAATTTGACAAGAGATACAT | basics | no | no | yes | no | no | no | no |
| 4[398]1[405] | TCGGCATATTGACCGTAATGGGCAAGGCGGAACGA | basics | no | no | yes | no | no | no | no |
| 4[1196]1[1203] | TTACCAATTTGGAACAAGAGTACGTGGCATTGGCA | basics | no | no | yes | no | no | no | no |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 2[678]0 [665] | GTACCTTTTACATCTATGCGA GCGGATG | basics | no | no | yes | no | no | no | no |
| 4[902]1 [909] | TATCTTAGCTCACTGCCCGCT AAATGCTGAGAGGC | basics | no | no | yes | no | no | no | no |
| 2[804]0 [791] | TTTGGATTATACTTATACCACA GCCCGA | basics | no | no | yes | no | no | no | no |
| 2[216]0 [203] | GTGAATTTCTTAAATTCCATTT GAGAAA | basics | no | no | yes | no | no | no | no |
| 2[909]0 [896] | GTAACATTATCATTAAATAGCT TAAACA | basics | no | no | yes | no | no | no | no |
| 4[797]1 [804] | CATGATTGAAATTGTTATCCG AAGAGGAATTCAAC | basics | no | no | yes | no | no | no | no |
| 2[720]0 [707] | CGTAGATTTTCAGGTGGGAAG GAGAGTA | basics | no | no | yes | no | no | no | no |
| 2[867]0 [854] | GCGGAATTATCATCACACTAT AGGTCTT | basics | no | no | yes | no | no | no | no |
| 2[447]0 [434] | AGCCCTCATAGTTAGAACTGA ATAGTAG | basics | no | no | yes | no | no | no | no |
| 4[251]1 [258] | CCACCAGTAAATTTTTGTTAAT ATTTTAAAAACGA | basics | no | no | yes | no | no | no | no |
| 4[1049] 1[1056] | AAAACAGACCGCCTGGCCCT GTATAACGAACATCA | basics | no | no | yes | no | no | no | no |
| 4[923]1 [930] | AAACAATCGGGAAACCTGTCG AATATTCTTTTGCC | basics | no | no | yes | no | no | no | no |
| 4[356]1 [363] | TTTTCATCGAGTAACAACCCG GCATAAAAAATTGT | basics | no | no | yes | no | no | no | no |
| 2[1098] 0[1085] | GTTGGCAAATCAACCGGCCTT ACAGGGC | basics | no | no | yes | no | no | no | no |
| 2[237]0 [224] | GTTTATCAGCTTGCCGTAATG GTAGGTA | basics | no | no | yes | no | no | no | no |
| 4[188]1 [195] | TGGCCTTACAGGAAGATTGTA GACAGTCTTTCATG | basics | no | no | yes | no | no | no | no |
| 2[1119] 0[1106] | CCCTCAATCAATATGAACAAT CGCCGCG | basics | no | no | yes | no | no | no | no |
| 2[1266] 0[1253] | CCATTAAAAATACCAGATAGA AAATCGG | basics | no | no | yes | no | no | no | no |
| 2[615]0 [602] | AAATCGCGCAGAGGAGAACG AACTAAAG | basics | no | no | yes | no | no | no | no |
| 4[545]1 [552] | TGGGAATGGCAAAGCGCCAT TCGAACGATCAACGT | basics | no | no | yes | no | no | no | no |
| 4[608]1 [615] | GGTAAATTTCGCTATTACGCC ATATGCAGTAGTAA | basics | no | no | yes | no | no | no | no |
| 2[1161] 0[1148] | GAAAAATCTAAAGCTGGAAAT GCTGGCA | basics | no | no | yes | no | no | no | no |
| 2[1315] 1[1315] | taagtgagacccgtacatatTTTGGCT ATTAGTCTTTAACAGACAATAT TTTTGAATTtaagtgagacccgtacat at | A655 Marker Extensions | no | no | yes | no | no | no | no |
| 4[1280] 5[1296] | taagtgagacccgtacatatAACCTCC GTGAACCATCACCCAAATCTTt aagtgagacccgtacatat | A655 Marker Extensions | no | no | yes | no | no | no | no |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 0[1296] 1[1287] | taagtgagacccgtacatatTTAAGTTT TTTGGGAAGAATaaagtgagacc cgtacatat | A655 Marker Extensions | no | no | yes | no | no | no | no |
| 4[1310] 3[1287] | taagtgagacccgtacatatTTTTCTAA GAACGCGAGGCGTTTTAGCG ATCAGATtaagtgagacccgtacatat | A655 Marker Extensions | no | no | yes | no | no | no | no |
| 1[1288] 3[1310] | taagtgagacccgtacatatCGTGGCA TGCGCGAATAGAAGGCTTATC CGGTATTtaagtgagacccgtacatat | A655 Marker Extensions | no | no | yes | no | no | no | no |
| 1[1246] 3[1259] | taagtgagacccgtacatatCCAACAG GAACGAATCGTAGGAATCATT Ttaagtgagacccgtacatat | A655 Marker Extensions | no | no | yes | no | no | no | no |
| 1[1204] 3[1217] | taagtgagacccgtacatatGATTCAC AGTATTAGTACCGCACTCATC Ttaagtgagacccgtacatat | A655 Marker Extensions | no | no | yes | no | no | no | no |
| 1[1267] 3[1280] | taagtgagacccgtacatatTGACCTG AACATCGCCAATAGCAAGCAA Ttaagtgagacccgtacatat | A655 Marker Extensions | no | no | yes | no | no | no | no |
| 0[1231] 3[1224] | taagtgagacccgtacatatTTTAGAG TCCAACGCTATTTTGCACCCA GAGAACATtaagtgagacccgtacat at | A655 Marker Extensions | no | no | yes | no | no | no | no |
| 1[1225] 3[1238] | taagtgagacccgtacatatGTAATAA TAAAACAAGCAAGCCGTTTTT Ttaagtgagacccgtacatat | A655 Marker Extensions | no | no | yes | no | no | no | no |
| 0[1273] 3[1266] | taagtgagacccgtacatatTGCCGTA CCACTACCGACTTGCGGGAG GACCGCGCTtaagtgagacccgtac atat | A655 Marker Extensions | no | no | yes | no | no | no | no |
| 0[1252] 3[1245] | taagtgagacccgtacatatAACCCTA ACCGTCTGCCTTAAATCAAGA ATTTTCATtaagtgagacccgtacatat | A655 Marker Extensions | no | no | yes | no | no | no | no |

High Torque Extension

| Oligo Position | Sequence | Staple Type | FIG. 1 | 7 | 8 | 9A,B | 9C,D | 10A,B | 10C,D |
|---|---|---|---|---|---|---|---|---|---|
| 12[447]9 [440] | TTTACGAACGCCTGCTTCA AAGCGAACCTCAAATC | basics | no | no | no | yes | yes | yes | yes |
| 11[315]9 [328] | GACCAGTCGTTAGAGGGAG AAGCCTTTA | basics | no | no | no | yes | yes | yes | yes |
| 11[336]9 [349] | TCTGGCCGCACGTAGCAAG GATAAAAAT | basics | no | no | no | yes | yes | yes | yes |
| 11[672]9 [685] | TAGGAGCAGTTTGGCGTTA ATATTTTGT | basics | no | no | no | yes | yes | yes | yes |
| 12[1077] 9[1070] | GAGTGAACGAAATCTATTC ATTACCCAAACGCCAG | basics | no | no | no | yes | yes | yes | yes |
| 12[615]9 [608] | AGGCAGAAATAATTTATTCA TTGAATCCGTACCCC | basics | no | no | no | yes | yes | yes | yes |
| 12[636]9 [629] | AACAACGATCTCCAATACT GCGGAATCGAAAGCCC | basics | no | no | no | yes | yes | yes | yes |
| 11[609]9 [622] | ATATCTGCTATCAGGGTTG ATAATCAGA | basics | no | no | no | yes | yes | yes | yes |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 12[657]9[650] | TAATTGAAAAGGAGGTTTAGACTGGATATTGTATA | basics | no | no | no | yes | yes | yes | yes |
| 12[1035]9[1028] | TTTTCCCAAAGTACGAATAAGGCTTGCCCAACTGT | basics | no | no | no | yes | yes | yes | yes |
| 11[399]9[412] | TTTTTGAAACCACCTAAAGATTCAAAAG | basics | no | no | no | yes | yes | yes | yes |
| 1[315]3[328] | GAGGTTTAGTACCGTCTGAAAGGTAATA | basics | no | no | no | yes | yes | yes | yes |
| 12[195]9[188] | TATTTTGCCACGGAGGTCAATAACCTGTTAATAGT | basics | no | no | no | yes | yes | yes | yes |
| 12[804]9[797] | TAATGGTAAAGGCCCTAATGCAGATACAATTAAAT | basics | no | no | no | yes | yes | yes | yes |
| 11[840]9[853] | CACCAGACGGGCAAGGCGGATTGACCGT | basics | no | no | no | yes | yes | yes | yes |
| 11[630]9[643] | CAACAGTCGTCAAACAAAAACAGGAAGA | basics | no | no | no | yes | yes | yes | yes |
| 11[966]9[979] | TATTTGCGCGCTCAGGCACCGCTTCTGG | basics | no | no | no | yes | yes | yes | yes |
| 5[154]1[175] | GCTAATATCAGAGAGATAACCCTGGCATAATAATAA | basics | no | no | no | yes | yes | yes | yes |
| 12[1014]9[1007] | AACATAGCGATTATGAAACACCAGAACGCCATTCG | basics | no | no | no | yes | yes | yes | yes |
| 11[882]9[895] | ATGATGGGCGTATTGGCGCATCGTAACC | basics | no | no | no | yes | yes | yes | yes |
| 12[699]9[692] | CAAATTCGGTGAATCTTTTGCAAAAGAATAAAATT | basics | no | no | no | yes | yes | yes | yes |
| 12[384]9[377] | ATTAAACATAGCAAGCTCCTTTTGATAATAAATGC | basics | no | no | no | yes | yes | yes | yes |
| 12[909]9[902] | TATATAAGAAGTTTCAGGACGTTGGGAAGTGCATC | basics | no | no | no | yes | yes | yes | yes |
| 12[720]9[713] | TTTAGTAGATACCGAAAAACCAAAATAGGTTAAAT | basics | no | no | no | yes | yes | yes | yes |
| 3[329]0[336] | AGTTTTACAGGAGGAGCCGCCACCCTCACGTCACC | basics | no | no | no | yes | yes | yes | yes |
| 12[678]9[671] | CCAACGCGGTTTATCAGAGGGGGTAATATTGTAAA | basics | no | no | no | yes | yes | yes | yes |
| 11[735]9[748] | TATTAGACGAAATCGGAACGCCATCAAA | basics | no | no | no | yes | yes | yes | yes |
| 11[819]9[832] | CATTTTGTCACCGCGGATTCTCCGTGGG | basics | no | no | no | yes | yes | yes | yes |
| 5[251]0[248] | CCCCCTTATTTCATCGGCA | basics | no | no | no | yes | yes | yes | yes |
| 8[349]3[342] | TTAGAGCGAGCCATCCGGAAAGAACCGCGCCGCCAGCATTGAACGGGGT | basics | no | no | no | yes | yes | yes | yes |
| 7[125]12[132] | TTTATGAAAAAACGTAGAAAATAGCGTCTTTCCATTT | basics | no | no | no | yes | yes | yes | yes |
| 12[888]9[881] | TGATGCAGACTAAACTACGTTAATAAAAGTAGATG | basics | no | no | no | yes | yes | yes | yes |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 1[336]3[349] | CAGAACCGCCACCCGCCTATTCAGTGCC | basics | no | no | no | yes | yes | yes | yes |
| 12[741]9[734] | ATAATTAAATGACACCTCGTTTACCAGAACCAATA | basics | no | no | no | yes | yes | yes | yes |
| 11[252]9[265] | CTACATTCGCCAGAAGCCTCAGAGCATA | basics | no | no | no | yes | yes | yes | yes |
| 12[237]9[230] | GACTTGCTATGGTTAACGAGTAGATTTAGCAAAGA | basics | no | no | no | yes | yes | yes | yes |
| 11[273]9[286] | TCTGAAAGGATTTTATCGGTTGTACCAA | basics | no | no | no | yes | yes | yes | yes |
| 11[987]9[1000] | TAAAGAACTAACTCAACCAGGCAAAGCG | basics | no | no | no | yes | yes | yes | yes |
| 8[142]9[139] | TGTTTAACGTCAAAATTTTTTCATATTATT | basics | no | no | no | yes | yes | yes | yes |
| 0[132]1[146] | GCAGCCTTTACATTTTTGAGAGAATAACATAAACAAAGTTACC | basics | no | no | no | yes | yes | yes | yes |
| 3[350]0[357] | TTGAGTACAGAGCCCACCCTCAGAGCCATACCATT | basics | no | no | no | yes | yes | yes | yes |
| 11[546]9[559] | CAGCAGCCCGTAAAGGAGCAAACAAGAG | basics | no | no | no | yes | yes | yes | yes |
| 12[216]9[209] | CCTTAAATCACAATCATTAGATACATTTCCAATAA | basics | no | no | no | yes | yes | yes | yes |
| 11[420]9[433] | TTAATGCTGTAGCGAAGGCCGGAGACAG | basics | no | no | no | yes | yes | yes | yes |
| 11[924]9[937] | ACTTCTGGCTGCATACAGTATCGGCCTC | basics | no | no | no | yes | yes | yes | yes |
| 12[258]9[251] | AGGCGTTACAAAAGCAGTTGATTCCCAAGCAATAA | basics | no | no | no | yes | yes | yes | yes |
| 11[462]9[475] | TACCGAAAGGGAAGCGTTCTAGCTGATA | basics | no | no | no | yes | yes | yes | yes |
| 12[174]8[168] | TTTATCCTATAAAATATTTTC | basics | no | no | no | yes | yes | yes | yes |
| 11[1050]9[1063] | CATCGGGAATTCCAGCCTCTTCGCTATT | basics | no | no | no | yes | yes | yes | yes |
| 0[385]5[378] | TTTTTTTCAGCAGTAGCACCATCCACCCTCAGAGTTT | basics | no | no | no | yes | yes | yes | yes |
| 11[861]9[874] | CATCATATTTTTCTTAGGTCACGTTGGT | basics | no | no | no | yes | yes | yes | yes |
| 12[1056]9[1049] | TAAATCGTCATCGCTAACAAAGCTGCTCGGTGCGG | basics | no | no | no | yes | yes | yes | yes |
| 11[441]9[454] | CTAAAACGGGCGCTACCATCAATATGAT | basics | no | no | no | yes | yes | yes | yes |
| 11[945]9[958] | TAGAACCGTCGGGATCGCACTCCAGCCA | basics | no | no | no | yes | yes | yes | yes |
| 11[378]9[391] | GAATACGTAATGCGAATGCCTGAGTAAT | basics | no | no | no | yes | yes | yes | yes |
| 12[573]9[566] | ACCGACAGCGGAGTACGAGAATGACCATAATCGAT | basics | no | no | no | yes | yes | yes | yes |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 11[483]9[496] | AAGATAAGGCGAACGCCGGAGAGGGTAG | basics | no | no | no | yes | yes | yes | yes |
| 12[594]9[587] | AGTAATAACAACTAATGCTTTAAACAGTAAACTAG | basics | no | no | no | yes | yes | yes | yes |
| 8[307]3[300] | TTTAAATGGAAATTTCAGTAGGAGCCACGCCTTGATATTCACATGGCTT | basics | no | no | no | yes | yes | yes | yes |
| 1[257]2[254] | GTGCCGTCGTTTGCTCAGTAC | basics | no | no | no | yes | yes | yes | yes |
| 11[504]9[517] | GGTCAGTTAGAGCTTGAGAGATCTACAA | basics | no | no | no | yes | yes | yes | yes |
| 12[762]9[755] | ATAAGAACGCATAATAAGAGCAACACTAAATAATT | basics | no | no | no | yes | yes | yes | yes |
| 12[930]9[923] | AACCTCCAAATACGGAACTGGCTCATTAGACGACG | basics | no | no | no | yes | yes | yes | yes |
| 0[146]5[146] | AGTATGTTAGCATAAAAGTCAGAGGGTA | basics | no | no | no | yes | yes | yes | yes |
| 12[783]9[776] | GTGTGATCGCTGAGAAAAGGAATTACGACTGTAGC | basics | no | no | no | yes | yes | yes | yes |
| 7[147]0[154] | ACATACATAAAGGTACTCCTT | basics | no | no | no | yes | yes | yes | yes |
| 12[825]9[818] | TTTCATCGTCACCCATTTAGGAATACCAACCCGTC | basics | no | no | no | yes | yes | yes | yes |
| 12[846]9[839] | TTTCAAACAGCATCTAGAAAGATTCATCAACAAAC | basics | no | no | no | yes | yes | yes | yes |
| 1[294]3[307] | TAGGTGTATCACCGGAGGCTGTTGATGA | basics | no | no | no | yes | yes | yes | yes |
| 12[279]9[272] | ATCCGGTGATTGAGTGGAAGTTTCATTCAAGCTAA | basics | no | no | no | yes | yes | yes | yes |
| 11[525]9[538] | CAACAGTCCCTAAACAGGTCATTGCCTG | basics | no | no | no | yes | yes | yes | yes |
| 2[371]0[350] | TTTTAAACAGTTAATGCCCCCTTCAGAACAGCAAGG | basics | no | no | no | yes | yes | yes | yes |
| 3[287]0[294] | GTCATACAAACAAAAATCACCGGAACCACGACAGA | basics | no | no | no | yes | yes | yes | yes |
| 11[588]9[601] | CAAATATACGTGAACATGTCAATCATAT | basics | no | no | no | yes | yes | yes | yes |
| 11[903]9[916] | AATCCTGACGCGCGTGCCAGTTTGAGGG | basics | no | no | no | yes | yes | yes | yes |
| 12[230]11[237] | GGGAGGTGCAACAGGAAAAAC | basics | no | no | no | yes | yes | yes | yes |
| 4[146]5[132] | CAAGAAACAATGAAATACTGAACTTTTTTACCCTGAAC | basics | no | no | no | yes | yes | yes | yes |
| 12[321]9[314] | ATTACCGAAAGGTGGTAGCTCAACATGTCTTTTGC | basics | no | no | no | yes | yes | yes | yes |
| 11[168]9[181] | AACTCAACAATACTGGCATCAATTCTAC | basics | no | no | no | yes | yes | yes | yes |
| 8[167]8[143] | ATTTGGGGCGCGAGAAACGATTTTT | basics | no | no | no | yes | yes | yes | yes |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 1[273]3[286] | TGATATAAGTATAGAAGGATTAGTAAGC | basics | no | no | no | yes | yes | yes | yes |
| 11[1008]9[1021] | CAGGTTTCTGGGGTCCATTCAGGCTGCG | basics | no | no | no | yes | yes | yes | yes |
| 11[1029]9[1042] | ATACAGTCGGAAGCTGGGAAGGGCGATC | basics | no | no | no | yes | yes | yes | yes |
| 5[147]1[160] | ATTGAGCATTACGCAGAAGGAAACCGAG | basics | no | no | no | yes | yes | yes | yes |
| 12[300]9[293] | CAAATCATATTGACATGCAACTAAAGTAAAACATT | basics | no | no | no | yes | yes | yes | yes |
| 11[357]9[370] | CCTTCTGGTACTATACCCTCATATATTT | basics | no | no | no | yes | yes | yes | yes |
| 12[468]9[461] | AAAATACAGCCCTAATATCGCGTTTTAATTCAAC | basics | no | no | no | yes | yes | yes | yes |
| 11[132]12[147] | TTTGAGCCTAATTTGCCTCACTTGCCTGATACCAACGCTAACG | basics | no | no | no | yes | yes | yes | yes |
| 11[693]9[706] | GATTAGAGATAGGGCGCATTAAATTTTT | basics | no | no | no | yes | yes | yes | yes |
| 10[237]7[244] | TTTTATAATTAGCAAAATTAATTCTGCGTACCAGC | basics | no | no | no | yes | yes | yes | yes |
| 9[140]9[167] | TATCCCAATCCAAATAAGCTGAAAAGGT | basics | no | no | no | yes | yes | yes | yes |
| 8[286]3[279] | CGGTGTCGGAGGGATTGCCTTTAATCAATAAATCCTCATTAACCGTTCC | basics | no | no | no | yes | yes | yes | yes |
| 3[114]3[146] | TTTAGACGGGAGAATTAAGCAATAGCTATCTTA | basics | no | no | no | yes | yes | yes | yes |
| 12[209]8[217] | TCAAGATACAATATTACCGCCCGAGTAAATCATACAGGCAAGGTTTGAC | basics | no | no | no | yes | yes | yes | yes |
| 12[510]9[503] | AGAACGCTTCCAGAGGATTGCATCAAAACTATTTT | basics | no | no | no | yes | yes | yes | yes |
| 11[189]8[196] | TGGTAATCACGCAAAGTAGCATTAACATCGCAAAT | basics | no | no | no | yes | yes | yes | yes |
| 11[651]9[664] | GAAGGTTATTAAAGAGCAAATATTTAAA | basics | no | no | no | yes | yes | yes | yes |
| 11[714]9[727] | ATACATTTAAATCACAGCTCATTTTTTA | basics | no | no | no | yes | yes | yes | yes |
| 12[531]9[524] | AACAACATTTTCTGTATTATAGTCAGAAAGGCTAT | basics | no | no | no | yes | yes | yes | yes |
| 12[489]9[482] | AATAGATCGATCTAGAGGAAGCCCGAAAAATTAAT | basics | no | no | no | yes | yes | yes | yes |
| 12[552]9[545] | TCTGTCCAAACAACAAATCAGGTCTTTAAGAGTCT | basics | no | no | no | yes | yes | yes | yes |
| 11[567]9[580] | AAGCATCAAGTTTTGAACGGTAATCGTA | basics | no | no | no | yes | yes | yes | yes |
| 12[342]9[335] | TTTATTTCCGACTTTTAATTGCTGAATATTTCAAC | basics | no | no | no | yes | yes | yes | yes |
| 11[294]9[307] | TGGCAGATAAACAGATGACCCTGTAATA | basics | no | no | no | yes | yes | yes | yes |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 12[363]9 [356] | ATCGAGATTAGAGCTTTTTG CGGATGGCTTTTAGA | basics | no | no | no | yes | yes | yes | yes |
| 4[378]3 [371] | TTTCCGCCACCAGAACCAC CACACAGTGCCCGTATTT | basics | no | no | no | yes | yes | yes | yes |
| 11[777]9 [790] | TTGCCCGTGGTTTGCAGCT TTCATCAAC | basics | no | no | no | yes | yes | yes | yes |
| 12[972]9 [965] | AGTGAATGAGGCAAATTTC AACTTTAATGCTTTCC | basics | no | no | no | yes | yes | yes | yes |
| 1[357]1 [385] | CGCCACCCTCAGAGCCACC ACCCTCATTT | basics | no | no | no | yes | yes | yes | yes |
| 11[798]9 [811] | TAAAAGTGTTGCAGGTGAG CGAGTAACA | basics | no | no | no | yes | yes | yes | yes |
| 8[328]3 [321] | TAATGCTAATTATCCCATCG ACCCTCAGTTGAGGCAGGT CAGGTGTACT | basics | no | no | no | yes | yes | yes | yes |
| 12[993]9 [986] | AAGACGCACACTCAAATTG GGCTTGAGATGCCGGA | basics | no | no | no | yes | yes | yes | yes |
| 11[756]9 [769] | CGACAACAATCCTGCGCGT CTGGCCTTC | basics | no | no | no | yes | yes | yes | yes |
| 12[951]9 [944] | GGTCTGAAGGCACCAATTA CCTTATGCGAGGAAGA | basics | no | no | no | yes | yes | yes | yes |
| 12[405]9 [398] | CTTATCACATGTACGATTAG AGAGTACCGTGTAGG | basics | no | no | no | yes | yes | yes | yes |
| 12[867]9 [860] | ACAAAGAAACGGCTACGGA ACAACATTAAATGGGA | basics | no | no | no | yes | yes | yes | yes |
| 4[170]3 [153] | TTGAGTTAAGCCCAATAATA AGAGCCGAAGC | basics | no | no | no | yes | yes | yes | yes |
| 12[426]9 [419] | ATCAATATCGTCACAAGCAA ACTCCAACGGTGAGA | basics | no | no | no | yes | yes | yes | yes |
| 8[265]0 [273] | CATATAAGGCGACAAGCGC GTTTAGCGTTTGCCATCTTT TCATAGCGTC | basics | no | no | no | yes | yes | yes | yes |
| 10[167]1 0[128] | TCTTTGATTAGTAATAACAA GTTACAAAATAAACAGCTTT | basics | no | no | no | yes | yes | yes | yes |
| 2[151]2 [114] | AAGTAAGCAGATAGCCGAA AACAGGGAAGCGCATTTTT | basics | no | no | no | yes | yes | yes | yes |
| 3[308]0 [315] | TACAGGAACGATTGCACCG GAACCGCCTTAGCAGC | basics | no | no | no | yes | yes | yes | yes |
| 10[293]1 2[280] | GAGGCCGATTAAAGTGGAT TAAAGGCTT | basics | no | no | no | yes | yes | yes | yes |
| 8[916]11 [923] | TACCAGTCCATTAAACGGG TAGGCTTAGGGATTAT | basics | no | no | no | yes | yes | yes | yes |
| 10[965]1 2[952] | CTGCCCGCTTTCCATACCA TAAATCATA | basics | no | no | no | yes | yes | yes | yes |
| 8[685]11 [692] | GTTTTGCCAGCTTGCTTTC GATTACCAGACTAATA | basics | no | no | no | yes | yes | yes | yes |
| 10[1028] 12[1015] | ATAAAGTGTAAAGCAACGT CACCTTGAA | basics | no | no | no | yes | yes | yes | yes |
| 2[321]11 [314] | CATGAAAGTATTAATACTCA GACCGTAAATTCATTCGCC CAAGTCACAC | basics | no | no | no | yes | yes | yes | yes |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 8[391]11[398] | TTTAATTGCCCAATAGGAACCTTCCAAGGACAATA | basics | no | no | no | yes | yes | yes | yes |
| 10[608]12[595] | GGCGATGGCCCACTCAAACCCTCGAGCC | basics | no | no | no | yes | yes | yes | yes |
| 8[622]11[629] | TCATAAATTTTCACGTTGAAACCAACATGGCAAAT | basics | no | no | no | yes | yes | yes | yes |
| 10[671]12[658] | AACAAGAGTCCACTATCTAAATAGGGCT | basics | no | no | no | yes | yes | yes | yes |
| 8[979]11[986] | TGGTTTAAAGAATACACTAAATGAGAAGACAGAAA | basics | no | no | no | yes | yes | yes | yes |
| 8[475]11[482] | GACTTCACATAGTTAGCGTAAAAGTCCTCCAGCAG | basics | no | no | no | yes | yes | yes | yes |
| 2[300]11[293] | AGACTCCTCAAGAGCCCGGAAATCAAGTAGGTAAAGATATAGTTTACAT | basics | no | no | no | yes | yes | yes | yes |
| 10[503]12[490] | TGACGGGGAAAGCCAACAGAGTATCAAC | basics | no | no | no | yes | yes | yes | yes |
| 7[350]11[356] | TTGGGAAACAAGCAATAGAAC | basics | no | no | no | yes | yes | yes | yes |
| 10[335]12[322] | TAACGTGCTTTCCTAATAAAAAGGAATC | basics | no | no | no | yes | yes | yes | yes |
| 10[1091]12[1078] | TAGCTGTTTCCTGTTGATTGCTATATGT | basics | no | no | no | yes | yes | yes | yes |
| 10[692]12[679] | TTGAGTGTTGTTCCACTAACATATAAAG | basics | no | no | no | yes | yes | yes | yes |
| 10[755]12[742] | TTTGATGGTGGTTCCTTTACACGGAATC | basics | no | no | no | yes | yes | yes | yes |
| 10[419]12[406] | GTCACGCTGCGCGTATGGCTAGTCTTTC | basics | no | no | no | yes | yes | yes | yes |
| 10[398]12[385] | ACACCCGCCGCGCTTGGCACAAACGGGT | basics | no | no | no | yes | yes | yes | yes |
| 10[797]12[784] | CAAGCGGTCCACGCAACGTTAACCGACC | basics | no | no | no | yes | yes | yes | yes |
| 10[482]12[469] | GTGGCGAGAAAGGACGAACCAGAACAAG | basics | no | no | no | yes | yes | yes | yes |
| 7[245]11[251] | GCCAAAGTTAGCGAGAAATAC | basics | no | no | no | yes | yes | yes | yes |
| 10[734]12[721] | GGCAAAATCCCTTATGAGGATAAGCCTG | basics | no | no | no | yes | yes | yes | yes |
| 8[496]11[503] | AGATTAAAAGTTTTGTCGTCTGCCTGTTGTGAGGC | basics | no | no | no | yes | yes | yes | yes |
| 8[1042]11[1049] | ATTCAGTAACGGAGATTTGTATCGCTATCCTTTTA | basics | no | no | no | yes | yes | yes | yes |
| 10[566]12[553] | TTGGGGTCGAGGTGAAATGAAAAGTAAT | basics | no | no | no | yes | yes | yes | yes |
| 8[412]11[419] | AGGTCAGCGTAACACTGAGTTATCGGCTTTAGTCT | basics | no | no | no | yes | yes | yes | yes |
| 8[664]11[671] | GTAAAATCCTTTAATTGTATCTCAACAGATATCTT | basics | no | no | no | yes | yes | yes | yes |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 10[839]1 2[826] | CAGCTGATTGCCCTCGGAA CATAGTTAA | basics | no | no | no | yes | yes | yes | yes |
| 8[181]11 [188] | TTAGCTAGAAACGCAAAGA CACACCCAGGCCTTGC | basics | no | no | no | yes | yes | yes | yes |
| 10[188]1 2[175] | ATTAACCGTTGTAGACTATC GCTACAAT | basics | no | no | no | yes | yes | yes | yes |
| 10[440]1 2[427] | AGGGCGCTGGCAAGGCGA ACTGAAACCA | basics | no | no | no | yes | yes | yes | yes |
| 10[860]1 2[847] | TTTCACCAGTGAGAAGGAG CGAAAACTT | basics | no | no | no | yes | yes | yes | yes |
| 2[279]11 [272] | AGGATTAGCGGGGTAGAG GGTAGACTGTTTCAACCATT CTAATCAATCG | basics | no | no | no | yes | yes | yes | yes |
| 8[706]11 [713] | CGAGAGGTTCTTAAACAGC TTTCATATGATAGATA | basics | no | no | no | yes | yes | yes | yes |
| 8[454]11 [461] | ATTCGAGTAGCATTCCACA GAATATCCCTTAAAAA | basics | no | no | no | yes | yes | yes | yes |
| 10[314]1 2[301] | ATCAGAGCGGGAGCTTCAC CATAGCAAG | basics | no | no | no | yes | yes | yes | yes |
| 8[1000]1 1[1007] | AGTAGTATCTTTGACCCCC AGCGATAGCAGATTTT | basics | no | no | no | yes | yes | yes | yes |
| 8[790]11 [797] | TAACGCCGCTTGCAGGGAG TTTTGAAATTTAATTT | basics | no | no | no | yes | yes | yes | yes |
| 10[629]1 2[616] | GGGCGAAAAACCGTGTCAG TTGTAATTT | basics | no | no | no | yes | yes | yes | yes |
| 10[251]1 2[238] | ATCCTGAGAAGTGTGCTCA TGACCTCCC | basics | no | no | no | yes | yes | yes | yes |
| 10[923]1 2[910] | TAATGAATCGGCCAATTGTT TGTTGGGT | basics | no | no | no | yes | yes | yes | yes |
| 8[811]11 [818] | CATTCAAGCTTTTGCGGGA TCTTCTGACACATTAT | basics | no | no | no | yes | yes | yes | yes |
| 8[559]11 [566] | AAATCAATTTCAACAGTTTC AAAAGGTAAAATCTA | basics | no | no | no | yes | yes | yes | yes |
| 8[580]11 [587] | TCAGAAAGAGAATAGAAAG GAAGAGAATTGAACCT | basics | no | no | no | yes | yes | yes | yes |
| 2[342]11 [335] | TCGGAACCTATTATCCACC CTAATGAAAACCGTCATCAT CGTGGGACAT | basics | no | no | no | yes | yes | yes | yes |
| 10[461]1 2[448] | AAAGCGAAAGGAGCATCGC CAATCCTAA | basics | no | no | no | yes | yes | yes | yes |
| 10[1070] 12[1057] | TGTTATCCGCTCACAGAAA CAGCTTCTG | basics | no | no | no | yes | yes | yes | yes |
| 10[524]1 2[511] | GGGAGCCCCCGATTATTAA CACTAATGC | basics | no | no | no | yes | yes | yes | yes |
| 10[818]1 2[805] | CTGGCCCTGAGAGATTGAG TACTAAATT | basics | no | no | no | yes | yes | yes | yes |
| 10[986]1 2[973] | ACATTAATTGCGTTACGTAA AAGTCAAT | basics | no | no | no | yes | yes | yes | yes |
| 1[161]11 [167] | GAAACGCGATTAAGGGCAA CATGAATCTGTAGAAG | basics | no | no | no | yes | yes | yes | yes |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 8[1063]1 1[1077] | ATCAACGCTGATAAATTGTG TTAACCTTATAACGGATTCG CC | basics | no | no | no | yes | yes | yes | yes |
| 8[601]11 [608] | CCCTCAAAAGGAATTGCGA ATGGCATTTTCAATCA | basics | no | no | no | yes | yes | yes | yes |
| 8[517]11 [524] | GCAAAGCCGTTAGTAAATG AATGTTCAGCCGCCTG | basics | no | no | no | yes | yes | yes | yes |
| 8[538]11 [545] | CCCTGACTATGGGATTTTG CTAGACGACTGAGAGC | basics | no | no | no | yes | yes | yes | yes |
| 10[356]1 2[343] | GGTTGCTTTGACGAAACAG AGAGCCGTT | basics | no | no | no | yes | yes | yes | yes |
| 8[370]11 [377] | GAGGTCACAGCAAAATCAC GGCAAGTACAGCGTAA | basics | no | no | no | yes | yes | yes | yes |
| 10[902]1 2[889] | GGGAGAGGCGGTTTCAATT CATAAATGC | basics | no | no | no | yes | yes | yes | yes |
| 8[895]11 [902] | GAAAAATGACTTTTTCATGA GCTATATGTCAATAT | basics | no | no | no | yes | yes | yes | yes |
| 8[832]11 [839] | AGTTGAGTCAGCAGCGAAA GATATATTTAAGAAAC | basics | no | no | no | yes | yes | yes | yes |
| 8[769]11 [776] | GGCATAGCCGATATATTCG GTAAATAAGAAATCCT | basics | no | no | no | yes | yes | yes | yes |
| 10[209]1 2[196] | AAGAGTCTGTCCATATCCA GATAGTTGC | basics | no | no | no | yes | yes | yes | yes |
| 10[881]1 2[868] | GGGCGCCAGGGTGGTTCC TGATCGCAAG | basics | no | no | no | yes | yes | yes | yes |
| 8[748]11 [755] | TCATAACACAACCATCGCC CATAAACACAACAATT | basics | no | no | no | yes | yes | yes | yes |
| 8[727]11 [734] | CGACGATATAGTTGCGCCG ACCTAGAAATTAGAAG | basics | no | no | no | yes | yes | yes | yes |
| 8[643]11 [650] | GCGTCCAAAAAAAGGCTC CAGAATCGCAATTGAG | basics | no | no | no | yes | yes | yes | yes |
| 8[1021]11 1[1028] | CTGACGAACCAAGCGCGAA ACTTAGAATGATGAAT | basics | no | no | no | yes | yes | yes | yes |
| 10[1049] 12[1036] | CACAACATACGAGCAACAG TATAATTAA | basics | no | no | no | yes | yes | yes | yes |
| 8[433]11 [440] | AGACCGGCAGTACAAACTA CAGCATGTAGATAGCC | basics | no | no | no | yes | yes | yes | yes |
| 10[650]1 2[637] | AACGTGGACTCCAATGAAA GGCATATTT | basics | no | no | no | yes | yes | yes | yes |
| 10[587]1 2[574] | CCATCACCCAAATCACCTT GCATAAAGT | basics | no | no | no | yes | yes | yes | yes |
| 10[1007] 12[994] | GCCTAATGAGTGAGATTGC GTTTAGATT | basics | no | no | no | yes | yes | yes | yes |
| 8[958]11 [965] | CATTGTGAACCTAAAACGA AATTATCAATCAAAAT | basics | no | no | no | yes | yes | yes | yes |
| 10[944]1 2[931] | AACCTGTCGTGCCAATAA TGCCTTTTT | basics | no | no | no | yes | yes | yes | yes |
| 8[937]11 [944] | ATTTTAATAATGCCACTACG AGAGACTAGAAGGGT | basics | no | no | no | yes | yes | yes | yes |
| 8[874]11 [881] | CGAACTAACAGAGGCTTTG AGAATCCAATTATCAG | basics | no | no | no | yes | yes | yes | yes |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 10[377]1 2[364] | CCGCTACAGGGCGCACCT GAACGCACTC | basics | no | no | no | yes | yes | yes | yes |
| 10[776]1 2[763] | CCCCAGCAGGCGAATCGTA TTGCGTTAA | basics | no | no | no | yes | yes | yes | yes |
| 10[713]1 2[700] | AAAGAATAGCCCGAGCCGT CACGTTATA | basics | no | no | no | yes | yes | yes | yes |
| 10[272]1 2[259] | AGACAGGAACGGTATTGAC GCGAACGCG | basics | no | no | no | yes | yes | yes | yes |
| 10[545]1 2[532] | GCACTAAATCGGAAGCCAC GCGACAATA | basics | no | no | no | yes | yes | yes | yes |
| 8[853]11 [860] | TTACAGGGGAACGAGGGTA GCACGCGAGGAATTAT | basics | no | no | no | yes | yes | yes | yes |
| 10[230]1 2[217] | ATCAGTGAGGCCACAGCCA TTTTTGAAG | basics | no | no | no | yes | yes | yes | yes |
| 7[1099]1 1[1171] | TAGCCGGAACGAGGTTTTT AATCGCGCATTtaagtgagaccc gtacatat | A655 Marker Extensions | no | no | no | yes | yes | yes | yes |
| 7[1078]1 1[1174] | CGCGACCTGCTCCAAAATC AATTTGAATTTtaagtgagacccg tacatat | A655 Marker Extensions | no | no | no | yes | yes | yes | yes |
| 10[1133] 12[1169] | GAGGATCCCCGGGTATTAT TCCATTTGATTtaagtgagaccc gtacatat | A655 Marker Extensions | no | no | no | yes | yes | yes | yes |
| 12[1098] 9[1175] | AGTACATTGTTACTGTAATC TTGACAAGATGTGCTTTtaag tgagacccgtacatat | A655 Marker Extensions | no | no | no | yes | yes | yes | yes |
| 11[1113] 8[1160] | GAGGCGAACCGAGCACGC CAGGGTTTTCCGCATAGTTt aagtgagacccgtacatat | A655 Marker Extensions | no | no | no | yes | yes | yes | yes |
| 8[1159]7 [1158] | TTTAGAGGACAGATGAACG ACTGACCAACTTTGAATTtaa gtgagacccgtacatat | A655 Marker Extensions | no | no | no | yes | yes | yes | yes |
| 12[1166] 11[1165] | TTTACATCAAGAAAACAAAG AAGATGATGAAACAATTtaag tgagacccgtacatat | A655 Marker Extensions | no | no | no | yes | yes | yes | yes |
| 10[1112] 12[1172] | TCGAATTCGTAATCTACAAA ATGGAAACTTtaagtgagacccgt acatat | A655 Marker Extensions | no | no | no | yes | yes | yes | yes |
| 10[1162] 12[1167] | TTTCAAGCTTTGCCTGCAG GTCAGCAAAAATTAATTTTta agtgagacccgtacatat | A655 Marker Extensions | no | no | no | yes | yes | yes | yes |
| 7[1120]1 1[1168] | GGTCAATCATAAGGACAAT TTATTTCAATTtaagtgagacccg tacatat | A655 Marker Extensions | no | no | no | yes | yes | yes | yes |
| 10[1077] 8[1166] | GTGAAATCTGGCGAAAGGG GGAACCGGATTtaagtgagacc cgtacatat | A655 Marker Extensions | no | no | no | yes | yes | yes | yes |
| 12[1140] 9[1169] | ACATTTAGAACCGAGTGTA CAGACCAGGCCAGTCATTta agtgagacccgtacatat | A655 Marker Extensions | no | no | no | yes | yes | yes | yes |
| 12[1119] 9[1172] | ATTACCTCGCAGACGCTGG CTGACCTTCTTGGGTATTtaa gtgagacccgtacatat | A655 Marker Extensions | no | no | no | yes | yes | yes | yes |

-continued

| Oligo Position | Sequence | Staple Type | FIG. 1 | 7 | 8 | 9A,B | 9C,D | 10A,B | 10C,D |
|---|---|---|---|---|---|---|---|---|---|
| 11[1092] 8[1163] | ACCAAGTATGGTCAGCAAG GCGATTAAGATCAAGATTta agtgagacccgtacatat | A655 Marker Extensions | no | no | no | yes | yes | yes | yes |
| 11[1134] 9[1161] | TTACCTGGACTCTACGACG TTGTAAAACGACGGCCAGT GCTTtaagtgagacccgtacatat | A655 Marker Extensions | no | no | no | yes | yes | yes | yes |

Additional Staple Strands

| Structure | Pos. in Structure | Oligo Name | Sequence | FIG. 1 | 7 | 8 | 9A,B | 9C,D | 10A,B | 10C,D |
|---|---|---|---|---|---|---|---|---|---|---|
| Base Plate | 10[39] 12[40] | Dock Left 3' A565 | GCTATTACGGCGATT AAGTTGGGTGGCCAA CG TT TT ATACAACTAT T [ATTO565] | no | yes | no | no | no | yes | no |
| Base Plate | 10[167] 12[168] | Dock Right 3' A647N | GGCCTCAGGTTTCCT GTGTGAAAGAGCCGG TT TT ATACAACTAT T [ATTO647N] | no | yes | no | no | no | yes | no |
| 6hb Arm Lin | 4[102] 3[90] | A488 Donor | [Alexa488] TT TTTCTGAATTGTCAAC CTTTTAAGTG | no | yes | no | no | no | no | no |
| 6hb Arm Lin | 2[105] 3[121] | Dock arm 8nt | TTTAACAGCAGTTGC TCCTTAGTG TT ATAGTTGT | no | yes | no | no | no | no | no |
| 6hb Arm Lin | 2[105] 3[121] | Dock arm 9nt | TTTAACAGCAGTTGC TCCTTAGTG TT ATAGTTGTA | no | yes | no | no | no | no | no |
| 6hb Arm Lin | 2[105] 3[121] | Dock arm 10nt | TTTAACAGCAGTTGC TCCTTAGTG TT ATAGTTGTAT | yes | yes | no | no | no | no | no |
| Base Plate | 10[39] 12[40] | Dock Left 3' | GCTATTACGGCGATT AAGTTGGGTGGCCAA CG TT TT ATACAACTAT | no | no | no | yes | no | no | no |
| Base Plate | 10[167] 12[168] | Dock Right 3' | GGCCTCAGGTTTCCT GTGTGAAAGAGCCGG TT TT ATACAACTAT | no | no | no | yes | no | no | no |
| Base Plate | 2[71] 4[72] | Dock Up 3' | AAATGTTTAAATCAAA AATCAGGGCTGTAG TT TT ATACAACTAT | no | no | no | no | no | no | no |
| Base Plate | 16[71] 18[72] | Dock Down 3' | TCCTGAGATCACTTG CCTGAGTAGTGGCAC TT TT ATACAACTAT | no | no | no | no | no | no | no |
| Base Plate | 12[39] 14[40] | Unzip Dock Left 20nt 5' | GGAAGTTGAGATGGT AGAGG TT GCAAGGTGGCTT CGCGGGGAGTTTTTC TTTTCACCATTTTTTGG | no | no | no | no | yes | no | no |
| Base Plate | 10[39] 12[40] | Unzip Dock Left helper | GCTATTACGGCGATT AAGTTGGGTGGCCAA CG TT GCCACCTTGC | no | no | no | no | yes | no | no |

-continued

| Structure | Pos. in Structure | Oligo Name | Sequence | FIG. 1 | 7 | 8 | 9A,B | 9C,D | 10A,B | 10C,D |
|---|---|---|---|---|---|---|---|---|---|---|
| Base Plate | 12[167] 14[168] | Unzip Dock Right 20n t 5' | GGAAGTTGAGATGGT AGAGG TT GCAAGGTGGCTT AAGCATAACCGAAAT CGGCAAAAGGGTTGA | no | no | no | no | yes | no | no |
| Base Plate | 10[167] 12[168] | Unzip Dock Right helper | GGCCTCAGGTTTCCT GTGTGAAAGAGCCGG TT GCCACCTTGC | no | no | no | no | yes | no | no |
| 6hb Arm HT | 4[231] | A488 Donor HT | [Alexa488] TT CTGAATTGTCAACCTT ATGACAATGT | no | no | no | no | no | yes | no |
| 6hb Arm HT | 2[253] | Dock arm 9nt HT | CAGGAGTTCCCACTG AGACTTAAGTGTCCT TAGTG TT ATAGTTGTA | no | no | no | yes | no | yes | no |
| 6hb Arm HT | 2[253] | Unzip Dock Arm 20nt HT | TTAAAGGCCGCTAAC AGCAGTTGCTCCTTA GTG TTGCTAGCACGC TT CCTCTACCATCTCAA CTTCC | no | no | no | no | yes | no | no |
| 6hb Arm HT | 4[231] | Unzip Dock Arm 20nt helper | GCGTGCTAGCTT CATGGCTTTTGATGA TACAGGAGTGT | no | no | no | no | yes | no | no |
| CQO_Parking1 6A | 10[39] | Park12 ntLeft | AGATGGTAGAGG TT GCTATTACGGCG ATTAAGTTGGGTGGC CAACG | no | no | no | no | no | no | no |
| CQO_Parking1 2nt | 10[167] | Park12 ntRight | AGATGGTAGAGG TT GGCCTCAGGTTT CCTGTGTGAAAGAGC CGG | no | no | no | no | no | no | no |
| CQO_Parking1 6A | 10[39] | Park16 A10[39] | AAAAAAAAAAAAAAA CC GCTATTACGGCG ATTAAGTTGGGTGGC CAACG | no | no | no | no | no | no | no |
| CQO_Parking1 6A | 10[167] | Park16 A10[167] | AAAAAAAAAAAAAAA CC GGCCTCAGGTTT CCTGTGTGAAAGAGC CGG | no | no | no | no | no | no | no |
| CQO_Parking1 6A | 12[39] | Park16 A12[39] | AAAAAAAAAAAAAAA CC CGCGGGGAGTTT TTCTTTTCACCATTTT TTGG | no | no | no | no | no | no | no |
| CQO_Parking1 6A | 12[167] | Park16 A12[167] | AAAAAAAAAAAAAAA CC AAGCATAACCGA AATCGGCAAAGGGT TGA | no | no | no | no | no | no | no |
| CQO_Parking1 6A | 20[103] | Park16 A20[103] | AAAAAAAAAAAAAAA CC TCAATAGATTCCT GATTATCAGATGATG GCAA | no | no | no | no | no | no | no |
| CQO_Parking1 6A | 18[71] | Park16 A18[71] | AAAAAAAAAAAAAAA CC AGACAATAAGAG GTGAGGCGGTCTTAG AAG | no | no | no | no | no | no | no |

-continued

| Structure | Pos. in Structure | Oligo Name | Sequence | FIG. 1 | 7 | 8 | 9A,B | 9C,D | 10A,B | 10C,D |
|---|---|---|---|---|---|---|---|---|---|---|
| CQO_Parking1 6A | 16[167] | Park16 A16[167] | AAAAAAAAAAAAAAA CC GAGCACGTTGGA AATACCTACATACATT GG | no | no | no | no | no | no | no |
| CQO_Parking1 6A | 2[71] | Park16 A2[71] | AAAAAAAAAAAAAAA CC AAATGTTTAAATC AAAAATCAGGGCTGT AG | no | no | no | no | no | no | no |
| CQO_Parking1 6A | 6[39] | Park16 A6[39] | AAAAAAAAAAAAAAA CC TTAAATGCAAAAG GGTGAGAAGGTGTT AAAT | no | no | no | no | no | no | no |
| CQO_Parking1 6A | 14[39] | Park16 A14[39] | AAAAAAAAAAAAAAA CC GGTCGAGGGGG AGCCCCCGATTTAGT GAGGCC | no | no | no | no | no | no | no |
| CQO_Parking1 6A | 16[39] | Park16 A16[39] | AAAAAAAAAAAAAAA CC ACCGAGTATTGT AGCAATACTTCTAGT CTTTA | no | no | no | no | no | no | no |
| CQO_Parking1 6A | 14[167] | Park16 A14[167] | AAAAAAAAAAAAAAA CC GTGTTGTTACAC CCGCCGCGCTTCTTT GAC | no | no | no | no | no | no | no |
| CQO_Parking1 6A | 19[56] | Park16 A19[56] | AAAAAAAAAAAAAAA CC GATAAAACTTTTT GAATGGCTATTTTGAT TAGTAATAACA | no | no | no | no | no | no | no |
| CQO_Parking1 6A | 18[103] | Park16 A18[103] | AAAAAAAAAAAAAAA CC TCTGACCTGCAA CAGTGCCACGCTTAG AGCCG | no | no | no | no | no | no | no |
| CQO_Parking1 6A | 19[120] | Park16 A19[120] | AAAAAAAAAAAAAAA CC GCAGCAACTGGC CAACAGAGATATCCA GAACAATATT | no | no | no | no | no | no | no |
| CQO_Parking1 6A | 19[152] | Park16 A19[152] | AAAAAAAAAAAAAAA CC GCTGAACCCCAG TCACACGACCAGACA GGAAAAACGCTCA | no | no | no | no | no | no | no |
| CQO_Parking1 6A | 18[135] | Park16 A18[135] | AAAAAAAAAAAAAAA CC GGGACATTATGA AAAATCTAAAGCATAT CTTT | no | no | no | no | no | no | no |
| CQO_Parking1 6A | 8[39] | Park16 A8[39] | AAAAAAAAAAAAAAA CC CAGCTCATAATTC GCGTCTGGCCTGCCT CTTC | no | no | no | no | no | no | no |
| CQO_Parking1 6A | 6[159] | Park16 A6[159] | AAAAAAAAAAAAAAA CC AGCCTCAGAGCA TAAAAATTCTACTAAT AGTA | no | no | no | no | no | no | no |
| CQO_Parking1 6A | 19[88] | Park16 A19[88] | AAAAAAAAAAAAAAA CC CACCGCCTGAAA GCGTAAGAATACGAA GAACTCAAACTAT | no | no | no | no | no | no | no |
| CQO_Parking1 6A | 4[39] | Park16 A4[39] | AAAAAAAAAAAAAAA CC GGTGTCTGCAAT TCTGCGAACGAGCAT ATATT | no | no | no | no | no | no | no |

-continued

| Structure | Pos. in Structure | Oligo Name | Sequence | FIG. 1 | 7 | 8 | 9A,B | 9C,D | 10A,B | 10C,D |
|---|---|---|---|---|---|---|---|---|---|---|
| CQO_Parking1 6A | 4[103] | Park16 A4[103] | AAAAAAAAAAAAAAA CC TAGAGCTTTGTTT AGCTATATTTTCCTGT AAT | no | no | no | no | no | no | no |
| CQO_Parking1 6A | 4[167] | Park16 A4[167] | AAAAAAAAAAAAAAA CC GGTCAGGAGTAG CATTAACATCCAAAAT TA | no | no | no | no | no | no | no |
| CQO_Parking1 6A | 4[135] | Park16 A4[135] | AAAAAAAAAAAAAAA CC TTTTGATACTGAA AAGGTGGCATCGCTA AATC | no | no | no | no | no | no | no |
| CQO_Parking1 6A | 4[71] | Park16 A4[71] | AAAAAAAAAAAAAAA CC CTCAACATATTAG ATACATTTCGTCAAC GC | no | no | no | no | no | no | no |
| CQO_Parking1 6A | 2[103] | Park16 A2[103] | AAAAAAAAAAAAAAA CC AAAAGAAGTATA GTCAGAAGCAAAGGA TGGCT | no | no | no | no | no | no | no |
| CQO_Parking1 6A | 18[39] | Park16 A18[39] | AAAAAAAAAAAAAAA CC ATGCGCGAATAC CGAACGAACCACCAA CTCGT | no | no | no | no | no | no | no |
| CQO_Parking1 6A | 2[135] | Park16 A2[135] | AAAAAAAAAAAAAAA CC GATAAAAAAGAT TAAGAGGAAGCATTG CTCC | no | no | no | no | no | no | no |
| CQO_Parking1 6A | 8[167] | Park16 A8[167] | AAAAAAAAAAAAAAA CC CATGTCAAGATG GGCGCATCGTACAGT ATC | no | no | no | no | no | no | no |
| 6hb Arm HT | 6[224] 4[231] | HTD2_0T_5Pr | GCGTGCTAGCTT TTCTGAATTGTCAACC TTATGACAATGT | no | no | no | no | no | no | no |
| 6hb Arm HT | 2[253] 6[255] | HTD2_16T_3Pr | CAGGAGTTCCCACTG AGACTTAAGTGTCCT TAGTGTT TTGCTAGCACGC CC TTTTTTTTTTTTTTTT | no | no | no | no | no | no | no |
| Base Plate | 9[120] 7[119] | Plate A655 1 | CGGCGGACCCAAAAA CAGGAAGGAGAGGG TTT TAAGTGAGACCCGTA CATAT | no | no | no | no | no | no | yes |
| Base Plate | 10[135] 12[136] | Plate A655 2 | CCGGCACCCCGAGC TCGAATTCGTTGCCT AATTT TAAGTGAGACCCGTA CATAT | no | no | no | no | no | no | yes |
| Base Plate | 8[135] 10[136] | Plate A655 3 | AGAAAAGCTTGACCG TAATGGGATCCAGCT TTTT TAAGTGAGACCCGTA CATAT | no | no | no | no | no | no | yes |
| Base Plate | 14[159] 13[159] | Plate A655 4 | CCAGTTTGGAACAAG ACTGTTTGATGGTGG TTTT TAAGTGAGACCCGTA CATAT | no | no | no | no | no | no | yes |

-continued

| Structure | Pos. in Structure | Oligo Name | Sequence | FIG. 1 | 7 | 8 | 9A,B | 9C,D | 10A,B | 10C,D |
|---|---|---|---|---|---|---|---|---|---|---|
| Base Plate | 10[159] 9[159] | Plate A655 5 | GAAGATCGCACTCCA GAGGTCACGTTGGTG TATT TAAGTGAGACCCGTA CATAT | no | no | no | no | no | no | yes |
| Base Plate | 14[127] 13[119] | Plate A655 6 | CGTGGACTCCAACGT CCACGCTGTT TAAGTGAGACCCGTA CATAT | no | no | no | no | no | no | yes |
| Base Plate | 6[135] 8[136] | Plate A655 7 | GGTTGTACTTTGAGA GATCTACAATGATAAT CTT TAAGTGAGACCCGTA CATAT | no | no | no | no | no | no | yes |
| Base Plate | 12[135] 14[136] | Plate A655 8 | GAGTGAGCCCAGCA GGCGAAAATCGTCCA CTATT TAAGTGAGACCCGTA CATAT | no | no | no | no | no | no | yes |
| Base Plate | 16[135] 18[136] | Plate A655 9 | CAGAGCGGACCGCC AGCCATTGCATAATA AAATT TAAGTGAGACCCGTA CATAT | no | no | no | no | no | no | yes |
| Base Plate | 4[135] 6[136] | Plate A655 10 | TTTTGATACTGAAAAG GTGGCATCGCTAAAT CTT TAAGTGAGACCCGTA CATAT | no | no | no | no | no | no | yes |
| Base Plate | 14[135] 16[136] | Plate A655 11 | TTAAAGAACAAGTGT AGCGGTCACGTTAGA ATTT TAAGTGAGACCCGTA CATAT | no | no | no | no | no | no | yes |
| Base Plate | 12[71] 14[72] | Plate A565 1 | TCGTGCCACTGATTG CCCTTCACGCCCACT TT CAACCTACTTAACCT CCG | no | no | no | no | no | no | yes |
| Base Plate | 4[71] 6[72] | Plate A565 2 | CTCAACATATTAGATA CATTTCGTCAACGCTT CAACCTACTTAACCT CCG | no | no | no | no | no | no | yes |
| Base Plate | 10[63] 9[63] | Plate A565 3 | AGGGCGATCGGTGC GGTCCTGTAGCCAGC TTTTT CAACCTACTTAACCT CCG | no | no | no | no | no | no | yes |
| Base Plate | 14[95] 13[87] | Plate A565 4 | GTCTATCAGGGCGAT GCGCCTGGCTT CAACCTACTTAACCT CCG | no | no | no | no | no | no | yes |
| Base Plate | 9[88] 7[87] | Plate A565 5 | TAACAACCTTTAAATT GTAAACGTATTCAAC CTT CAACCTACTTAACCT CCG | no | no | no | no | no | no | yes |
| Base Plate | 14[63] 13[63] | Plate A565 6 | CATCACCCAAATCAA GGTGAGACGGGCAA CAGTT CAACCTACTTAACCT CCG | no | no | no | no | no | no | yes |

-continued

| Structure | Pos. in Structure | Oligo Name | Sequence | FIG. 1 | 7 | 8 | 9A,B | 9C,D | 10A,B | 10C,D |
|---|---|---|---|---|---|---|---|---|---|---|
| Base Plate | 6[71] 8[72] | Plate A565 7 | AAGGATAACACCATC AATATGATTAATATTTT CAACCTACTTAACCT CCG | no | no | no | no | no | no | yes |
| Base Plate | 10[71] 12[72] | Plate A565 8 | TGTTGGGACAGTCAC GACGTTGTAAACCTG TT CAACCTACTTAACCT CCG | no | no | no | no | no | no | yes |
| Base Plate | 16[71] 18[72] | Plate A565 9 | TCCTGAGATCACTTG CCTGAGTAGTGGCAC TT CAACCTACTTAACCT CCG | no | no | no | no | no | no | yes |
| Base Plate | 8[71] 10[72] | Plate A565 10 | TTGTTAAACATCAACA TTAAATGGCGCAACTT CAACCTACTTAACCT CCG | no | no | no | no | no | no | yes |
| Base Plate | 14[71] 16[72] | Plate A565 11 | ACGTGAACGCCGGC GAACGTGGCGCCAG AATT CAACCTACTTAACCT CCG | no | no | no | no | no | no | yes |
| 6hb Arm HT | 11[252] | AuNRE xt 1 | AAAAAAACTACATTC GCCAGAAGCCTCAGA GCATA | no | no | no | no | no | no | yes |
| 6hb Arm HT | 12[258] | AuNRE xt 2 | AAAAAAAAGGCGTT ACAAAAGCAGTTGAT TCCCAAGCAATAA | no | no | no | no | no | no | yes |
| 6hb Arm HT | 11[273] | AuNRE xt 3 | AAAAAAAATCTGAAA GGATTTTATCGGTTG TACCAA | no | no | no | no | no | no | yes |
| 6hb Arm HT | 11[168] | AuNRE xt 4 | AAAAAAAAACTCAAC AATACTGGCATCAATT CTAC | no | no | no | no | no | no | yes |
| 6hb Arm HT | 12[174] | AuNRE xt 5 | AAAAAAAATTTATCCT ATAAAATATTTTC | no | no | no | no | no | no | yes |
| 6hb Arm HT | 12[195] | AuNRE xt 6 | AAAAAAAATATTTTGC CACGGAGGTCAATAA CCTGTTAATAGT | no | no | no | no | no | no | yes |
| 6hb Arm HT | 11[189] | AuNRE xt 7 | AAAAAAAATGGTAATC ACGCAAAGTAGCATT AACATCGCAAAT | no | no | no | no | no | no | yes |
| 6hb Arm HT | 12[216] | AuNRE xt 8 | AAAAAAAACCTTAAAT CACAATCATTAGATAC ATTTCCAATAA | no | no | no | no | no | no | yes |
| 6hb Arm HT | 2[279] | AuNRE xt 9 | AGGATTAGCGGGGTA GAGGGTAGACTGTTT CAACCATTCTAATCAA TCGAAAAAAAA | no | no | no | no | no | no | yes |
| 6hb Arm HT | 1[161] | AuNRE xt 10 | GAAACGCGATTAAGG GCAACATGAATCTGT AGAAGAAAAAAAA | no | no | no | no | no | no | yes |
| 6hb Arm HT | 8[181] | AuNRE xt 11 | TTAGCTAGAAACGCA AAGACACACCCAGGC CTTGCAAAAAAAA | no | no | no | no | no | no | yes |

-continued

| Structure | Pos. in Structure | Oligo Name | Sequence | FIG. 1 | 7 | 8 | 9A,B | 9C,D | 10A,B | 10C,D |
|---|---|---|---|---|---|---|---|---|---|---|
| 6hb Arm HT | 10[230] | AuNRExt 12 | ATCAGTGAGGCCACAGCCATTTTTGAAGAAAAAAAA | no | no | no | no | no | no | yes |
| 6hb Arm HT | 7[245] | AuNRExt 13 | GCCAAAGTTAGCGAGAAATACAAAAAAAA | no | no | no | no | no | no | yes |
| 6hb Arm HT | 10[188] | AuNRExt 14 | ATTAACCGTTGTAGACTATCGCTACAATAAAAAAAA | no | no | no | no | no | no | yes |
| 6hb Arm HT | 10[209] | AuNRExt 15 | AAGAGTCTGTCCATATCCAGATAGTTGCAAAAAAAA | no | no | no | no | no | no | yes |
| 6hb Arm HT | 10[251] | AuNRExt 16 | ATCCTGAGAAGTGTGCTCATGACCTCCCAAAAAAAA | no | no | no | no | no | no | yes |
| 6hb Arm HT | 10[272] | AuNRExt 17 | AGACAGGAACGGTATTGACGCGAACGCGAAAAAAAA | no | no | no | no | no | no | yes |
| Base Plate | 15[12] 14[12] | Edge Passivation 4C | CCCCAATCGGAACCCTAAATGCCGTAAAGCACTACCCC | no | no | no | no | no | no | yes |
| Base Plate | 6[195] 5[195] | Edge Passivation 4C | CCCCAAGGCAAAGAATTAGCAATAAATCATACAGGCCCCC | no | no | no | no | no | no | yes |
| Base Plate | 23[17] 22[14] | Edge Passivation 4C | CCCCACCAAGCGCGACTTTAATCATCCCC | no | no | no | no | no | no | yes |
| Base Plate | 39[17] 38[17] | Edge Passivation 4C | CCCCCAAATATATTTAGAACGCGCCTCCCC | no | no | no | no | no | no | yes |
| Base Plate | 8[195] 7[195] | Edge Passivation 4C | CCCCATGAACGGTAATCGTAGCAAACAAGAGAATCGCCCC | no | no | no | no | no | no | yes |
| Base Plate | 29[17] 28[17] | Edge Passivation 4C | CCCCTCATTAAAGCCCCACCCTCAGACCCC | no | no | no | no | no | no | yes |
| Base Plate | 16[195] 15[195] | Edge Passivation 4C | CCCCGCGCGTACTATGGTTGAATGCGCCGCTACAGGCCCC | no | no | no | no | no | no | yes |
| Base Plate | 40[200] 39[200] | Edge Passivation 4C | CCCCAAACATAGCGATAGCTTAGATACCAGTATAAAGCCAACGCCCCC | no | no | no | no | no | no | yes |
| Base Plate | 24[200] 23[200] | Edge Passivation 4C | CCCCGCATCGGAACGAGGGTAGCAATGAACGGTGTACAGACCAGCCCC | no | no | no | no | no | no | yes |
| Base Plate | 28[200] 27[200] | Edge Passivation 4C | CCCCTATTCTGAAACATGAAAGTACGTAACGATCTAAAGTTTTGCCCC | no | no | no | no | no | no | yes |
| Base Plate | 40[39] 42[17] | Edge Passivation 4C | AACGCGAGATGATGAAACAAACAGGCGAATTATTCATTTCAATTACCTCCCC | no | no | no | no | no | no | yes |

-continued

| Structure | Pos. in Structure | Oligo Name | Sequence | FIG. 1 | 7 | 8 | 9A,B | 9C,D | 10A,B | 10C,D |
|---|---|---|---|---|---|---|---|---|---|---|
| Base Plate | 33[17] 32[17] | Edge Passivation 4C | CCCCGAAGGAAACCG ACCATTACCATCCCC | no | no | no | no | no | no | yes |
| Base Plate | 7[12] 6[12] | Edge Passivation 4C | CCCCTGTAGGTAAAG ATTCAATGCCTGAGT AATGCCCC | no | no | no | no | no | no | yes |
| Base Plate | 5[12] 4[12] | Edge Passivation 4C | CCCCATAACAGTTGA TTCCGAAGTTTCATTC CATCCCC | no | no | no | no | no | no | yes |
| Base Plate | 42[203] 41[200] | Edge Passivation 4C | CCCCTTTGCACGTAA AACAGAAATTTTTCCC TTAGAATCCTTGACC CC | no | no | no | no | no | no | yes |
| Base Plate | 20[167] 21[198] | Edge Passivation 4C | AGGAATTGAATAATG GAAGGGTTAGAACCT ACCATATCACCCC | no | no | no | no | no | no | yes |
| Base Plate | 35[17] 34[17] | Edge Passivation 4C | CCCCACGCTAACGAG CAAAGTTACCACCCC | no | no | no | no | no | no | yes |
| Base Plate | 20[195] 19[195] | Edge Passivation 4C | CCCCCAGTTGGCAAA TCAACTCAATCAATAT CTGGTCCCC | no | no | no | no | no | no | yes |
| Base Plate | 36[200] 35[200] | Edge Passivation 4C | CCCCGGAATCATTAC CGCGCCCAAGCGCAT TAGACGGGAGAATTC CCC | no | no | no | no | no | no | yes |
| Base Plate | 34[200] 33[200] | Edge Passivation 4C | CCCCAACTGAACACC CTGAACAAATTATTTT GTCACAATCAATACC CC | no | no | no | no | no | no | yes |
| Base Plate | 1[8]2[40] | Edge Passivation 4C | CCCCATTACCTTATG CGATTTTAAGAACTG GCTCAAATACTGC | no | no | no | no | no | no | yes |
| Base Plate | 41[17] 40[17] | Edge Passivation 4C | CCCCGAGCAAAAGAA GAAAACTTTTTCCCC | no | no | no | no | no | no | yes |
| Base Plate | 4[195] 3[195] | Edge Passivation 4C | CCCCCAGACCGGAA GCAAACGAGCTTCAA AGCGAACCCCC | no | no | no | no | no | no | yes |
| Base Plate | 11[12] 10[12] | Edge Passivation 4C | CCCCGGGGATGTGCT GCAAGCCAGCTGGC GAAAGCCCC | no | no | no | no | no | no | yes |
| Base Plate | 31[17] 30[17] | Edge Passivation 4C | CCCCTAGCAAGGCCG CAAATAAATCCCCCC | no | no | no | no | no | no | yes |
| Base Plate | 3[12] 2[12] | Edge Passivation 4C | CCCCAATCCCCTCA AATGCATAAATATTCA TTGCCCC | no | no | no | no | no | no | yes |
| Base Plate | 13[12] 12[12] | Edge Passivation 4C | CCCCTTGGGCGCCA GGGTGGAGGCGGTT TGCGTACCCC | no | no | no | no | no | no | yes |
| Base Plate | 14[195] 13[195] | Edge Passivation 4C | CCCCAGAATAGCCCG AGATATCCCTTATAAA TCAAACCCC | no | no | no | no | no | no | yes |
| Base Plate | 27[17] 26[17] | Edge Passivation 4C | CCCCACCGCCACCCT CTTTAATTGTACCCC | no | no | no | no | no | no | yes |

-continued

| Structure | Pos. in Structure | Oligo Name | Sequence | FIG. 1 | 7 | 8 | 9A,B | 9C,D | 10A,B | 10C,D |
|---|---|---|---|---|---|---|---|---|---|---|
| Base Plate | 22[200] 22[168] | Edge Passivation 4C | CCCCGCGCATAGGCT GGCTGACCTTCATCA AG | no | no | no | no | no | no | yes |
| Base Plate | 32[200] 31[200] | Edge Passivation 4C | CCCCGAAAATTCATA TGGTTTACCTAATCAA AATCACCGGAACCCC CC | no | no | no | no | no | no | yes |
| Base Plate | 9[12] 8[12] | Edge Passivation 4C | CCCCAACGCCATCAA AAATTTTTTAACCAAT AGGCCCC | no | no | no | no | no | no | yes |
| Base Plate | 37[17] 36[17] | Edge Passivation 4C | CCCCGTTTATCAACA GAATCTTACCACCCC | no | no | no | no | no | no | yes |
| Base Plate | 12[195] 11[195] | Edge Passivation 4C | CCCCATTCCACACAA CATACTTGTTATCCG CTCACACCCC | no | no | no | no | no | no | yes |
| Base Plate | 26[200] 25[200] | Edge Passivation 4C | CCCCTCGTCTTTCCA GACGTTAGTACCCTC AGCAGCGAAAGACAC CCC | no | no | no | no | no | no | yes |
| Base Plate | 2[195] 1[195] | Edge Passivation 4C | CCCCGAATTACGAGG CATAGTACATAACGC CAAAAGCCCC | no | no | no | no | no | no | yes |
| Base Plate | 30[200] 29[200] | Edge Passivation 4C | CCCCAGAGCCACCAC CGGAACCGCCTGCCT ATTTCGGAACCTATC CCC | no | no | no | no | no | no | yes |
| Base Plate | 38[200] 37[200] | Edge Passivation 4C | CCCCTCAACAGTAGG GCTTAATTGCCGTTTT TATTTTCATCGTACCCC | no | no | no | no | no | no | yes |
| Base Plate | 21[12] 20[12] | Edge Passivation 4C | CCCCATTAATTTTAAA AGTCTTTGCCCGAAC GTTCCCC | no | no | no | no | no | no | yes |
| Base Plate | 18[195] 17[195] | Edge Passivation 4C | CCCCCTGAAATGGAT TATTTTTTGACGCTCA ATCGTCCCC | no | no | no | no | no | no | yes |
| Base Plate | 19[12] 18[12] | Edge Passivation 4C | CCCCACATCGCCATT AAAAACTGATAGCCC TAAACCCC | no | no | no | no | no | no | yes |
| Base Plate | 10[195] 9[195] | Edge Passivation 4C | CCCCTTTGAGGGGAC GACGAACCGTGCATC TGCCAGCCCC | no | no | no | no | no | no | yes |
| Base Plate | 25[17] 24[17] | Edge Passivation 4C | CCCCTCGGTTTATCA CCCAGCGATTACCCC | no | no | no | no | no | no | yes |
| Base Plate | 17[12] 16[12] | Edge Passivation 4C | CCCCCACGCAAATTA ACCGAAAGAGTCTGT CCATCCCC | no | no | no | no | no | no | yes |
| Base Plate | 15[12] 14[12] | Edge Passivation 4T | TTTTAATCGGAACCCT AAATGCCGTAAAGCA CTATTTT | yes | yes | yes | yes | yes | yes | no |
| Base Plate | 6[195] 5[195] | Edge Passivation 4T | TTTTAAGGCAAAGAAT TAGCAATAAATCATAC AGGCTTTT | yes | yes | yes | yes | yes | yes | no |
| Base Plate | 23[17] 22[14] | Edge Passivation 4T | TTTTACCAAGCGCGA CTTTAATCATTTTT | yes | yes | yes | yes | yes | yes | no |

-continued

| Structure | Pos. in Structure | Oligo Name | Sequence | FIG. 1 | 7 | 8 | 9A,B | 9C,D | 10A,B | 10C,D |
|---|---|---|---|---|---|---|---|---|---|---|
| Base Plate | 39[17] 38[17] | Edge Passivation 4T | TTTTCAAATATATTTA GAACGCGCCTTTTT | yes | yes | yes | yes | yes | yes | no |
| Base Plate | 8[195] 7[195] | Edge Passivation 4T | TTTTATGAACGGTAAT CGTAGCAAACAAGAG AATCGTTTT | yes | yes | yes | yes | yes | yes | no |
| Base Plate | 29[17] 28[17] | Edge Passivation 4T | TTTTTCATTAAAGCCC CACCCTCAGATTTT | yes | yes | yes | yes | yes | yes | no |
| Base Plate | 16[195] 15[195] | Edge Passivation 4T | TTTTGCGCGTACTAT GGTTGAATGCGCCGC TACAGGTTTT | yes | yes | yes | yes | yes | yes | no |
| Base Plate | 40[200] 39[200] | Edge Passivation 4T | TTTTAAACATAGCGAT AGCTTAGATACCAGT ATAAAGCCAACGCTT TT | yes | yes | yes | yes | yes | yes | no |
| Base Plate | 24[200] 23[200] | Edge Passivation 4T | TTTTGCATCGGAACG AGGGTAGCAATGAAC GGTGTACAGACCAGT TTT | yes | yes | yes | yes | yes | yes | no |
| Base Plate | 28[200] 27[200] | Edge Passivation 4T | TTTTTATTCTGAAACA TGAAAGTACGTAACG ATCTAAAGTTTTGTTTT | yes | yes | yes | yes | yes | yes | no |
| Base Plate | 40[39] 42[17] | Edge Passivation 4T | AACGCGAGATGATGA AACAAACAGGCGAAT TATTCATTTCAATTAC CTTTTT | yes | yes | yes | yes | yes | yes | no |
| Base Plate | 33[17] 32[17] | Edge Passivation 4T | TTTTGAAGGAAACCG ACCATTACCATTTTT | yes | yes | yes | yes | yes | yes | no |
| Base Plate | 7[12] 6[12] | Edge Passivation 4T | TTTTTGTAGGTAAAGA TTCAATGCCTGAGTA ATGTTTT | yes | yes | yes | yes | yes | yes | no |
| Base Plate | 5[12] 4[12] | Edge Passivation 4T | TTTTATAACAGTTGAT TCCGAAGTTTCATTC CATTTTT | yes | yes | yes | yes | yes | yes | no |
| Base Plate | 42[203] 41[200] | Edge Passivation 4T | TTTTTTTGCACGTAAA ACAGAAATTTTTCCCT TAGAATCCTTGATTTT | yes | yes | yes | yes | yes | yes | no |
| Base Plate | 20[167] 21[198] | Edge Passivation 4T | AGGAATTGAATAATG GAAGGGTTAGAACCT ACCATATCATTTT | yes | yes | yes | yes | yes | yes | no |
| Base Plate | 35[17] 34[17] | Edge Passivation 4T | TTTTACGCTAACGAG CAAAGTTACCATTTT | yes | yes | yes | yes | yes | yes | no |
| Base Plate | 20[195] 19[195] | Edge Passivation 4T | TTTTCAGTTGGCAAAT CAACTCAATCAATATC TGGTTTTT | yes | yes | yes | yes | yes | yes | no |
| Base Plate | 36[200] 35[200] | Edge Passivation 4T | TTTTGGAATCATTACC GCGCCCAAGCGCATT AGACGGGAGAATTTT TT | yes | yes | yes | yes | yes | yes | no |
| Base Plate | 34[200] 33[200] | Edge Passivation 4T | TTTTAACTGAACACCC TGAACAAATTATTTG TCAATCAATATTTT | yes | yes | yes | yes | yes | yes | no |

-continued

| Structure | Pos. in Structure | Oligo Name | Sequence | FIG. 1 | 7 | 8 | 9A,B | 9C,D | 10A,B | 10C,D |
|---|---|---|---|---|---|---|---|---|---|---|
| Base Plate | 1[8]2[40] | Edge Passivation 4T | TTTTATTACCTTATGC GATTTTAAGAACTGG CTCAAATACTGC | yes | yes | yes | yes | yes | yes | no |
| Base Plate | 41[17] 40[17] | Edge Passivation 4T | TTTTGAGCAAAAGAA GAAAACTTTTTTTTT | yes | yes | yes | yes | yes | yes | no |
| Base Plate | 4[195] 3[195] | Edge Passivation 4T | TTTTCAGACCGGAAG CAAACGAGCTTCAAA GCGAACTTTT | yes | yes | yes | yes | yes | yes | no |
| Base Plate | 11[12] 10[12] | Edge Passivation 4T | TTTTGGGGATGTGCT GCAAGCCAGCTGGC GAAAGTTTT | yes | yes | yes | yes | yes | yes | no |
| Base Plate | 31[17] 30[17] | Edge Passivation 4T | TTTTTAGCAAGGCCG CAAATAAATCCTTTT | yes | yes | yes | yes | yes | yes | no |
| Base Plate | 3[12] 2[12] | Edge Passivation 4T | TTTTAATCCCCCTCAA ATGCATAAATATTCAT TGTTTT | yes | yes | yes | yes | yes | yes | no |
| Base Plate | 13[12] 12[12] | Edge Passivation 4T | TTTTTTGGGCGCCAG GGTGGAGGCGGTTT GCGTATTTT | yes | yes | yes | yes | yes | yes | no |
| Base Plate | 14[195] 13[195] | Edge Passivation 4T | TTTTAGAATAGCCCG AGATATCCCTTATAAA TCAAATTTT | yes | yes | yes | yes | yes | yes | no |
| Base Plate | 27[17] 26[17] | Edge Passivation 4T | TTTTACCGCCACCCT CTTTAATTGTATTTT | yes | yes | yes | yes | yes | yes | no |
| Base Plate | 22[200] 22[168] | Edge Passivation 4T | TTTTGCGCATAGGCT GGCTGACCTTCATCA AG | yes | yes | yes | yes | yes | yes | no |
| Base Plate | 32[200] 31[200] | Edge Passivation 4T | TTTTGAAAATTCATAT GGTTTACCTAATCAAA ATCACCGGAACCTTTT | yes | yes | yes | yes | yes | yes | no |
| Base Plate | 9[12] 8[12] | Edge Passivation 4T | TTTTAACGCCATCAAA AATTTTTTAACCAATA GGTTTT | yes | yes | yes | yes | yes | yes | no |
| Base Plate | 37[17] 36[17] | Edge Passivation 4T | TTTTGTTTATCAACAG AATCTTACCATTTT | yes | yes | yes | yes | yes | yes | no |
| Base Plate | 12[195] 11[195] | Edge Passivation 4T | TTTTATTCCACACAAC ATACTTGTTATCCGCT CACATTTT | yes | yes | yes | yes | yes | yes | no |
| Base Plate | 26[200] 25[200] | Edge Passivation 4T | TTTTTCGTCTTTCCAG ACGTTAGTACCCTCA GCAGCGAAAGACATT TT | yes | yes | yes | yes | yes | yes | no |
| Base Plate | 2[195] 1[195] | Edge Passivation 4T | TTTTGAATTACGAGG CATAGTACATAACGC CAAAAGTTTT | yes | yes | yes | yes | yes | yes | no |
| Base Plate | 30[200] 29[200] | Edge Passivation 4T | TTTTAGAGCCACCAC CGGAACCGCCTGCCT ATTTCGGAACCTATTT TT | yes | yes | yes | yes | yes | yes | no |
| Base Plate | 38[200] 37[200] | Edge Passivation 4T | TTTTTCAACAGTAGG GCTTAATTGCCGTTTT TATTTTCATCGTATTTT | yes | yes | yes | yes | yes | yes | no |

US 11,352,254 B2

| Structure | Pos. in Structure | Oligo Name | Sequence | FIG. 1 | 7 | 8 | 9A,B | 9C,D | 10A,B | 10C,D |
|---|---|---|---|---|---|---|---|---|---|---|
| Base Plate | 21[12]<br>20[12] | Edge Passivation 4T | TTTTATTAATTTTAAAA<br>GTCTTTGCCCGAACG<br>TTTTTT | yes | yes | yes | yes | yes | yes | no |
| Base Plate | 18[195]<br>17[195] | Edge Passivation 4T | TTTTCTGAAATGGATT<br>ATTTTTTGACGCTCAA<br>TCGTTTTT | yes | yes | yes | yes | yes | yes | no |
| Base Plate | 19[12]<br>18[12] | Edge Passivation 4T | TTTTACATCGCCATTA<br>AAAACTGATAGCCCT<br>AAATTTT | yes | yes | yes | yes | yes | yes | no |
| Base Plate | 10[195]<br>9[195] | Edge Passivation 4T | TTTTTTTGAGGGGAC<br>GACGAACCGTGCATC<br>TGCCAGTTTT | yes | yes | yes | yes | yes | yes | no |
| Base Plate | 25[17]<br>24[17] | Edge Passivation 4T | TTTTTCGGTTTATCAC<br>CCAGCGATTATTTT | yes | yes | yes | yes | yes | yes | no |
| Base Plate | 17[12]<br>16[12] | Edge Passivation 4T | TTTTCACGCAAATTAA<br>CCGAAAGAGTCTGTC<br>CATTTTT | yes | yes | yes | yes | yes | yes | no |
| Base Plate | 37[28]<br>36[190] | Bottom Layer Polymerization | AACAGAATCTTACCA<br>GGAATCA | no | no | no | no | no | no | no |
| Base Plate | 33[28]<br>32[190] | Bottom Layer Polymerization | ACCGACCATTACCAT<br>GAAAATT | no | no | no | no | no | no | no |
| Base Plate | 31[28]<br>30[190] | Bottom Layer Polymerization | GCCGCAAATAAATCC<br>AGAGCCA | no | no | no | no | no | no | no |
| Base Plate | 42[39]<br>42[21] | Bottom Layer Polymerization | TATTCATTTCAATTAC<br>CT | no | no | no | no | no | no | no |
| Base Plate | 41[28]<br>40[190] | Bottom Layer Polymerization | AGAAGAAAACTTTTTA<br>AACATA | no | no | no | no | no | no | no |
| Base Plate | 27[28]<br>26[190] | Bottom Layer Polymerization | CCCTCTTTAATTGTAT<br>CGTCTT | no | no | no | no | no | no | no |
| Base Plate | 29[28]<br>28[190] | Bottom Layer Polymerization | AGCCCCACCCTCAGA<br>TATTCTG | no | no | no | no | no | no | no |
| Base Plate | 22[31]<br>22[176] | Bottom Layer Polymerization | ACTTTAATCATGCGC<br>ATAGGCTGGCTGACCT | no | no | no | no | no | no | no |
| Base Plate | 25[28]<br>24[190] | Bottom Layer Polymerization | ATCACCCAGCGATTA<br>GCATCGG | no | no | no | no | no | no | no |
| Base Plate | 35[28]<br>34[190] | Bottom Layer Polymerization | CGAGCAAAGTTACCA<br>AACTGAA | no | no | no | no | no | no | no |
| Base Plate | 39[28]<br>38[190] | Bottom Layer Polymerization | ATTTAGAACGCGCCT<br>TCAACAG | no | no | no | no | no | no | no |
| Base Plate | 28[189]<br>27[27] | Bottom Layer Polymerization | AAACATGAAAGTACG<br>TAACGATCTAAAGTTT<br>TGACCGCCA | no | no | no | no | no | no | no |
| Base Plate | 24[189]<br>23[31] | Bottom Layer Polymerization | AACGAGGGTAGCAAT<br>GAACGGTGTACAGAC<br>CAGTACCAAGCGCG | no | no | no | no | no | no | no |

-continued

| Structure | Pos. in Structure | Oligo Name | Sequence | 1 | 7 | 8 | 9A,B | 9C,D | 10A,B | 10C,D |
|---|---|---|---|---|---|---|---|---|---|---|
| Base Plate | 30[189] 29[27] | Bottom Layer Polymerization | CCACCGGAACCGCCT GCCTATTTCGGAACC TATTCATTAA | no | no | no | no | no | no | no |
| Base Plate | 36[189] 35[27] | Bottom Layer Polymerization | TTACCGCGCCAAGC GCATTAGACGGGAGA ATTACGCTAA | no | no | no | no | no | no | no |
| Base Plate | 26[189] 25[27] | Bottom Layer Polymerization | TCCAGACGTTAGTAC CCTCAGCAGCGAAAG ACATCGGTTT | no | no | no | no | no | no | no |
| Base Plate | 40[189] 39[27] | Bottom Layer Polymerization | GCGATAGCTTAGATA CCAGTATAAAGCCAA CGCCAAATAT | no | no | no | no | no | no | no |
| Base Plate | 38[189] 37[27] | Bottom Layer Polymerization | TAGGGCTTAATTGCC GTTTTTATTTTCATCG TAGTTTATC | no | no | no | no | no | no | no |
| Base Plate | 42[196] 41[27] | Bottom Layer Polymerization | TTTGCACGTAAAACA GAAATTTTTCCCTTAG AATCCTTGAGAGCAAA | no | no | no | no | no | no | no |
| Base Plate | 34[189] 33[27] | Bottom Layer Polymerization | CACCCTGAACAAATT ATTTTGTCACAATCAA TAGAAGGAA | no | no | no | no | no | no | no |
| Base Plate | 32[189] 31[27] | Bottom Layer Polymerization | CATATGGTTTACCTAA TCAAAATCACCGGAA CCTAGCAAG | no | no | no | no | no | no | no |

Additional Strands

| Oligo Name | Sequence | 1 | 7 | 8 | 9A,B | 9C,D | 10A,B | 10C,D |
|---|---|---|---|---|---|---|---|---|
| HybrA655 | [Atto655] TT ATATGTACGGGTCTCACTTA | no | no | no | no | no | no | yes |
| HybrA565 | [Atto565] TT CGGAGGTTAAGTAGGTTG | no | no | no | no | no | no | yes |
| Thiol_10T | [thiol] TTTTTTTTTT | no | no | no | no | no | no | yes |

Fixation of Platform

Optional orientation control of the platform 4 during sample preparation is shown in FIG. 11. FIG. 11-A shows a sketch of the designed structures. A long handle 18 is attached to the platform 4, which has the shape of a square plate in this embodiment. The protruding end of the handle 18 is functionalized with a single biotin molecule 22, which can flexibly anchor the construct to an avidin modified surface and hence functions as a primary anchor 19. The edges of the platform 4 can be fixed via secondary anchors 20. Therefore, the platform 4 is extended with secondary anchoring sequences 21. These secondary anchoring sequences 21 allow subsequent fixation upon addition of biotin modified complimentary strands 23. For superresolution optical microscopy various points on the construct are labelled with DNA-PAINT docking sites 24. The workflow of fixation of the platform 4 including orientation control is illustrated in FIG. 11-B. First, the construct comprising platform 4 and handle 18 is flexibly anchored with the primary anchor 19. Second, the handle 18 and the platform 4 are aligned in the direction 25 of an externally applied electric field. This is performed in the same way as aligning the positioning arm 5 after fixation of the platform 4. Third, while aligned, the biotin modified complimentary strands 23 (biotin modified oligonucleotides) are added to facilitate fixation of the secondary anchoring sequences 21 in order to generate the secondary anchors 20. As a result, the platform 4 and the handle 18 stay fixed in the alignment direction after the external field is switched off.

FIG. 11-C shows a DNA-PAINT localization image of aligned structures including platform 4 and handle 18 after the external field has been switched off. The DNA-PAINT localization image shows the positions of the DNA-PAINT docking sites 24. The inset shows a histogram of the angular distribution of structures that were measured in a larger field of view that exhibits a strong preference between 150° and 210°. In the histogram, the circumferential dimension denotes the alignment angle and the radial dimension denotes the number of structures comprising platform 4 and handle 18.

PRIOR ART REFERENCES

1. Hess, H.; Bachand, G. D.; Vogel, V., Powering Nanodevices with Biomolecular Motors. Chemistry 2004, 10, 2110-6.
2. van den Heuvel, M. G. L.; Dekker, C., Motor Proteins at Work for Nanotechnology. Science (New York, N.Y.) 2007, 317, 333-336.
3. Fischer, T.; Agarwal, A.; Hess, H., A Smart Dust Biosensor Powered by Kinesin Motors. Nature Nanotech. 2009, 4, 162-166.
4. van den Heuvel, M. G.; de Graaff, M. P.; Dekker, C., Molecular Sorting by Electrical Steering of Microtubules in Kinesin-Coated Channels. Science (New York, N.Y.) 2006, 312, 910-4.
5. Krishnan, Y.; Simmel, F. C., Nucleic Acid Based Molecular Devices. Angew. Chem. Int. Ed. 2011, 50, 3124-3156.
6. Kopperger, E.; Pirzer, T.; Simmel, F. C., Diffusive Transport of Molecular Cargo Tethered to a DNA Origami Platform. Nano Lett. 2015, 15, 2693-2699.
7. Marras, A. E.; Zhou, L.; Su, H.-J.; Castro, C. E., Programmable Motion of DNA Origami Mechanisms. Proc. Natl. Ac. Sci. 2015, 112, 713-8.
8. Ketterer, P.; Willner, E. M.; Dietz, H., Nanoscale Rotary Apparatus Formed from Tight-Fitting 3d DNA Components. Sci Adv 2016, 2, e1501209.
9. List, J.; Falgenhauer, E.; Kopperger, E.; Pardatscher, G.; Simmel, F. C., Long-Range Movement of Large Mechanically Interlocked DNA Nanostructures. Nat Commun 2016, 7, 12414.
10. Omabegho, T.; Sha, R.; Seeman, N. C., A Bipedal DNA Brownian Motor with Coordinated Legs. Science 2009, 324, 67-71.
11. Green, S.; Bath, J.; Turberfield, A., Coordinated Chemomechanical Cycles: A Mechanism for Autonomous Molecular Motion. Phys. Rev. Lett. 2008, 101, art. no. 238101.
12. Liber, M.; Tomov, T. E.; Tsukanov, R.; Berger, Y.; Nir, E., A Bipedal DNA Motor That Travels Back and Forth between Two DNA Origami Tiles. Small 2014, n/a-n/a.
13. Wickham, S. F. J.; Endo, M.; Katsuda, Y.; Hidaka, K.; Bath, J.; Sugiyama, H.; Turberfield, A. J., Direct Observation of Stepwise Movement of a Synthetic Molecular Transporter. Nature Nanotech. 2011, 6, 166-169.
14. Asanuma, H.; Liang, X.; Yoshida, T.; Komiyama, M., Photocontrol of DNA Duplex Formation by Using Azobenzene-Bearing Oligonucleotides. Chembiochem 2001, 2, 39-44.
15. Kang, H.; Liu, H.; Phillips, J. A.; Cao, Z.; Kim, Y.; Chen, Y.; Yang, Z.; Li, J.; Tan, W., Single-DNA Molecule Nanomotor Regulated by Photons. Nano Lett. 2009, 9, 2690-2696.
16. Suzuki, Y.; Endo, M.; Yang, Y.; Sugiyama, H., Dynamic Assembly/Disassembly Processes of Photoresponsive DNA Origami Nanostructures Directly Visualized on a Lipid Membrane Surface. J. Am. Chem. Soc. 2014, 136, 1714-1717.
17. Rothemund, P. W. K., Folding DNA to Create Nanoscale Shapes and Patterns. Nature 2006, 440, 297-302.
18. Douglas, S. M.; Dietz, H.; Liedl, T.; Högberg, B.; Graf, F.; Shih, W. M., Self-Assembly of DNA into Nanoscale Three-Dimensional Shapes. Nature 2009, 459, 414-8.
19. Lin, C.; Jungmann, R.; Leifer, A. M.; Li, C.; Levner, D.; Church, G. M.; Shih, W. M.; Yin, P., Submicrometre Geometrically Encoded Fluorescent Barcodes Self-Assembled from DNA. Nature Chem. 2012, 4, 832-839.
20. Li, X.; Liu, D. R., DNA-Templated Organic Synthesis: Nature's Strategy for Controlling Chemical Reactivity Applied to Synthetic Molecules. Angew. Chem. Int. Ed. 2004, 43, 4848-4870.
21. He, Y.; Liu, D. R., Autonomous Multistep Organic Synthesis in a Single Isothermal Solution Mediated by a DNA Walker. Nature Nanotech. 2010, 5, 778-782.
22. Rant, U.; Pringsheim, E.; Kaiser, W.; Arinaga, K.; Knezevic, J.; Tornow, M.; Fujita, S.; Yokoyama, N.; Abstreiter, G., Detection and Size Analysis of Proteins with Switchable DNA Layers. Nano Letters 2009, Vol. 9, No. 4, 1290-1295.
23. Yang, Y.; Tashiro, R.; Suzuki, Y.; Emura, T.; Hidaka, K.; Sugijama, H.; Endo, M., A Photoregulated DNA-Based Rotary System and Direct Observation of Its Rotational Movement. Chemistry, 2007, 23, 1-8.
24. Campos, R.; Zhang, S.; Majikes, J. M.; Ferraz, L. C. C.; LaBean, T. H.; Dong, M. D.; Ferapotova, E. E., Electronically addressable nanomechanical switching of i-motif DNA origami assembled on basal plane HOPG. ChemComm, 2015, 51, 14111-14114.

LIST OF REFERENCE SIGNS

1 molecular machine
2 movement part
3 control part
4 platform (first molecular element)
5 positioning arm (second molecular element)
6 linking element
7 first electrical device
8 second electrical device
9 first fluidic channel
10 second fluidic channel
11 electrode
12 intersection area
13 isolating element
14 additional lever/pointer structure
15 donor dye
16 first acceptor dye
17 second acceptor dye
18 handle
19 primary anchor
20 secondary anchor
21 secondary anchoring sequences
22 biotin molecule
23 biotin modified complimentary strand
24 DNA-PAINT docking sites
25 direction of electrical field

The invention claimed is:

1. A molecular machine (1), comprising:
a movement part (2) including:
a first molecular element (4),
a second molecular element (5), and
a linking element (6) for constraining a relative movement of the first molecular element (4) and the second molecular element (5), and
a control part (3) configured to generate an electrical field around the movement part (2),
wherein the first molecular element (4) is fixed relative to the control part (3),
wherein the second molecular element (5) is movable relative to the first molecular element (4) in at least one degree of freedom, and
wherein the second molecular element (5) is electrically charged such that the second molecular element (5) aligns to said electrical field.

2. The molecular machine of claim 1, wherein the control part (3) comprises a fluidic channel (9, 10), in which the movement part (2) is provided, wherein the control part (3) has an electrical device (7, 8) that includes electrodes (11) for creating the electrical field, and wherein the electrodes are connected to the fluidic channel (9, 10).

3. The molecular machine of claim 2, wherein the control part (3) comprises at least two electrical devices (7, 8) and fluidic channels (9, 10) with different orientations to create at least two independent overlaying electrical fields.

4. The molecular machine of claim 2, wherein the first molecular element (4) is fixed to the fluidic channel (9, 10).

5. The molecular machine of claim 2, wherein the electrical device (7, 8) includes an isolating element (13) configured to isolate the electrodes (11) from the movement part (2).

6. The molecular machine of claim 1, wherein the linking element (6) is part of the first molecular element (4) or the second molecular element (5).

7. The molecular machine of claim 1, wherein at least one of the first molecular element (4), the second molecular element (5), and the linking element (6) are biomolecules.

8. The molecular machine of claim 1, wherein the first molecular element (4) is a platform, wherein the second molecular element (5) is a positioning arm, and wherein the linking element (6) constrains all relative movement of the first molecular element (4) and the second molecular element (5) except of a rotation of the second molecular element (5) within a plane parallel to the first molecular element (4).

9. The molecular machine of claim 1, wherein fluctuations of at least one of the first molecular element (4) and the second molecular element (5) due to diffusion are within a tolerance of at most 10 nm.

10. The molecular machine of claim 1, wherein any dimension of the first molecular element (4) and the second molecular element (5) is less than 1000 nm.

11. The molecular machine of claim 1, wherein the first molecular element (4) is made from a crossed two-layer scaffold routing, in which a top layer is rotated with respect to a bottom layer by an angle between 80° and 100°.

12. The molecular machine of claim 1, wherein the second molecular element (5) is made from a DNA six-helix bundle.

13. The molecular machine of claim 1, wherein the linking element (6) is created by two adjacent scaffold crossovers with three and four unpaired bases.

14. The molecular machine of claim 1, wherein the second molecular element (5) is adapted to transport inorganic nanoparticles.

15. The molecular machine of claim 3, wherein the fluidic channels (9, 10) are arranged to intersect at an intersection area (12), and the movement part (2) is placed at the intersection area (12).

16. The molecular machine of claim 7, wherein at least one of the first molecular element (4), the second molecular element (5), and the linking element (6), are made of at least one of DNA, DNA-origami, RNA, protein, and artificial charged supramolecular structures.

17. The molecular machine of claim 9, wherein fluctuations of at least one of the first molecular element (4) and the second molecular element (5) due to diffusion are within a tolerance of at most 1 nm.

18. The molecular machine of claim 9, wherein fluctuations of at least one of the first molecular element (4) and the second molecular element (5) due to diffusion are within a tolerance of at most 0.5 nm.

19. The molecular machine of claim 11, wherein the top layer is rotated with respect to a bottom layer by an angle of 90°.

\* \* \* \* \*